US010119119B2

(12) United States Patent
Feinberg et al.

(10) Patent No.: US 10,119,119 B2
(45) Date of Patent: Nov. 6, 2018

(54) POLYSILOXANE SUBSTRATES WITH HIGHLY-TUNABLE ELASTIC MODULUS

(71) Applicants: Carnegie Mellon University, Pittsburgh, PA (US); University of Pittsburgh—Of the Commonwealth System of Higher Education, Pittsburgh, PA (US)

(72) Inventors: Adam Walter Feinberg, Pittsburgh, PA (US); James L. Funderburgh, Pittsburgh, PA (US); Rachelle Simko, Pittsburgh, PA (US)

(73) Assignee: Carnegie Mellon University and University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 266 days.

(21) Appl. No.: 14/375,705

(22) PCT Filed: Jan. 31, 2013

(86) PCT No.: PCT/US2013/024070
§ 371 (c)(1),
(2) Date: Jul. 30, 2014

(87) PCT Pub. No.: WO2013/116473
PCT Pub. Date: Aug. 8, 2013

(65) Prior Publication Data
US 2015/0010919 A1 Jan. 8, 2015

Related U.S. Application Data

(60) Provisional application No. 61/632,787, filed on Jan. 31, 2012, provisional application No. 61/735,249, filed on Dec. 10, 2012.

(51) Int. Cl.
| | | |
|---|---|---|
| C12N 5/00 | (2006.01) |
| A61L 27/18 | (2006.01) |
| A61L 27/22 | (2006.01) |
| A61L 27/44 | (2006.01) |
| C08L 83/04 | (2006.01) |
| B05D 1/28 | (2006.01) |
| B05D 1/36 | (2006.01) |
| B05D 7/00 | (2006.01) |
| C12M 1/00 | (2006.01) |
| G01N 33/569 | (2006.01) |
| C12M 1/12 | (2006.01) |
| C08L 83/00 | (2006.01) |
| C08G 77/12 | (2006.01) |
| C08G 77/24 | (2006.01) |
| C08G 77/26 | (2006.01) |

(52) U.S. Cl.
CPC ............ *C12N 5/0068* (2013.01); *A61L 27/18* (2013.01); *A61L 27/22* (2013.01); *A61L 27/446* (2013.01); *B05D 1/286* (2013.01); *B05D 1/36* (2013.01); *B05D 7/54* (2013.01); *C08L 83/00* (2013.01); *C08L 83/04* (2013.01); *C12M 23/20* (2013.01); *C12M 25/14* (2013.01); *G01N 33/56966* (2013.01); *A61L 2400/12* (2013.01); *C08G 77/12* (2013.01); *C08G 77/24* (2013.01); *C08G 77/26* (2013.01); *C08K 2201/011* (2013.01); *C12N 2533/30* (2013.01)

(58) Field of Classification Search
CPC ...... A61L 2400/12; A61L 27/18; A61L 27/22; A61L 27/446; B05D 1/286; B05D 1/36; B05D 7/54; C08G 77/12; C08G 77/24; C08G 77/26; C08K 2201/011; C08L 83/00; C08L 83/04; C12M 23/20; C12M 25/14; C12N 2533/30; C12N 5/0068; G01N 33/56966
See application file for complete search history.

(56) References Cited

U.S. PATENT DOCUMENTS

| | | | | |
|---|---|---|---|---|
| 5,444,106 A | * | 8/1995 | Zhou ................. | A61L 27/18 523/105 |
| 2005/0013870 A1 | * | 1/2005 | Freyman ............. | A61L 27/3633 424/520 |
| 2006/0204441 A1 | | 9/2006 | Atala et al. | |
| 2008/0261288 A1 | * | 10/2008 | Gonda ................. | C12M 21/08 435/174 |
| 2010/0010105 A1 | | 1/2010 | Mason et al. | |
| 2012/0273702 A1 | * | 11/2012 | Culbertson ....... | B01L 3/502707 251/129.01 |

FOREIGN PATENT DOCUMENTS

| | | | |
|---|---|---|---|
| WO | 2007100845 A2 | 9/2007 | |
| WO | WO 2010123820 A2 * | 10/2010 | ........ B01L 3/502707 |

OTHER PUBLICATIONS

Brown et al. (2005) Biomaterials 26(16): 3123-3129.*
Palchesko et al. (2012) PLoS One 7(12): 1-13 (Year: 2012).*
Ahmed, N., et al., Long-term in situ observation of barnacle growth on soft substrates with different elasticity and wettability, Soft Matter, 2011, vol. 7, pp. 7281-7290.
Bartalena, G., et al., A novel method for assessing adherent single-cell stiffness in tension: design and testing of a substrate-based live cell functional imaging device, Biomed Microdevices, 2011, vol. 13, pp. 291-301.

(Continued)

*Primary Examiner* — Lisa J Hobbs
(74) *Attorney, Agent, or Firm* — The Webb Law Firm

(57) ABSTRACT

A highly tunable bioscaffold is provided, as well as a method of manufacture of the bioscaffold and methods of use of the bioscaffold, for example for drug testing, cell propagation and for optimizing growth of a cell type, for example corneal endothelial cells.

20 Claims, 19 Drawing Sheets

(56) References Cited

OTHER PUBLICATIONS

Behndig, A., et al., Corneal endothelial integrity in mice lacking extracellular superoxide dismutase, Investigative Ophthalmology & Visual Science, Nov. 2001, vol. 42, No. 12, pp. 2784-2788.
Behndig, A., Corneal endothelial integrity in aging mice lacking superoxide dismutase-1 and/or superoxide dismutase-3. Molecular Vision, Nov. 7, 2008, vol. 14, pp. 2025-2030.
Blenkinsop, T. A., et al., The culture and maintenance of functional retinal pigment epithelial monolayers from adult human eye, in Scott H. Randell and M. Leslie Fulcher (eds.), Epithelial Cell Culture Protocols: Second Edition, Methods in Molecular Biology, vol. 945, DOI 10.1007/978-1-62703-125-7_4, © Springer Science+Business Media, LLC 2012, Chapter 4.
Boonen, K.J.M., et al., Essential environmental cues from the satellite cell niche: optimizing proliferation and differentiation, American Journal of Physiology—Cell Physiology, Mar. 25, 2009, vol. 296, pp. C1338-C1345.
Boonen, K.J.M., et al., Interaction between electrical stimulation, protein coating and matrix elasticity: a complex effect on muscle fibre maturation, Journal of Tissue Engineering and Regenerative Medicine, 2011, vol. 5, pp. 60-68.
Brown, X.Q., et al., Evaluation of polydimethylsiloxane scaffolds with physiologically-relevant elastic moduli: interplay of substrate mechanics and surface chemistry effects on vascular smooth muscle cell response, Biomaterials, 2005, vol. 26, pp. 3123-3129.
Chandler, E.M., et al., Adipose progenitor cells increase fibronectin matrix strain and unfolding in breast tumors, Physical Biology, 2011, vol. 8, pp. 1-13.
Cheng, C-M, et al., Probing cell structure by controlling the mechanical environment with cell-substrate interactions, Journal of Biomechanics, 2009, vol. 42, pp. 187-192.
Cheng, M., et al., Study on physical properties and nerve cell affinity of composite films from chitosan and gelatin solutions, Biomaterials, 2003, vol. 24, pp. 2871-2880.
Chowdhury, F., et al., Soft substrates promote homogeneous self-renewal of embryonic stem cells via downregulating cell-matrix tractions, PLoS One, Dec. 2010, vol. 5, Issue 12, pp. 1-10.
Engler, A.J., et al., Embryonic cardiomyocytes beat best on a matrix with heart-like elasticity: scar-like rigidity inhibits beating, Journal of Cell Science, Nov. 15, 2008, vol. 121, pp. 3794-3802.
Engler, A.J., et al., Matrix elasticity directs stem cell lineage specification, Cell, Aug. 25, 2006, vol. 126, pp. 677-689.
Engler, A.J., et al., Myotubes differentiate optimally on substrates with tissue-like stiffness: pathological implications for soft or stiff microenvironments, Journal of Cell Biology, Sep. 13, 2004, vol. 166, pp. 877-887.
Evans, N.D., et al., Substrate stiffness affects early differentiation events in embryonic stem cells, European Cells and Materials, 2009, vol. 18, pp. 1-14.
Feinberg, A.W., et al., Investigating the energetics of bioadhesion on microengineered siloxane elastomers: characterizing the topography, mechanical properties, and surface energy and their effect on cell contact guidance, American Chemical Society, 2003, pp. 196-211.
Feinberg, A.W., et al., Effect of argon plasma treatment on PDMS elastomer investigated by AFM, Abstracts of Papers of the American Chemical Society, 225th ACS National Meeting, Mar. 23-27, 2003, pp. PMSE-330.
Feinberg, A.W., et al., Surface-initiated assembly of protein nanofabrics, Nano Letters, 2010, vol. 10, pp. 2184-2191.
Feinberg, A.W., et al., Controlling the contractile strength of engineered cardiac muscle by hierarchal tissue architecture, Biomaterials, Aug. 2012, vol. 33, No. 23, pp. 5732-5741.
Fuard, D., et al., Optimization of poly-di-methyl-siloxane (PDMS) substrates for studying cellular adhesion and motility, Microelectronic Engineering, 2008, vol. 85, pp. 1289-1293.
Gray, D.S., et al., Repositioning of cells by mechanotaxis on surfaces with micropatterned Young's modulus, Journal of Biomedical Materials Research, 2003, vol. 66A, pp. 605-614.
Guilak, F., et al., Control of stem cell fate by physical interactions with the extracellular matrix, Cell Stem Cell, Jul. 2, 2009, vol. 5, No. 1, pp. 17-26.
Hillborg, H., et al., Nanoscale hydrophobic recovery: A chemical force microscopy study of UV/ozone-treated cross-linked poly(dimethylsiloxane), Langmuir, 2004, vol. 20, pp. 785-794.
Hu, X, et al., The influence of elasticity and surface roughness on myogenic and osteogenic-differentiation of cells on silk-elastin biomaterials, Biomaterials, Dec. 2011, vol. 32, No. 34, pp. 8979-8989.
Ju, C., et al., Derivation of corneal endothelial cell-like cells from rat neural crest cells in vitro, PLoS one, Jul. 2012, vol. 7, Issue 7, pp. 1-10.
Khademhosseini, A., et al., Microscale technologies for tissue engineering and biology, Proceedings of the National Academy of Sciences, Feb. 21, 2006, vol. 103, No. 8, pp. 2480-2487.
Kim, J-H, et al., Hydrophobically recovered and contact printed siloxane oligomers for general-purpose surface patterning, Langmuir, 2010, vol. 26, No. 15, pp. 13015-13019.
Kokkinaki, M., et al., Human iPS-derived retinal pigment epithelium (RPE) cells exhibit ion transport, membrane potential, polarized VEGF secretion and gene expression pattern similar to native RPE, Stem Cells, May 2011, vol. 29, No. 5, pp. 825-835.
Kumar, S., et al., Mechanics, malignancy, and metastasis: The force journey of a tumor cell, Cancer Metastasis Reviews, Jun. 2009, vol. 28, No. 1-2, pp. 113-127.
Kuznetsova, A. V., et al., Human adult retinal pigment epithelial cells as potential cell source for retina recovery, Cell and Tissue Biology, 2011, vol. 5, No. 5, pp. 495-502.
Leach, J.B., et al., Neurite outgrowth and branching of PC12 cells on very soft substrates sharply decreases below a threshold of substrate rigidity, Journal of Neural Engineering, 2007, vol. 4, pp. 26-34.
Liao, Q., et al., A hybrid model to determine mechanical properties of soft polymers by nanoindentation, Mechanics of Materials, 2010, vol. 42, pp. 1043-1047.
Mata, A., et al., Microfabricated 3D scaffolds for tissue engineering applications, Materials Research Society Symposium Proceedings, Nanoscale Materials Science in Biology and Medicine, 2005, vol. 845, pp. 97-103.
Meijering, E., et al., Design and validation of a tool for neurite tracing and analysis in fluorescence microscopy images, Cytometry Part A, 2004, vol. 58, pp. 167-176.
Mi, Y., et al., Micromolding of PDMS scaffolds and microwells for tissue culture and cell patterning: A new method of microfabrication by the self-assembled micropatterns of diblock copolymer micelles, Polymer, 2006, vol. 47, pp. 5124-5130.
Ochsner, M., et al., Micro-well arrays for 3D shape control and high resolution analysis of single cells, Lab Chip 2007, vol. 7, pp. 1074-1077.
Okumura, N., et al., Enhancement on primate corneal endothelial cell survival in vitro by a ROCK inhibitor, Investigative Ophthalmology & Visual Science, Aug. 2009, vol. 50, No. 8, pp. 3680-3687.
Okumura, N., et al., Enhancement of corneal endothelium wound healing by Rho-associated kinase (ROCK) inhibitor eye drops, British Journal of Ophthalmology, 2011, vol. 95, pp. 1006-1009.
Olah, A., et al., Hydrophobic recovery of UV/ozone treated poly(dimethylsiloxane): adhesion studies by contact mechanics and mechanism of surface modification, Applied Surface Science, 2005, vol. 239, pp. 410-423.
Peh, G., et al., Human corneal endothelial cell expansion for corneal endothelium transplantation: An overview, Transplantation, Apr. 2011, vol. 91, No. 8, pp. 811-819.
Pelham, R.J., Jr., et al., Cell locomotion and focal adhesions are regulated by substrate flexibility, Proceedings of the National Academy of Sciences USA, Cell Biology, Dec. 1997, vol. 94, pp. 13661-13665.
Perl, A., et al., Microcontact printing: Limitations and achievements, Advanced Materials, 2009, vol. 21, pp. 2257-2268.
Proulx, S., et al., Methods being developed for preparation, delivery and transplantation of a tissue-engineered corneal endothelium, Experimental Eye Research, 2012, vol. 95, pp. 68-75.

(56) References Cited

OTHER PUBLICATIONS

Schmidt, C.E., et al., Neural Tissue Engineering: Strategies for repair and regeneration, Annual Review of Biomedical Engineering, 2003, vol. 5, pp. 293-347.

Schneider, F., et al., Process and material properties of polydimethylsiloxane (PDMS) for Optical MEMS, Sensors and Actuators A, 2009, vol. 151, pp. 95-99.

Smith, M.L, et al., Force-induced unfolding of fibronectin in the extracellular matrix of living cells, PLoS Bio, Oct. 2007, vol. 5, Issue 10, pp. 2243-2254.

Sun, Y., et al., UV-modulated substrate rigidity for multiscale study of mechanoresponsive cellular behaviors, Langmuir, 2012, vol. 28, pp. 10789-10796.

Tzvetkova-Chevolleau, T., et al., The motility of normal and cancer cells in response to the combined influence of the substrate rigidity and anisotropic microstructure, Biomaterials, 2008, vol. 29, pp. 1541-1551.

Wang, L., et al., Chemical and physical modifications to poly(dimethylsiloxane) surfaces affect adhesion of Caco-2 cells, Journal of Biomedical Materials Research, 2010, vol. 93A, pp. 1260-1271.

West-Mays, J. A., et al., The keratocyte: Corneal stromal cells with variable repair phenotypes, International Journal of Biochemistry Cell Biology, 2006, vol. 38, No. 10, pp. 1625-1631.

Wilson, K. S., et al., Polydimethylsiloxane-magnetite nanoparticle complexes and dispersions in polysiloxane carrier fluids, Polymers for Advanced Technologies, 2005, vol. 16, pp. 200-211.

Yamamoto, M., et al., The effect of ROCK inhibitor on corneal wound healing and the transformation of keratocytes, International Journal of Experimental Pathology, vol. 92, A17.

Young, R. R., Adult Stem Cell Fact Sheet, New York Stem Cell Summit, 2012, pp. 1-18.

Yu, H., et al., A novel and simple microcontact printing technique for tacky, soft substrates and/or complex surfaces in soft tissue engineering, Acta Biomaterialia, 2012, vol. 8, pp. 1267-1272.

Zhang, Y-S., et al., Derivation, culture and retinal pigment epithelial differentiation of human embryonic stem cells using human fibroblast feeder cells, J Assist Reprod Genet, 2012, vol. 29, pp. 735-744.

Zoldan, J., et al., The influence of scaffold elasticity on germ layer specification of human embryonic stem cells, Biomaterials, Dec. 2011, vol. 32, No. 36, pp. 9612-9621.

\* cited by examiner

|  | Sylgard 184 1.72 MPa | 5:1 1.34 MPa | 1:1 830 kPa | 1:5 130 kPa | 1:10 50 kPa | Sylgard 527 5 kPa |
|---|---|---|---|---|---|---|
| Uncoated | | | | | | |
| Fibronectin | | | | | | |
| Collagen I | | | | | | |
| Laminin | | | | | | |
| Collagen IV | | | | | | |
| Lam + Col4 | | | | | | |

1. Spincoat PIPAAm onto glass

2. Spincoat PDMS onto PIPAAm

3. Coat with collagen IV

4. Seed with cells, culture until confluent

5. Dissolve PIPAAm to release thin film

Released corneal endothelial thin film

POLYSILOXANE SUBSTRATES WITH HIGHLY-TUNABLE ELASTIC MODULUS

CROSS-REFERENCE TO RELATED APPLICATIONS

This application is the United States national phase of International Application No. PCT/US2013/024070 filed Jan. 31, 2013, and claims priority to U.S. Provisional Patent Application Nos. 61/632,787 and 61/735,249, filed Jan. 31, 2012 and Dec. 10, 2012, respectively, the disclosures of which are hereby incorporated in their entirety by reference.

A bioscaffold is provided, along with related devices, methods of manufacture and methods of use.

The mechanical environment of a cell has a profound effect on cell survival, proliferation, adhesion, differentiation and metabolism. For example, Pelham and Wang reported in 1997 that focal adhesion formation and migration of cultured rat kidney epithelial cells and 3T3 fibroblasts were regulated by the stiffness of polyacrylamide (PA) gels (Pelham R J, Jr., Wang Y (1997) Cell locomotion and focal adhesions are regulated by substrate flexibility. Proc Natl Acad Sci USA 94: 13661-13665) and in 2006 Engler et al demonstrated that mesenchymal stem cell specification on collagen coated PA gels was directed towards neurons, muscle and bone on substrates that matched the elastic modulus of these tissues (Engler A J, Sen S, Sweeney H L, Discher D E (2006) Matrix elasticity directs stem cell lineage specification. Cell 126: 677-689). The insights gained from these types of studies have been extended into other areas where the mechanical environment is now recognized as an important factor. Recent work in cancer biology has revealed that the extracellular matrix (ECM) in tumors is characterized by increased stiffness and that ECM remodeling can lead to invasion and metastasis (Kumar S, Weaver V (2009) Mechanics, malignancy, and metastasis: The force journey of a tumor cell. Cancer and Metastasis Reviews 28: 113-127 and Chandler E M, Saunders M P, Yoon C J, Gourdon D, Fischbach C (2011) Adipose progenitor cells increase fibronectin matrix strain and unfolding in breast tumors. Physical Biology 8: 015008). Stem cells are similarly sensitive to ECM and substrate mechanics (Guilak F, Cohen D M, Estes B T, Gimble J M, Liedtke W, et al. (2009) Control of Stem Cell Fate by Physical Interactions with the Extracellular Matrix. Cell Stem Cell 5: 17-26), where control of stiffness can drive differentiation into specific lineages (Engler A J, et al. Journal of Cell Science 121: 3794-3802 and Zoldan J, Karagiannis E D, Lee C Y, Anderson D G, Langer R, et al. (2011) The influence of scaffold elasticity on germ layer specification of human embryonic stem cells. Biomaterials 32: 9612-9621) or maintain stem cells in a pluripotent state (Chowdhury F, Li Y, Poh Y—C, Yokohama-Tamaki T, Wang N, et al. (2010) Soft Substrates Promote Homogeneous Self-Renewal of Embryonic Stem Cells via Downregulating Cell-Matrix Tractions. PLoS One 5: e15655). The commonalities between these studies are experimental tools that control the mechanical environment of cells by modulating the stresses and/or strains cells sense and respond to. Understanding the underlying mechanobiology is critical to moving the field forward and developing improved models of health and disease as well as engineering in vitro platforms for cell analysis, tissue engineering scaffolds and regenerative medicine strategies. As the importance of the mechanical environment on cell behavior has been realized, researchers have developed a number of materials systems to probe these interactions. PA gels have been widely used to create substrates with elastic moduli (E) in the range of ~0.1 kPa to ~100 kPa, covering the range of many types of soft tissues in the body. Other types of hydrogels have also been used over a similar stiffness range including synthetic systems based on polyethylene glycol as well as naturally derived polymers including hyaluron, methylcellulose, dextran, gelatin and fibrin. However, many tissue structures in the body are stiffer than these materials including dense ECM structures such as many types of basement membranes (E ~1 MPa). Further, at the tissue-scale cells may experience an effectively stiffer environment, such as arterial walls (E ~800 kPa) and cardiac muscle under physiologic blood pressures (left ventricle at peak systole, E≈30-400 kPa).

Rubber-like elastomers have elastic moduli in this range including polydimethylsiloxane (PDMS), poly(n-butyl) acrylate and polyesters. However, the chemistry, water content and surface energy of these elastomers is substantially different then the softer hydrogels and have different synthesis and processing requirements. To date, no single material has been able to effectively cover the entire range of soft tissue elastic moduli from approximately 1 kPa to >1 MPa without changes in other major surface and/or bulk properties known to influence cell behavior.

Polyacrylamide gels have been the de facto standard for studying cell response to substrates with elastic modulus in the range of 1 to 100 kPa. This range is comparable to the elastic modulus of many soft tissue types, but there are also many soft tissues that have much higher reported elastic moduli. Studies with stiffer materials have demonstrated that cells are also sensitive to differences in substrate elastic modulus in this higher range from 100 kPa to 1 MPa. Unfortunately, it has been difficult to study cell response continuously across the entire elastic modulus range of soft tissues from 1 kPa to 1 MPa because it required using different materials with different chemical and physical properties.

Sylgard 184 has been used in a number of cell culture studies. It is a composition comprising dimethylvinyl-terminated dimethyl siloxane, dimethyl, methylhydrogen siloxane and silca particles. The most common technique to decrease the elastic modulus of Sylgard 184 has been to decrease the ratio of curing agent to base resin from the manufacturer's recommendation of 1:10 to as low as 1:70 (Feinberg A W, et al. (2012) Controlling the contractile strength of engineered cardiac muscle by hierarchal tissue architecture. Biomaterials; Liao Q, et al. (2010) A hybrid model to determine mechanical properties of soft polymers by nanoindentation. Mechanics of Materials 42: 1043-1047; Bartalena G, et al. (2011) A novel method for assessing adherent single-cell stiffness in tension: design and testing of a substrate-based live cell functional imaging device. Biomed Microdevices 13: 291-301; Ahmed N, et al. (2011) Long-term in situ observation of barnacle growth on soft substrates with different elasticity and wettability. Soft Matter 7: 7281-7290; Schneider F, et al. (2009) Process and material properties of polydimethylsiloxane (PDMS) for Optical MEMS. Sensors and Actuators A: Physical 151: 95-99; Cheng C-M, et al. (2009) Probing cell structure by controlling the mechanical environment with cell-substrate interactions. Journal of Biomechanics 42: 187-192; Brown X Q, et al. J Y (2005) Evaluation of polydimethylsiloxane scaffolds with physiologically-relevant elastic moduli: interplay of substrate mechanics and surface chemistry effects on vascular smooth muscle cell response. Biomaterials 26: 3123-3129; and Gray D S, et al. (2003) Repositioning of cells by mechanotaxis on surfaces with micropatterned Young's modulus. Journal of Biomedical Materials Research Part A 66A: 605-614). This decreases the crosslink density, but is not ideal for a number of reasons. The first limitation of this approach is that the recommended 1:10 ratio is designed to optimize the stoichiometry of the cross-linking reaction. Reducing the relative amount of crosslinker increases the amount of free, non-crosslinked PDMS chains in the polymer matrix that are able to diffuse out of the bulk material. Because PDMS linear chains have lower surface energy than crosslinked PDMS, there is a driving force for the non-crosslinked PDMS to segregate to the surface of the bulk PDMS (Hillborg H, et al. (2004) Nanoscale hydrophobic recovery: A chemical force microscopy study of UV/ozone-treated cross-linked poly(dimethylsiloxane) Langmuir 20: 785-794). This results in the formation of an oil-like layer of oligomeric PDMS on the surface (Kim J-H, et al. (2010) Hydrophobically Recovered and Contact Printed Siloxane Oligomers for General-Purpose Surface Patterning. Langmuir 26: 13015-13019 and Feinberg A W, Brennan A B (2003) Effect of argon plasma treatment on PDMS elastomer investigated by AFM. Abstracts Of Papers Of The American Chemical Society 225: U711-U711) that can potentially disrupt cell adhesion and other processes (Wang L, et al. (2010) Chemical and physical modifications to poly(dimethylsiloxane) surfaces affect adhesion of Caco-2 cells. Journal Of Biomedical Materials Research Part A 93A: 1260-1271). The long-term consequence of cellular uptake of this oligomeric PDMS chains remains an unresolved area of concern. The second problem is that Sylgard 184 is filled with fumed silica, glassy nanoparticles that add significant stiffness to the polymer and accounting for 30 to 60 wt % of the cured polymer (Olah A, et al. (2005) Hydrophobic recovery of UV/ozone treated poly(dimethylsiloxane): adhesion studies by contact mechanics and mechanism of surface modification. Applied Surface Science 239: 410; Corporation DC (2011 Mar. 15) SYLGARD® 184 SILICONE ELASTOMER CURING AGENT MSDS No: 01015331; and Corporation DC (2010 May 3) SYLGARD® 184 SILICONE ELASTOMER KIT (BASE). MSDS No: 01064291). These nanoparticles are in both the base resin and curing agent, so reducing the curing agent content does not remove these nanoparticles. As a result, the decreased elastic modulus of the 1:70 Sylgard 184 requires an extremely low crosslink density and a large number of free chains to compensate for the stiff nanoparticles, exacerbating the problem of free oligomer chains highlighted above.

Researchers have also explored other approaches to control the crosslink density of PDMS. For example, trimethyl terminated PDMS oils have been incorporated into the PDMS while it is cured, which are unable to covalently crosslink via hydrosilation curing and thus decrease the crosslink density of the elastomer network (Feinberg A W, et al. (2003) Investigating the Energetics of Bioadhesion on Microengineered Siloxane Elastomers: Characterizing the Topography, Mechanical Properties, and Surface Energy and Their Effect on Cell Contact Guidance. In: Clarson, Fitzgerald, Owen, Smith, Dyke V, editors. Synthesis and Properties of Silicones and Silicone-Modified Materials: ACS. pp. 196-211). Using this strategy, the elastic modulus of Silastic T2, another silica-filled PDMS, was reduced to as low as ~800 kPa and the fact that the PDMS oils leached out was used to enhance the fouling release characteristics of the PDMS. Another approach used to modify crosslink density has been controlling the temperature and time at which Sylgard 184 has been cured. For example, varying the baking time from 15 minutes to 3 days and the curing agent from 3% to 10% enables tuning the elastic modulus of Sylgard 184 from 50 kPa to 4,000 kPa (Fuard D, et al. (2008) Optimization of polydi-methyl-siloxane (PDMS) substrates for studying cellular adhesion and motility Microelectronic Engineering 85: 1289-1293). While this is a large range, the soft PDMS continues to cure at room temperature and thus the mechanical properties are not stable with time.

This makes it problematic for cell culture studies where the PDMS will be placed in a 37° C. incubator for prolonged periods of time and the elastic modulus will increase. With the goal of spatially patterning the mechanical properties, Sun et al have developed an approach that uses benzophenone added to the Sylgard 184 as a photo initiator to reduce the crosslink density when exposed to UV light (Sun Y B, et al. (2012) UV-Modulated Substrate Rigidity for Multiscale Study of Mechanoresponsive Cellular Behaviors. Langmuir 28: 10789-10796). This can produce Sylgard 184 with an elastic modulus as low as 27 kPa when formulated with a base to curing agent ration of 30:1 and short curing times of 20 minutes at 110° C. Uniquely, the UV exposure also stabilizes the reduced crosslink density and thus the photosensitive PDMS mechanical properties do not change over time.

SUMMARY

Provided herein are polysiloxane blends that offer distinct advantages over previously reported methods to tune the elastic modulus of the polysiloxane compositions. The described polysiloxane system is advantageous because it provides a simple, robust platform for specifically varying elastic modulus without altering other surface properties, and the same micropatterning techniques can be used across the entire stiffness range.

The following are examples and are not intended to limit the scope of the disclosure.

Provided herein according to one embodiment is a sterile bioscaffold. The bioscaffold comprises a crosslinked mixture of a first composition comprising a polysiloxane and nanoparticles and a second composition comprising independently a polysiloxane and which does not comprise nanoparticles. According to one embodiment, the first composition is Sylgard 184 and the second composition is Sylgard 527. In one embodiment, the first composition further comprises polydimethyl siloxane, one or more siloxanes other than polydimethyl siloxane, and silica nanoparticles; and the second composition comprises one or both of a polydimethylsiloxane and a dimethyl, methylhydrogen siloxane. In other embodiments, the polysiloxane of the first and second compositions independently comprise one or more of a dimethyl siloxane; a diphenylsiloxane; a diethylsiloxane; a trifluoropropyl methyl siloxane; a phenylmethylsiloxane; a copolymer of dimethylsiloxane with one or more of a diphenylsiloxane, a diethylsiloxane, a trifluoropropyl methyl siloxane, and/or a phenylmethylsiloxane; and a aminopropylmethylsiloxane-(dimethylsiloxane). In one example, supporting, for example platinum-catalyzed hydrosilation crosslinking, one or both of the first composition and the second composition is dimethylvinyl-terminated. In one embodiment, the nanoparticles are silica nanoparticles, optionally fumed silica particles and optionally organically-modified silica, for example and without limitation comprising one or more vinyl and/or alkyl groups. In one example, the organically-modified silica comprises one or both of dimethylvinylated silica and trimethylated silica. In another exemplary embodiment, the first composition comprises dimethylvinyl-terminated dimethyl siloxane, dimethylvinylated and trimethylated silica, and tetra (trimethylsiloxy) silane, and the second composition comprises a polydimethylsiloxane and a dimethyl, methylhydrogen siloxane. According to certain embodiments, the bioscaffold is formed into a planar structure or a coating on a tissue culture vessel such as a plate, flask, hollow fiber, etc. and optionally can be formed into a three-dimensional structure, for example and without limitation, as a porous mass, a woven mass of fibers or a non-woven mass of fibers. The bioscaffold optionally comprises pores, e.g., to permit pass-through of tissue culture nutrients, gasses, waste, growth factors, etc.

The bioscaffold has a highly-tunable elastic modulus, ranging, for example and without limitation, from greater than 5 kPa to less than 1.72 MPa, 5 kPa and 50 kPa, or from about 50 kPa to about 1.34 MPa. This tunable elastic modulus can be achieved by varying the ratio of the first composition to the second, for example by the bioscaffold having a mass ratio of the first composition to the second composition of from 50:1 to 1:50, optionally from 5:1 to 1:10, or optionally about 1:10. The ratio of polysiloxane to nanoparticles in the composition, according to one non-limiting embodiment, the weight ratio of polysiloxane to nanoparticles is greater than that present in Sylgard 184, and in one embodiment is greater than 2.5, 3, 4, 5, 6, 7, 8, 9 and 10.

Therefore also provided is a sterile bioscaffold comprising a crosslinked mixture of a polysiloxane and nanoparticles in which a weight ratio of polysiloxane to nanoparticles is at least 2.5. This embodiment of the bioscaffold optionally comprises an ECM component deposited thereon, and the polysiloxane and nanoparticles are any embodiment of polysiloxane and nanoparticles as described herein in any combination, for example as described in this paragraph and below. Thus, as an example, the polysiloxane comprises one or more of a dimethyl siloxane; a diphenylsiloxane; a diethylsiloxane; a trifluoropropyl methyl siloxane; a phenylmethylsiloxane; a copolymer of dimethylsiloxane with one or more of a diphenylsiloxane, a diethylsiloxane, a trifluoropropyl methyl siloxane, and/or a phenylmethylsiloxane; and a aminopropylmethylsiloxane-(dimethylsiloxane) and/or the nanoparticle is an organically-modified silica and optionally an extracellular matrix (ECM) component deposited on a surface of the bioscaffold as described in this sunnuary and below.

According to one non-limiting embodiment, the polysiloxane in the bioscaffold is fully crosslinked (including as a class substantially and essentially fully crosslinked realizing that in reality it may not be possible to crosslink every polysiloxane molecule. Full crosslinking is achieved by including a sufficient amount of crosslinking compounds in the bioscaffold to achieve full crosslinking.

In certain non-limiting embodiments, an extracellular matrix (ECM) component is deposited on a surface of the bioscaffold and may be patterned on a surface of the bioscaffold. Non-limiting examples of ECM components include one or more of a glycosaminoglycan; a proteoglycan; a protein; and a glycoprotein, optionally one or more of a heparan sulfate, a dermatan sulfate, a chondroitin sulfate, a keratin sulfate, a hyaluronic acid, an aggrecan, a versican, a neurocan, a brevican, a decorin, a perlecan, a collagen, an elastin; a laminin, a fibronectin, a vitronectin, an osteopontin and a fibrinogen.

In certain non-limiting embodiments, the bioscaffold further comprises a cell deposited thereon, for example and without limitation, a stem cell, a corneal endothelial cell or a progenitor thereof; a muscle cell (skeletal, smooth or cardiac) or a progenitor thereof; a neuronal cell or a progenitor thereof, or a retinal pigment epithelial cell or a progenitor thereof.

Also provided is a cell culture device comprising a rigid or semi-rigid substrate, such as glass, plastic (polymeric) or any other suitable material for cell culture, onto which the bioscaffold in any embodiment described in this Summary and below is deposited. The cell culture device optionally comprises tissue culture media and a cell.

According to additional non-limiting embodiments, a method of manufacturing a cell culture device is provided. The method comprises preparing a bioscaffold according to any embodiment described in this Summary and below by mixing the first composition with the second composition and cross-linking the polysiloxane(s), by any effective mechanism, such as by hydrosilation. Prior to during or after cross-linking, the mixture or bioscaffold formed thereby is deposited onto a substrate that is suitable for cell culture. According to one embodiment, an ECM component as described in this Summary and below, is deposited onto the bioscaffold. The ECM component is optionally stamped onto the substrated in a pattern. According to one embodiment, a raised pattern of a stamp comprising the raised pattern is coated with an ECM component, and the ECM component is stamped onto the bioscaffold with the stamp, thereby depositing a pattern of the ECM component onto the bioscaffold.

Also provided herein is a method of growing cells or a cell construct. The method comprises placing (e.g., seeding) cells onto a bioscaffold as described in this Summary or below, and culturing the cells for a time period. In one embodiment, the cells are grown into a monolayer or tissue. Non-limiting examples of cells include: a stem cell, a corneal endothelial cell or a progenitor thereof; a muscle cell (skeletal, smooth or cardiac) or a progenitor thereof; a neuronal cell or a progenitor thereof, or a retinal pigment epithelial cell or a progenitor thereof.

According to another embodiment, a method of determining an effect of a chemical composition or a non-chemical treatment on a cell is provided. The method comprises culturing cells in tissue culture media on a bioscaffold as described in this Summary or below; exposing the cell to an environmental stimulus; and determining an effect of the exposure on the cell. Non-limiting examples of the cell include: a cancer cell, a stem cell or a progenitor cell. The environmental stimulus is according to certain embodiments a chemical composition, a non-chemical treatment, and/or a modification of a composition or a physical characteristic of the bioscaffold or applying a mechanical load to the scaffold.

Any aspect of the methods described herein can be automated.

In another embodiment, a kit is provided for production of a bioscaffold. The kit comprises a first composition and a second composition as described in this Summary and below. The kit optionally comprises a third composition that comprises an ECM component, nanoparticles for increasing the stiffness of a polysiloxane composition and/or one or both of a mold for molding the bioscaffold into a shape and a stamp comprising a raised pattern adapted for patterning the ECM component on a bioscaffold produced by the first and second composition. The first component, second component, ECM component, mold, stamp or any other feature of the kit is as described in this summary and below.

In another embodiment a method of increasing an elastic modulus of a cross-linked polysiloxane composition comprising adding nanoparticles to the polysiloxane composition during or prior to cross-linking and cross-linking the composition. A polysiloxane composition manufactured in this manner is expected to have elastic modulus of greater than 1.7 mPa and in other embodiments at least 2, 5, 10 or 20 MPa, for example and without limitation 10, 15 or 20 MPa. In this embodiment, the polysiloxane and nanoparticles are as described in this Summary and below. In one embodiment, the polysiloxane composition is Sylgard 184, as described herein. Associated with this method are bio-scaffolds, cell culture devices and kits comprising a composition prepared by the method and having an elastic modulus of than 1.7 mPa and in other embodiments at least 2, 5, 10 or 20 MPa, for example and without limitation 10, 15 or 20 MPa. Also provided are methods of making and using the higher-stiffness composition prepared by this method, including of determining an effect of a chemical composition or a non-chemical treatment on a cell, methods of growing cells or a cell construct, and methods of manufacturing a cell culture device essentially as described in any embodiment presented in this Summary and below but including the higher-stiffness polysiloxane composition or precursors thereof.

DETAILED DESCRIPTION

Figure 1:
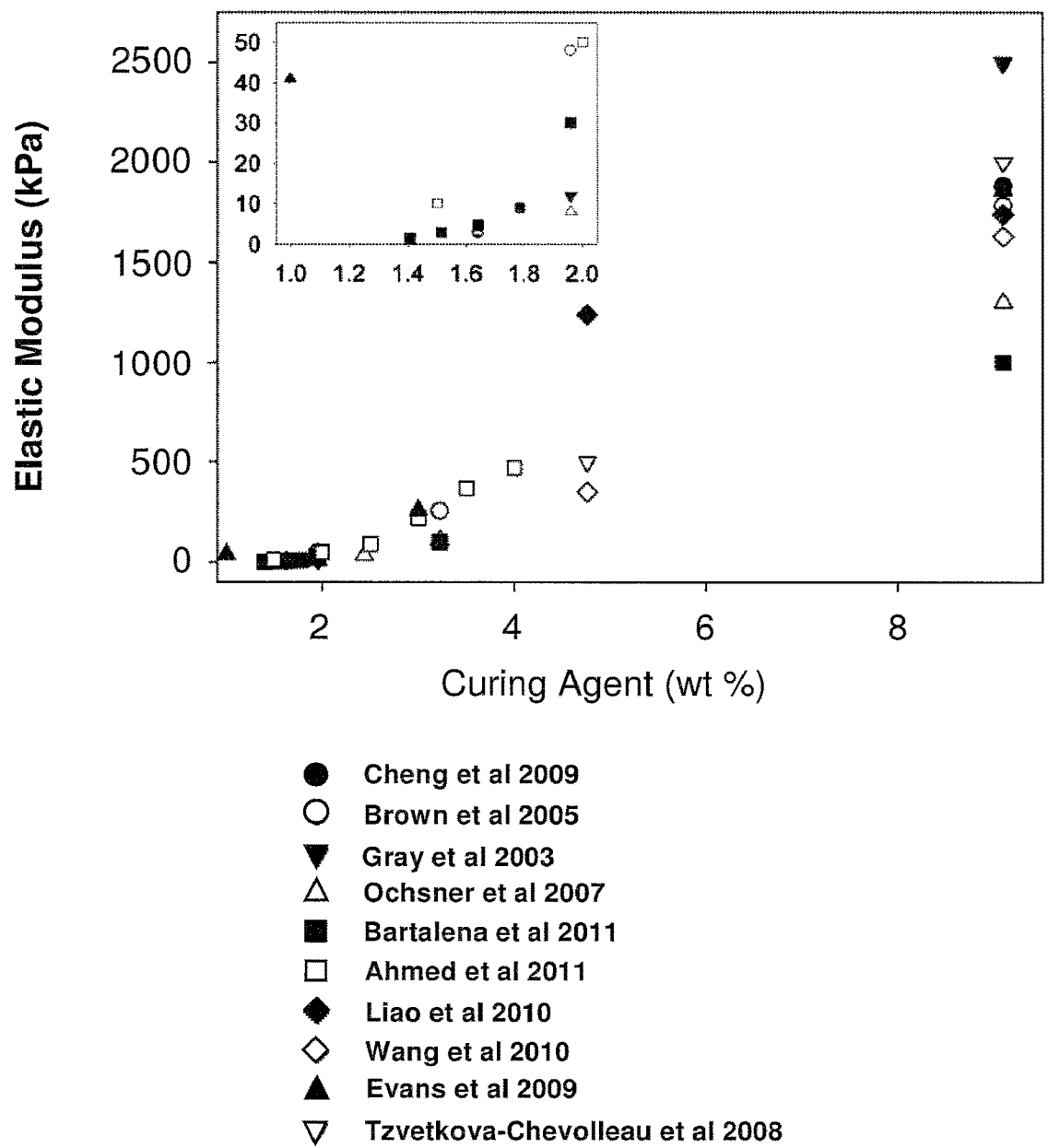
FIG. 1 is a summary plot of published values for the elastic modulus of Sylgard 184. In these examples the manufacturer's recommend ratio of curing agent to base has been reduced from 1:10 down to as low as 1:70 to vary the elastic modulus of the Sylgard 184. Variability of greater than 250% in the measured elastic modulus is observed at the commonly used ratios of 1:10, 1:20, 1:30 and 1:50. Values are included from: Cheng C-M, et al. (2009) Probing cell structure by controlling the mechanical environment with cell-substrate interactions. Journal Of Biomechanics 42: 187-192 (●), Brown X Q, et al. J Y (2005) Evaluation of polydimethylsiloxane scaffolds with physiologically-relevant elastic moduli: interplay of substrate mechanics and surface chemistry effects on vascular smooth muscle cell response. Biomaterials 26: 3123-3129 (○), Gray D S, et al. (2003) Repositioning of cells by mechanotaxis on surfaces with micropatterned Young's modulus. Journal of Biomedical Materials Research Part A 66A: 605-614 (▼), Ochsner M, et al. (2007) Micro-well arrays for 3D shape control and high resolution analysis of single cells. Lab On A Chip 7: 1074-1077 (Δ), Bartalena G, et al. (2011) A novel method for assessing adherent single-cell stiffness in tension: design and testing of a substrate-based live cell functional imaging device. Biomed Microdevices 13: 291-301 (■), Ahmed N, et al. (2011) Long-term in situ observation of barnacle growth on soft substrates with different elasticity and wettability. Soft Matter 7: 7281-7290 (□), Liao Q, et al. (2010) A hybrid model to determine mechanical properties of soft polymers by nanoindentation. Mechanics of Materials 42: 1043-1047 (♦), Wang L, et al. (2010) Chemical and physical modifications to poly(dimethylsiloxane) surfaces affect adhesion of Caco-2 cells. Journal Of Biomedical Materials Research Part A 93A: 1260-1271 (◇), Evans N D, et al. (2009) Substrate Stiffness Affects Early Differentiation Events In Embryonic Stem Cells. European Cells and Materials 18:1-14 (▲) and Tzvetkova-Chevolleau T, et al. (2008) The motility of normal and cancer cells in response to the combined influence of the substrate rigidity and anisotropic microstructure. Biomaterials 29: 1541-1551. The inset shows the elastic modulus for curing agent to base ratios of 1:50 to 1:100, note the variability of greater than 500% at the commonly used value of 1:50 (~2 weight percent curing agent).

Other than in the operating examples, or where otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements. Furthermore, when numerical ranges of varying scope are set forth herein, it is contemplated that any combination of these values inclusive of the recited values may be used.

Also, it should be understood that any numerical range recited herein is intended to include all sub-ranges subsumed therein. For example, a range of "1 to 10" is intended to include all sub-ranges between and including the recited minimum value of 1 and the recited maximum value of 10, that is, having a minimum value equal to or greater than 1 and a maximum value of equal to or less than 10.

For definitions provided herein, those definitions refer to word forms, cognates and grammatical variants of those words or phrases.

As used herein, the terms "comprising," "comprise" or "comprised," and variations thereof, are meant to be open ended. The terms "a" and "an" are intended to refer to one or more.

As used herein, the term "patient" or "subject" refers to members of the animal kingdom including but not limited to human beings and "mammal" refers to all mammals, including, but not limited to human beings.

A biodegradable polymer is "biocompatible" in that the polymer and degradation products thereof are substantially non-toxic to cells or organisms, including non-carcinogenic and non-immunogenic, and are cleared or otherwise degraded in a biological system, such as an organism (patient) without substantial toxic effect. Non-limiting examples of degradation mechanisms within a biological system include chemical reactions, hydrolysis reactions, and enzymatic cleavage. A polymer is "biodegradable" if it degrades over time in a biological system, such as when implanted in a patient. Suitable biodegradation rates for implanted cell constructs typically range from days to months, e.g., from one day to 12 months including increments therebetween, typically in order to permit and facilitate adequate integration of the implanted cells or tissue in a patient.

As used herein, the term "polymer composition" is a composition comprising one or more polymers. As a class, "polymers" includes, without limitation, homopolymers, heteropolymers, co-polymers, block polymers, block co-polymers and can be both natural and synthetic. Homopolymers contain one type of building block, or monomer, whereas co-polymers contain more than one type of monomer.

A polymer "comprises" or is "derived from" a stated monomer if that monomer is incorporated into the polymer. Thus, the incorporated monomer that the polymer comprises is not the same as the monomer prior to incorporation into a polymer, in that at the very least, certain terminal groups are incorporated into the polymer structure. A polymer is said to comprise a specific type of linkage if that linkage is present in the polymer.

As described herein, a "fiber" an elongated, slender, thread-like and/or filamentous structure. A "matrix" is any two- or three-dimensional arrangement of elements (e.g., fibers), either ordered (e.g., in a woven or non-woven mesh) or randomly-arranged (as is typical with a mat of fibers typically produced by electrospinning) and can be isotropic or anisotropic.

In one embodiment, described herein a bioscaffold is provided. A bioscaffold refers to a biocompatible structure on which cells can survive, grow and/or propagate, in vitro or in vivo. A bioscaffold is sterilized prior to contact with or seeding with cells or use in vivo or in any biological system. The bioscaffold comprises one or more crosslinked polysiloxanes and nanoparticles contributing to an elastic modulus of the bioscaffold. The proportion of nanoparticles relative to the polysiloxane dictates the elastic modulus of the bioscaffold, with a weight ratio of polysiloxane to nanoparticles of at least 2.5, in one embodiment at least 3, and in another embodiment, about 5. Thus, in one aspect, the bioscaffold is tunable in that it comprises a mixture of a first composition and a second composition in various proportions. The first composition comprises a polysiloxane and a nanoparticle, while the second composition comprises a polysiloxane with a different elastic modulus such that varying proportions of the first composition having a first elastic modulus and the second composition, having a second elastic modulus, different from the first, results in a composition that has an elastic modulus between the first and second elastic modulus depending on the relative proportion for the first and second composition in the bioscaffold. In another aspect, the elastic modulus of the bioscaffold is tunable by varying an amount of the nanoparticles in the composition.

In all examples, the composition is cross-linked by any useful method. For example, in hydrosilation, an olefinic group, e.g., a vinyl group in a vinyl-terminated polysiloxane is crosslinked to an —Si—H group in the presence of a platinum catalyst. According to one non-limiting embodiment, the bioscaffold is prepared by cross-linking a mixture of: a first composition comprising one or more polysiloxanes, such as a polydimethyl siloxane, one or more siloxanes other than the polysiloxane, and silica nanoparticles; and a second composition that does not comprise a silica nanoparticle (that is, essentially and substantially silica nanoparticle-free) comprising a polysiloxane, such as one or both of a polydimethylsiloxane and a dimethyl, methylhydrogen siloxane. In certain embodiments, the silica nanoparticles comprises fumed silica particles. The silica nanoparticles optionally comprise organically-modified silica (e.g., an ORMOSIL), that optionally comprises one or more vinyl and/or alkyl (e.g., $C_{1-3}$ alkyl) groups, such as, for example and without limitation, dimethylvinylated silica and trimethylated silica. One or more of the siloxanes, such as the dimethylsiloxane and/or dimethyl, methylhydrogen siloxane is dimethylvinyl-terminated. In one exemplary embodiment, the first composition comprises dimethylvinyl-terminated dimethyl siloxane, dimethylvinylated and trimethylated silica, and tetra(trimethylsiloxy) silane, and the second composition comprises a polydimethylsiloxane and a dimethyl, methylhydrogen siloxane. According to certain non-limiting embodiments, the compositions have an elastic modulus ranging from greater than 5 kPa to less than 1.72 MPa, or optionally from about 50 kPa to about 1.34 MPa. According to certain non-limiting embodiments, the compositions have a mass ratio of the first composition to the second composition of from 50:1 to 1:50, optionally 5:1 to 1:10, or optionally about 1:10. Lower elastic modulus compositions can be prepared by reducing cross-linking, though that could result in some soluble polymer. Likewise addition of nanoparticles, such as fused silica particles, to a polysiloxane-containing composition such as Sylgard 184 can be used to further increase the elastic modulus, e.g., to an elastic modulus greater than the elastic modulus of Sylgard 184, which is approximately 1.7 MP, for example and without limitation in the range greater than 1.7, 1.8, 2, 5, 10 or 20 MPa, for example and without limitation 10, 15 or 20 MPa. Further, addition or benzophenone would be expected to lower the elastic modulus of the composition. In one embodiment, the composition is fully cross-linked meaning the siloxanes are substantially, essentially or completely cross-linked to prevent (substantially, essentially or completely) leaching of siloxane from the composition when in solution within acceptable tolerances.

As described below, in certain embodiments an extracellular matrix (ECM) component is deposited (adsorbed, absorbed or covalently linked) on a surface of the bioscaffold. According to one non-limiting embodiment, the ECM component is patterned on a surface of the bioscaffold, meaning it is non-uniformly deposited onto the PDMS material in a defined pattern. Non-limiting embodiments of the ECM component comprise one or more of: a glycosaminoglycan, e.g., a heparan sulfate, a dermatan sulfate, a chondroitin sulfate, a keratin sulfate, a hyaluronic acid; a proteoglycan, e.g., an aggrecan, a versican, a neurocan, a brevican, a decorin, and a perlecan; a collagen, e.g., a Type I, IV or VIII collagen; an elastin; a laminin; a fibronectin; a vitronectin; an osteopontin; and a fibrinogen. ECM components, such as collagens, fibronectins, laminins, decellularized ECM, etc. are commercially available from a large variety of sources, including without limitation, Sigma-Aldrich of St. Louis Mo. and BD Biosciences of San Jose, Calif. Of note, various ECM components and ratios thereof are specific to certain tissues. For example aggrecan is a major cartilage ECM component, while brevican is a developmentally regulated chondroitin sulfate proteoglycan that is found in the brain. Choice of a suitable ECM component may be made with respect to the tissue origin of the cells. This is not required, and it may be found that certain types of cells will propagate best on ECM components or combinations thereof that may be different in composition that what is natively found in the tissue origin of the cultured cells.

In one non-limiting embodiment of the first composition, Sylgard 184 is a silicone elastomer comprising a polydimethyl siloxane and an organically-modified silica (e.g., ORMOSIL). Sylgard 184 is prepared by combining a base (Part A) with a curing agent (Part B). The base includes a siloxane (dimethylvinyl-terminated dimethyl siloxane) and an ORMOSIL (dimethylvinylated and trimethylated silica) in a solvent (ethyl benzene). The curing agent also includes a mixture of siloxanes and an ORMOSIL in a solvent, including: dimethyl, methylhydrogen siloxane; dimethylvinyl-terminated dimethyl siloxane; dimethylvinylated and trimethylated silica; tetramethyl tetravinyl cyclitetra siloxane; and ethyl benzene. In one non-limiting embodiment of the second composition, Silgard 527 is a silicone (dimethyl siloxane) elastomer gel that is substantially similar to Sylgard 184, but excludes the ORMOSIL component. It also is prepared from a base and a curing agent. A large variety of useful siloxane compositions are commercially available, for example, from Gelest, Inc. of Morrisville, Pa.

A siloxane is a compound having one or more Si—O—Si linkages, e.g.,

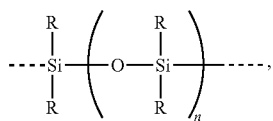

where R are independently organic groups or H, and n typically varies from 1-2000, with an average molecular weight (Mw) of, for example, about 1000 to about 25,000 and increments therebetween. For polysiloxanes, n>1. Non-limiting examples of polysiloxanes include methylhydrogensiloxane: e.g.,

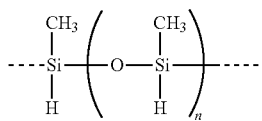

and polydimethylsiloxane (PDMS): e.g.,

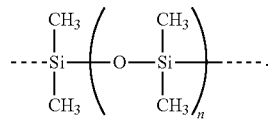

Combination siloxanes include methylhydrogen, dimethyl-siloxane, which includes a mixture of both methyhydrogensiloxyl and dimethylsiloxyl groups. In siloxanes, organic groups, such as without limitation, alkyl, haloalkyl, aryl, haloaryl, alkoxyl, aralkyl and silacycloalkyl groups, and/or more reactive groups, such as alkenyl groups such as vinyl, allyl, propenyl, butenyl, pentenyl, hexenyl, heptenyl, octenyl, nonenyl and/or decenyl groups may be attached to silicon atoms of the siloxane backbone in any combination. Polar groups, such as acrylate, methacrylate, amino, imino, hydroxy, epoxy, ester, alkyloxy, isocyanate, phenolic, polyurethane oligomeric, polyamide oligomeric, polyester oligomeric, polyether oligomeric, polyol, and carboxypropyl groups may be attached to silicon atoms of the siloxane backbone in any combination and in combination with any groups described herein. Siloxanes may be terminated with any useful group, for example and without limitation, alkenyl, and/or alkyl groups, such as a methyl, ethyl, isopropyl, n-propyl and/or vinyl group or combinations thereof. Other groups that may be used to terminate a siloxane include: acrylate, methacrylate, amino, imino, hydroxy, epoxy, ester, alkyloxy, isocyanate, phenolic, polyurethane oligomeric, polyamide oligomeric, polyester oligomeric, polyether oligomeric, polyol, carboxypropyl, and halo, e.g., fluoro groups.

Nanoparticles are particles ranging from 1-999 nm (nanometers) in diameter and typically from 1-100 nm. Non-limiting examples of nanoparticles useful in the compounds and methods described herein include: silica nanoparticles, including, fused silica nanoparticles, organically-modified silica particles (e.g., ORMOSILs). Organically-modified silica particles are silica particles that are modified with organic groups, such as hydrocarbon groups, typically on their surface. The organic groups that may be linked to the silica nanoparticles include, without limitation hydrocarbons. Although the organic groups may be complex organic moieties, for example fluorescent groups, (co)polymers and oligomers, nucleic acids, etc., in the context of the methods described herein, and commonly-available compositions useful in the described compositions, devices and methods, such as Sylgard 184, the organic groups of the organically-modified silica particles described herein are typically aliphatic $C_{1-6}$ compounds, such as, without limitation: vinyl groups, alkyl groups, for example $C_{1-3}$ alkyl groups such as methyl, ethyl and isopropyl and n-propyl; and mono-, di-, and tri-alkylvinyl groups, for example $C_{1-3}$ alkylvinyl. The organically-modified silica particles may comprise one or more different groups on the same particle, and different organically-modified silica particles may be mixed together. In one example, e.g., that of Sylgard 184, the organically-modified silica particles include dimethylvinylated silica and trimethylated silica. Additional non-limiting examples of nanoparticles that are incorporated into the composition in certain embodiments include: polystyrene nanoparticles, latex nanoparticles, carbon black nanoparticles, aluminum oxide, nanoparticles, ceramic nanoparticles and metal nanoparticles, such as colloidal gold nanoparticles.

Certain combinations of PDMS substrate and ECM components may be optimal for growth of certain cell types. For example and without limitation, the combination of Sylgard 184 and Sylgard 527 in a ratio that achieves an elastic modulus of 50 kPa (e.g, a 1:10 ratio of Sylgard 184 to Sylgard 527), coated with collagen type IV, is a superior bioscaffold for expanding (propagating and passaging) mature corneal endothelial cells. Specifically, the cells maintain a normal corneal endothelial cell phenotype and do not become senescent, do not de-differentiate into a fibroblast-like cell and do not undergo and endothelial to mesenchymal transition.

In use, cells are cultured on any embodiment of the bioscaffold described herein. Generally, any bioscaffold described herein is immersed in suitable tissue culture media and then single cells, cells dissociated from tissue or pieces of tissue are seeded (placed, distributed, etc.) onto the bioscaffold and/or in the tissue culture media, and then are cultured in an incubator at a suitable temperature (e.g., 37° C.) and atmosphere (e.g., >95% relative humidity and/or 5% $CO_2$) for a length of time suitable to achieve a desired end-point. Where the cells are used for testing a chemical compound the length of time the cells are cultured typically would be anywhere from one hour to one week, including any increment therebetween. Where the cells are used for producing tissue in a regenerative medicine capacity, such as preparing corneal endothelium tissue, the cells typically would be cultured for from 3-4 days to 2-3 months, the end point being the production of a suitable cellular construct for the intended purpose.

The cells that may be seeded onto on the bioscaffold include, without limitation, stem cells, progenitor (precursor) cells, smooth muscle cells, skeletal myoblasts, myocardial cells, endothelial cells, endothelial progenitor cells, bone-marrow derived mesenchymal cells, neural cells, glial cells, and neuronal and glial progenitor cells, chondrocytes and progenitors thereof, osteogenic cells (e.g., osteoclasts) and progenitors thereof, and genetically modified cells. In certain embodiments of the genetically-modified cells, the genetically modified cells are capable of expressing a therapeutic substance, such as a growth factor. Examples of suitable growth factors include angiogenic or neurotrophic factor, which optionally may be obtained using recombinant techniques. Non-limiting examples of growth factors include basic fibroblast growth factor (bFGF), acidic fibroblast growth factor (aFGF), vascular endothelial growth factor (VEGF), hepatocyte growth factor (HGF), insulin-like growth factors (IGF), transforming growth factor-beta pleiotrophin protein, midkine protein. A large variety of genetically modified cells that might be grown on the bioscaffold grown herein, and the methods of making and using those cells are known or can be developed readily by an ordinary artisan.

As a class, stein cells and progenitor cells are cells that are capable of differentiation into another cell type, such as another progenitor cell or a fully differentiated, mature cell, for example and without limitation, a somatic cell, that has characteristic morphology and specialized functions. Stem cells are found in all multi-cellular organisms. Through mitotic cell division, they have the capacity to self-renew and can differentiate into a diverse range of specialized cell types. Mammalian stem cells include as a class: embryonic stem cells, adult stem cells, and cord blood stem cells. Embryonic Stem cells are derived from the inner cell mass of pre-implantation embryos. Adult stem cells are found in adult tissue. Cord blood stem cells are derived from the umbilical cord, which is rich in hematopoietic stem cells— stem cells that can differentiate to form all cellular components of blood.

Embryonic Stem cells are pluripotent. They are able to differentiate into all of the somatic cell types of the three primary germ layers: the ectoderm, the mesoderm and the endoderm, and. Embryonic Stem cells differentiate into the different cell types in the adult body. Absent stimulation to differentiate, embryonic Stem cells can expand indefinitely, maintaining pluripotency.

Adult stem cells also can self-renew indefinitely; however, unlike embryonic stein cells, are not pluripotent. They are multipotent in that they can differentiate into some, but not all mature cell types that have characteristic morphologies and specialized functions. Recent studies have shown that adult stem cells have a degree of plasticity and can be encouraged to differentiate into other cell lineages, a process also known as transdifferentiation. A non-exhaustive and non-limiting list of adult stem cells includes: mammary, intestinal, mesenchymal, endothelial, neural, olfactory, neural crest and testicular stem cells (adult germline stein cells. Exceptions to the lack of pluripotency of adult stem cells include non-embryonic cell types know as "Blastomere Like Stein Cells" (BLSCs) and "very small embryonic like" (VSEL) stein cells, which, though dormant, exhibit pluripotency (See, e.g., WO 2007100845).

Typically, stem cells generate an intermediate cell type or types before they achieve their fully differentiated state. The intermediate cell is called a precursor or progenitor cell. Progenitor or precursor cells in fetal or adult tissues are partly differentiated cells that divide and give rise to differentiated cells. Such cells are usually regarded as "committed" to differentiating into one or more further differentiated cell types along a particular cellular development pathway, but there are exceptions. Although they can differentiate into one or more cell types, unlike adult stein cells, adult progenitor cells cannot renew indefinitely, though they typically can retain their multipotency for several rounds of cell division.

Corneal endothelial cells useful in the constructs described herein may be derived from a patient's mature corneal endothelial cells, for example from a damaged corneal endothelium, or from suitable progenitors thereof, or a donor cornea or stein cells. (See, e.g., Peh et al (2011) Human Corneal Endothelial Cell Expansion for Corneal Endothelium Transplantation: An Overview. *Transplantation* PMID: 21358368 Doi 10.1097/Tp.0b013e3182111f01 and Proulx and Brunette (2012) Methods being developed for preparation, delivery and transplantation of a tissue-engineered corneal endothelium. Experimental Eye Research PMID: 21723281 DOI: 10.1016/j.exer.2011.06.013, both discussing transplant with a patient's own mature cells or donor cells, and Ju et al (2012), Derivation of corneal endothelial cell-like cells from rat neural crest cells in vitro. PLoS one. PMID: 22860120 DOI: 10.1371/journal.pone.0042378, discussing deriving stem cells from progenitor cells).

Neuronal cells, glial cells, progenitors thereof or stem cells may be used in the preparation of neuronal cell constructs. Examples of potentially useful stem cells include, for example and without limitation, astrocytes, neuronal stem cells, glial progenitor cell, parenchymal glial progenitor cell, pluripotent stem cells, induced pluropotent stem cells, embryonic stem cells, adipose-derived stem cells (See, e.g., Young, Robin R. (2012) Adult Stem Cell Fact Sheet, NY stem cell summit; Schmidt, C E et al., "NEURAL TISSUE ENGINEERING: Strategies for Repair and Regeneration", *Annu. Rev. Biomed. Eng.* 2003. 5:293-347 and generally, StemBook, Harvard Stem Cell Institute, Massachusetts General Hospital (2011) (www.stembook.org) and also euroStemCell web-site (www.eurostemcell.org).

Retinal pigment epithelial (RPE) cells are a critical component of the retina and their function is required for survival of the light-sensitive rods and cones. Many debilitating eye diseases, such as macular degeneration, are characterized by loss of RPE cells and subsequent loss of these photoreceptors. Adult human RPE cells have been difficult to culture in vitro due to loss of phenotype. Specifically, the RPE cells appear to undergo an epithelial to mesenchymal transition (EMT). For this reason adult human RPE cells are not routinely cultured even though they are the cell type of primary interest. Instead, fetal human RPE cells are used, which better maintain phenotype in culture. In addition, RPE cells can be differentiated from pluripotent stem cells, such as human ES cells and iPS cells. (See, e.g., Blenkinsop et al. The Culture and Maintenance of Functional Retinal Pigment Epithelial Monolayers from Adult Human Eye, in Scott H. Randell and M. Leslie Fulcher (eds.), Epithelial Cell Culture Protocols: Second Edition, Methods in Molecular Biology, vol. 945, DOI 10.1007/978-1-62703-125-7_4, © Springer Science+Business Media, LLC 2012, Chapter 4; Zhang, Y, et al. (2012) Derivation, culture and retinal pigment epithelial differentiation of human embryonic stem cells using human fibroblast feeder cells, *J Assist Reprod Genet* (2012) 29:735-744 DOI 10.1007/s10815-012-9802-2; Kuznetsova et al (2011) (Human Adult Retinal Pigment Epithelial Cells as Potential Cell Source for Retina Recovery" *Cell and Tissue Biology* 5(5):495-502; and Kokkinaki, M et al., (2011) Human iPS-derived retinal pigment epithelium (RPE) cells exhibit ion transport, membrane potential, polarized VEGF secretion and gene expression pattern similar to native RPE *Stem Cells*. 29(5):825-835. doi:10.1002/stem.635, for description of useful methods for culturing/producing RPE). Using the methods of manufacturing and for tailoring the elastic modulus and ECM coatings for the bioscaffold provided herein, it is expected that optimal conditions for RPE cultivation will be ascertainable.

In a further embodiment, the bioscaffold described herein is deposited (coated, sprayed, attached, layered, overlaid, rinsed, placed, pressed, poured, spin coated etc.) onto a surface of a tissue culture vessel, including, without limitation, a flask, a tissue culture dish or plate, a multi-well plate, tubes, hollow fibers, bottles, cover slips etc. For example, a cell culture device is provided, such as a rigid or semi-rigid substrate, such as glass or a polymer, e.g., a polystyrene or polycarbonate. Optionally an ECM component, such as collagen IV, elastin, laminin, and fibronectin, is then deposited or patterned onto the bioscaffold and the surface is dried. Cells can then be cultured on the bioscaffold as described herein. Provided therefore, is labware, such as cell culture devices and disposable products coated with any embodiment of the bioscaffold described herein.

In one embodiment, the compositions described herein are provided as part of a kit. In one embodiment, the kit comprises a composition comprising polydimethyl siloxane and silica nanoparticles and a curing agent therefor; and a second composition that does not comprise a silica nanoparticle comprising one or both of a polydimethylsiloxane and a dimethyl, methylhydrogen siloxane and a curing agent therefor. The kit optionally comprises a third composition that comprises an ECM component that may be deposited or patterned onto the PDMS once it is cured. The kit also optionally comprises one or both of a mold for molding (casting, etc.) the bioscaffold into a shape. The stamp comprises a raised pattern adapted for patterning the ECM component on a bioscaffold produced by the first and second composition. The components of the kit are packaged in any packaging suitable for shipping and storage of the components of the kit, such as, for example: boxes, containers, bottles, vials, test tubes, plastic wrap, foil, etc. as are apparent to one of ordinary skill.

The bioscaffolds may be molded into any useful shape. For production of corneal endothelium, the bioscaffold is coated onto a flat or appropriately curved surface. For nerve growth or muscle growth, the bioscaffold may be formed into a channel or tube. In one embodiment, a bioscaffold is prepared according to any embodiment described herein, and includes pores to permit permeation of gasses and nutrients to cells cultured on the substrate.

The compositions described herein can be manufactured on a micron or nanometer scale. Structures containing microwells or other micro- or nano-scale features can be produced using microtechnology, including micromolding and microfluidic methods. According to one embodiment in which an array of microwells is produced, a template is produced on a silicon wafer, such as a pattern of microwell-sized protuberances, and any bioscaffold composition described herein is then coated onto the wafer and cured. Once cured, the bioscaffold is then peeled from the wafer and optionally the microwells are coated with an ECM component as described herein. One nonlimiting example of a method of manufacturing such microwells is provided in Mi et al., ((2006) "Micromolding of PDMS scaffolds and microwells for tissue culture and cell patterning: A new method of microfabrication by the self-assembled micropatterns of diblock copolymer micelles" Polymer 47:5124-5130).

Any of the bioscaffold compositions described herein can be fabricated to include micro- or nano-scale features, such as wells, protuberances and pores. For example, to produce a structure producing precise and controlled cell guidance, MEMS (microelectromechanical systems), NEMS (nanoelectromechanical systems), microtechnology and nanotechnology strategies are applied. These technologies produce bioscaffolds that closely parallel the multidimensional size scale of living cells, and therefore might be used to produce bioscaffolds that include topographical, spatial, and chemical properties to optimize control over cell behavior. MEMS microfabrication and micromachining techniques is used to create two dimensional (2D) substrates with surface topography with defined dimensions and distributions, such as posts and channels. Fabrication of microscale and nanoscale PDMS structures is possible using standard MEMS techniques, such as soft lithography techniques that do not require a clean room and photolithography techniques (See, e.g., Khademhosseini et al. (2006) Microscale technologies for tissue engineering and biology Proc. Nat'l. Acad. Sci. 103(8):2480-2487; Mata et al. (2005) Materials Research Society Symposium Proceedings. Volume 845 Nanoscale Materials Science in Biology and Medicine, Held in Boston, Mass. on 28 Nov.-2 Dec. 2004, pp. 97-103; and Mi et al. (2006) Polymer 47:5124-5130, and the Examples below, providing examples of methods for manufacturing micropatterns in the bioscaffold and for use in patterning ECM components or other compositions on the bioscaffold). As an example, Mi et al., described patterns for single cell microwells, facilitating production of cell structures with an exceptionally high level of detail ((2006) Polymer 47:5124-5130). Cells may be deposited in precise patterns in a micropatterned bioscaffold by microfluidic methods, or if all deposited cells are to be the same, by placing the bioscaffold in culture medium, depositing the cells and culturing the cells. According to one embodiment, microscale-organized three-dimensional structures are manufactured by producing microscale-engineered layers and folding or rolling those layers and/or overlaying multiple layers. In this manner, detailed structures, such as pancreatic islets or liver tissue can be produced by micropatterning and constraining movement of specific cell types. Incorporation of benzophenone into the described composition may enable photolithographic spatial patterning of PDMS stiffness.

Other forms that the bioscaffold may take include, without limitation: a porous mass, a woven mass of fibers or a non-woven mass of fibers. Fibers may be prepared, for example by extrusion, drawing, spraying, electro spraying, electrospinning, etc.

In one embodiment, a bioscaffold described herein is plasma treated, or oxidizing by exposure to ozone to make the substrate more hydrophilic, which may be desirable in certain circumstances. In one embodiment, the bioscaffold is exposed to an $Ar/O_2$-based plasma, rendering the surface of the bioscaffold more hydrophilic (See, e.g., Fuard, D., et al. (2008) Microelectronic Engineering 85, 5-6 (2008) 1289-1293). In another embodiment, the bioscaffold is exposed to UV-generated ozone, rendering the surface of the bioscaffold more hydrophilic.

Microfabrication methods also may be used to pattern one or more ECM components and/or other active agents, such as growth factors. For example and without limitation, therapeutic agents may be deposited on the bioscaffold, such as antimicrobial agents chosen from one or more of: isoniazid, ethambutol, pyrazinamide, streptomycin, clofazimine, rifabutin, fluoroquinolones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, and silver salts such as chloride, bromide, iodide and periodate. Optionally, one or more growth factors can be deposited or patterned onto the bioscaffold, for example and without limitation: basic fibroblast growth factor (bFGF), acidic fibroblast growth factor (aFGF), vascular endothelial growth factor (VEGF), hepatocyte growth factor (HGF), insulin-like growth factors 1 and 2 (IGF-1 and IGF-2), platelet derived growth factor (PDGF), stromal derived factor 1 alpha (SDF-1 alpha), nerve growth factor (NGF), ciliary neurotrophic factor (CNTF), neurotrophin-3, neurotrophin-4, neurotrophin-5, pleiotrophin protein (neurite growth-promoting factor 1), midkine protein (neurite growth-promoting factor 2), brain-derived neurotrophic factor (BDNF), tumor angiogenesis factor (TAF), corticotrophin releasing factor (CRF), transforming growth factors α and β (TGF-α and TGF-β), interleukin-8 (IL-8), granulocyte-macrophage colony stimulating factor (GM-CSF), interleukins, and interferons.

In one non-limiting embodiment, ECM components and active agents—for example as described herein—are microcontact printed onto the PDMS substrates using an adaptation of previously reported techniques (Feinberg A W, et al. (2010) Surface-Initiated Assembly of Protein Nanofabrics. Nano Letters 10:2184-2191). Briefly, a desired pattern is designed using CAD software and printed onto a transparency-based photomask. Glass wafers are spincoated with photoresist, for example SPR 220.3 positive photoresist (Microchem, Newton Mass.), and are exposed to UV light through the transparency-based photomask, developed using developer, for example MF-319 developer (Microchem) and post baked, for example at 115° C. for 90 seconds. PDMS stamps for microcontact printing are prepared by mixing a PDMS composition, such as Sylgard 184, pouring the prepolymer over the patterned glass wafers and curing the polymer. Once cured, the PDMS is peeled from the wafer and optionally cut into a desired and useful size. The stamp is then washed and sterilized and, if necessary dried, for example the stamp is sonicated in 50% ethanol for 30 minutes and dried using a nitrogen gun. The ECM component and/or active agent is then applied to the stamp, for example by coating the stamp with a solution or gel comprising the active agent and optionally rinsing and drying the solution or gel. The bioscaffold is then stamped with the ECM component or active agent by placing the stamp patterned side down on the bioscaffold, and then the stamp is removed, leaving behind the patterned protein. According to one embodiment, the stamp is less attractive to the coating than the bioscaffold ensuring full transfer of the coating from the stamp to the bioscaffold.

Cell constructs may be manufactured in multiple ways using the bioscaffolds described herein. In one embodiment, cells are grown on a bioscaffold prepared according to any embodiment described herein, and the cells, along with the bioscaffold adhered thereto, are implanted still attached to the bioscaffold. Because PDMS compositions typically are resistant to degradation in vivo, in one embodiment, the bioscaffold is porous in order to permit transfer of nutrients, gasses, etc. to and from the cell construct. In one non-limiting example, a porous and thin, e.g., ranging from 5 μm to 500 μm in thickness, less than 100 μm in thickness, or about 20 μm in thickness bioscaffold having a composition described herein is used as a cell growth bioscaffold. The bioscaffold is placed in suitable cell culture media and corneal endothelial cells are propagated on the bioscaffold to form a monolayer. The bioscaffold is optionally adhered to a substrate, such as a glass disc, using a dissolvable polymeric composition, such as a reverse phase hydrogel that dissolves at temperatures lower than the cell culture temperature, e.g., 37° C. This process is described in Examples 3 and 4, below. The combined bioscaffold and cell monolayer are then implanted in a patient's eye. So long as the bioscaffold is substantially uniform in thickness, within tolerances, and Because the PDMS bioscaffold is transparent, and so long as the bioscaffold is optically neutral, that is, it does not introduce refractive errors, it will be acceptable for transplantation.

One aspect of the methods described herein are that cells, such as corneal endothelial cells, can be passaged a number of times without loss of their phenotype. As a consequence, healthy corneal endothelial cells can be obtained from a patient, for instance from corneal endothelium of a patient, or from a donor cornea that is suitable or unsuitable for transplant, or a biopsy and enough cells can be produced to assemble a monolayer on a biodegradable bioscaffold, such as a gel comprising a naturally-derived polymer (a polymer that can be either processed from tissue or which can be found in tissue, but which is synthesized artificially) such as a collagen, e.g., collagen type I gels, fibrin gels, gelatin, vitrigel, silk fibroin, chitosan, and/or decellularized extracellular matrix (ECM); an elastomer comprising a synthetic polymers, such as a poly(ester urethane) urea elastomer (PEUU) or a poly(ether ester urethane) urea elastomer (PEEUU); or a gel comprising mixtures of one or more naturally-derived polymer, such as a collagen, a fibrin, or decellularized ECM with a synthetic polymer, such as one or both of PEUU or PEEUU.

Once a sufficient quantity of corneal endothelial cells are produced by propagation on the PDMS bioscaffold described herein, they can be enzymatically detached from the PDMS bioscaffold, e.g., by standard trypsinization methods, and then seeded onto the biodegradable bioscaffold to assemble into an intact corneal endothelium. The biodegradable bioscaffold seeded with the cells is then implanted in a patient's eye. The seeded bioscaffold is optionally cultured in vitro for a period of time prior to implantation. Although this process is described in the context of corneal endothelium, it is applicable to any cell type.

Also provided herein is a method of growing (including both propagating or maintaining at least a portion of the cells). The method comprises seeding cells onto a bioscaffold as described herein and culturing the cells for a time period, such as a time period sufficient to achieve a desired end-point, such as growth of a myotubular structure or neural structure from muscle or neural cells, respectively, or precursors therefor. In one embodiment, the cells are grown into a tissue. In another embodiment, the tissue is one of corneal endothelium, muscle and nerve tissue.

Also provided herein is a method of determining an effect of an environmental stimulus, such as presence of a chemical compound such as a drug (e.g., agent, compound, moiety etc.), a nucleic acid or a nucleic acid analog; pH, temperature, atmosphere composition, culture media composition, light, radiation, osmotic pressure, mechanical loading or stress, etc. on a cell. The method comprising culturing a cell in tissue culture media on a bioscaffold as described herein, exposing the cell to a chemical composition or non-chemical treatment; determining an effect of the exposure on the cell. The effect can be any parameter relating to the cell and can be determined in any manner useful in the arts, for example and without limitation: cell growth rate; cell survival; production rates and/or intracellular or extracellular location of a protein, nucleic acid or other composition or marker; differentiation of the cells or lack of differentiation; cell, monolayer or three-dimensional morphology; cell membrane permeability; or sensitivity to an environmental stimulus, such as presence of a chemical compound such as a drug, a nucleic acid or a nucleic acid analog; pH, temperature, atmosphere composition, culture media composition, light, radiation, osmotic pressure, mechanical stress, etc. The effects can be determined by any useful assay, for instance and without limitation, cell or tissue morphology can be studied by light or fluorescent photomicrography, with the optional use of dyes, enzymes, fluorochromes, etc.

and mRNA levels can be determined by RT-PCR (reverse transcription followed by PCR, e.g., using a TAQMAN® protocol) and protein levels can be determined by western blot, in situ hybridization, etc. In one embodiment, the cell is a cancer cell, a stein cell or a progenitor cell. According to one non-limiting embodiment, the chemical composition or non-chemical treatment is modifying a composition or a physical characteristic of the bioscaffold. For example and without limitation, the bioscaffold is modified by either changing the composition or the process by which the bioscaffold is manufactured, such as curing temperature, mixing speed, aeration, radiation treatment, etc.

According to an alternate embodiment, provided herein is a method of optimizing an elastic modulus of a nanoparticle-containing siloxane composition for use in growing or propagating cells. The method comprises preparing two or more bioscaffolds having different elastic moduli. The two or more bioscaffolds are prepared by mixing different ratios of a first composition comprising one or more polysiloxanes and nanoparticles with and a second composition that comprises a polysiloxane and which does not comprise the nanoparticle (that is, essentially and substantially nanoparticle-free) and cross-linking the polysiloxanes with an amount of crosslinker sufficient to fully cross-link the polysiloxanes. Various embodiments of useful polysiloxanes, nanoparticles, cross-linkers, ratios, etc. are described throughout this document. The method further comprises culturing a cell in cell culture media and determining which of the two or more bioscaffolds optimize a phenotype of the cell. Examples of such phenotypes include, without limitation: growth rate; changes in the level of and/or intracellular or extracellular location of a protein, nucleic acid or other marker; differentiation of the cells or lack of differentiation; cell, monolayer or three-dimensional morphology; cell membrane permeability; or sensitivity to an environmental stimulus, such as presence of a chemical compound such as a drug, a nucleic acid or a nucleic acid analog; pH, temperature, atmosphere composition, culture media composition, light, radiation, osmotic pressure, mechanical stress, etc. The method optionally may further comprise, generating an output indicating which of the two or more bioscaffolds produces an optimal phenotype and culturing the cells on the bioscaffold that produces/yields the optimal phenotype. The optimal phenotype may be determined by any method useful for determining the phenotype, such as the methods described in the Examples below. Methods for determining the phenotype are extremely varied and are a matter of choice for one of ordinary skill in the art, and can be performed readily by one of ordinary skill.

In one non-limiting example of a method for indicating a phenotype, one or more protein or nucleic acid marker in cells is labeled with a fluorescently-labeled probe or antibody and the cells are scanned for the presence of and/or pattern of fluorescence. The process can be automated, for example with two or more different bioscaffolds being placed in different wells of a multi-well tissue culture plate, culturing cells on the bioscaffolds until confluence or until another end-point, labeling the cells with a monoclonal antibody specific to a cellular protein, scanning the cells using a plate scanner illuminated with a light for excitation of the fluorochrome of the antibody, determining a pattern and/or level of fluorescence of binding of the antibody in the cells, and producing an output indicating which bioscaffold optimizes the production of the protein. Cells can then be cultured on a bioscaffold that yields or produces the optimal phenotype. Any of the described processes or steps may be automated using robotic and fluidic technologies, and any determination and output steps may be performed by or directed by one or more computers, which comprise at a minimum a processor, executable instructions for performing the determination and/or output steps. Producing automated devices and computer processes/programming to carry out any steps of the automated processes, for determining an optimal bioscaffold or for producing an output are within the skill of an ordinary artisan.

EXAMPLES

There is substantial variability in the literature for the reported elastic modulus of Sylgard 184 with reduced curing agent ratios (FIG. 1). Summarizing the results from ten different studies shows that the standard Sylgard 184 formulation with 1:10 curing agent to base ratio has reported elastic moduli ranging from 1 to 2.5 MPa. Reducing the curing agent ratio produces varying results that makes it difficult to choose the optimum formulation to achieve a PDMS with a specific elastic modulus. For example, the ratio of 1:50 has reported elastic moduli of 8, 12, 30 and 48 kPa, a 600% difference between the lowest and highest values (Ochsner M, et al. (2007) Micro-well arrays for 3D shape control and high resolution analysis of single cells. Lab On A Chip 7: 1074-1077; Bartalena G, et al. (2011) A novel method for assessing adherent single-cell stiffness in tension: design and testing of a substrate-based live cell functional imaging device. Biomed Microdevices 13: 291-301; Brown X Q, et al. JY (2005) Evaluation of polydimethylsiloxane scaffolds with physiologically-relevant elastic moduli: interplay of substrate mechanics and surface chemistry effects on vascular smooth muscle cell response. Biomaterials 26: 3123-3129; and Gray D S, et al. (2003) Repositioning of cells by mechanotaxis on surfaces with micropatterned Young's modulus. Journal of Biomedical Materials Research Part A 66A: 605-614). Similarly, to tune the elastic modulus to ~10 kPa reveals conflicting reports on whether 1:50, 1:55 or 1:67 is the appropriate curing agent to base ratio (Ochsner M, et al. (2007) Lab On A Chip 7: 1074-1077; Bartalena G, et al. (2011) Biomed Microdevices 13: 291-301; Ahmed N, et al. (2011) Long-term in situ observation of barnacle growth on soft substrates with different elasticity and wettability. Soft Matter 7: 7281-7290; and Gray D S, et al. (2003) Journal of Biomedical Materials Research Part A 66A: 605-614). It remains unclear what underlies this reported variability, but it likely includes multiple factors such as differences in curing time and temperature and accurate measuring and mixing of small quantities of curing agent. It should be noted that every one of these studies uses a unique combination of materials, ECM protein coatings, range of substrate elastic modulus and use or absence of micropatterning.

We hypothesized that polydimethylsiloxane (PDMS) blends could be used as the basis of a tunable system where the elastic modulus could be adjusted to match most types of soft tissue. To test this we formulated blends of two commercially available PDMS types, Sylgard 527 and Sylgard 184, preserving the stoichiometry of the crosslinking process during gel/elastomer formation, which enabled us to fabricate substrates with an elastic modulus anywhere from 5 kPa up to 1.72 MPa. This is a three order-of-magnitude range of tunability, exceeding what is possible with other hydrogel and PDMS systems. This method of formulation is in distinct contrast to the reduction of crosslinker commonly used to decrease the elastic modulus of Sylgard 184, which leaves a large proportion of free polymer in the system that can leach out. Uniquely, the elastic modulus can be controlled independently of other materials properties including surface roughness, surface energy and the ability to functionalize the surface by protein adsorption and microcontact printing. For biological validation, PC12 (neuronal inducible pheochromocytoma cell line) and C2C12 (muscle cell line) were used to demonstrate that these PDMS formulations support cell attachment and growth and that these substrates can be used to probe the mechanosensitivity of various cellular processes including neurite extension and muscle differentiation. These examples illustrate the complex role substrate elastic modulus in combination with surface chemistry and micropatterning has on cell behavior.

Methods

Substrate Fabrication

Polydimethylsiloxane with Tunable Mechanical Properties

Commercially available PDMS, Sylgard 527 gel and Sylgard 184 elastomer (Dow Corning), were blended to create PDMS substrates with tunable mechanical properties. Sylgard 527 was prepared per manufacturer's directions by mixing equal weights of part A and part B in a Thinky-Conditioning mixer (Phoenix Equipment Inc, Rochester, N.Y., USA) for 2 minutes at 2000 RPM followed by 2 minutes of defoaming at 2000 RPM. Sylgard 184 was prepared per manufacturer's directions by mixing 10 parts base to 1 part curing agent using the same mixing and defoaming cycle. Four different mass ratios of the Sylgard 184:527 were evaluated; 5:1, 1:1, 1:5, and 1:10. Each blend was mixed by first preparing pure Sylgard 527 and 184 as described above, and then combining by the indicated mass ratio followed by an additional mixing and defoaming cycle. Once mixed, the PDMS was either poured into 150 mm diameter petri dishes to create ~2 mm thick films for mechanical testing or spincoated onto 25 mm diameter glass coverslips at 4,000 RPM to create ~15 μm thick films. All PDMS was cured at 65° C. overnight (12-24 hours) for all experiments. Previous studies have reported that this cure time and temperature are sufficient to cure the PDMS such that mechanical properties are constant throughout our experimental protocol (Ochsner M, et al. (2007) "Microwell arrays for 3D shape control and high resolution analysis of single cells," Lab On A Chip 7:1074-1077). PDMS coated coverslips were treated in a UV-Ozone cleaner (Novascan Technologies, Ames, Iowa, USA) for 15 minutes before protein coating or microcontact printing.

Microcontact Printing of ECM Proteins

Lines of fibronectin (FN) or laminin (LAM) were microcontact printed onto the PDMS substrates using an adaptation of previously reported techniques (Feinberg A W, et al. (2010) Surface-Initiated Assembly of Protein Nanofabrics. Nano Letters 10:2184-2191). Briefly, 20 μm wide, 20 μm spaced lines were designed using AutoCAD software and printed onto a transparency-based photomask. Glass wafers were spincoated with SPR 220.3 positive photoresist (Microchem, Newton Mass.), exposed to UV light through the transparency-based photomask, developed using MF-319 developer (Microchem) and post baked at 115° C. for 90 seconds. PDMS stamps for microcontact printing were prepared by mixing Sylgard 184 per manufacturer's directions (as described above), pouring the prepolymer over the patterned glass wafers and curing overnight at 65° C. Once cured, the PDMS was peeled from the wafer, cut into 1 cm² stamps and examined under phase contrast microscopy to ensure successful pattern development. The PDMS stamps were sonicated in 50% ethanol for 30 minutes to clean and sterilize them, dried using a nitrogen gun and then coated with 200 μL of 50 μg/mL LAM or FN (BD Biosciences, San Jose, Calif.) dissolved in sterile deionized water. The FN consisted of 60% unlabeled protein and 40% protein labeled with Alexa Fluor 546 Maleimide using an adaptation of previously published techniques (Smith M L, et al. (2007) Force-induced unfolding of fibronectin in the extracellular matrix of living cells. PLoS Biol 5: e268). The PDMS stamps were incubated with either LAM or FN at room temperature for 1 hour to allow for the protein to coat the stamps. The PDMS stamps were then rinsed in sterile deionized water (ddH$_2$O) and dried using a nitrogen gun before being placed patterned side down on the PDMS coated coverslips. After approximately 5 minutes the PDMS stamps were removed leaving behind the patterned protein. PDMS substrates micropatterned with fluorescent FN were used to validate proper protein pattern transfer across the different blends and were imaged using a Zeiss LSM 700 confocal microscope (Carl Zeiss, Inc., Thornwood, N.Y., USA). PDMS substrates with micropatterned lines of LAM were used for the culture of PC12 cells to demonstrate neurite alignment and growth, as described below. PC12 cell growth was restricted to the LAM lines without needing to use blocking agent as commonly used with other cell types.

Mechanical Characterization

The six PDMS formulations were poured into 150 mm petri dishes to a thickness of 2 mm and cured for 24 hours at room temperature followed by 4 hours at 60° C. Tensile bar strips were cut using a Zing Laser Cutter (Epilog Laser, Golden, Colo., USA) and uniaxial tensile testing was done on an Instron 5943 (Instron, Norwood, Mass., USA). A total of 6 samples from at least 3 different preparations were analyzed per condition. Samples were stretched at a rate of 2.00 mm/min until failure. The elastic modulus of the polymers was determined from the slope of the linear regression of the stress-strain curves from 0-10%.

Surface Roughness Analysis

PDMS coated glass coverslips were imaged using an MFP-3D-BIO atomic force microscope (AFM, Asylum Research, Santa Barbara, Calif.) to determine the surface roughness. All samples were imaged using AC mode in air with AC160TS cantilevers (Olympus Corporation, Center Valley, Pa., USA) with a scan size of 512×512 lines over an area 20 μM×20 μm. The root mean square (RMS) roughness was calculated using the Z-sensor height signal. A total of 9 locations (3 locations on each of 3 samples) were analyzed per formulation and the average RMS roughness of each blend was statistically analyzed using a one-way ANOVA on the ranks with Tukey post hoc test (Sigma Plot, Systat Software Inc., San Jose, Calif., USA).

Water Contact Angle

The relative surface energy (wettability) of each PDMS formulation was determined using water contact angle measurements. For each PDMS formulation, six PDMS coated coverslips were used as prepared and six PDMS coated coverslips were additionally coated with collagen type IV (COL4, Sigma-Aldrich CO, St. Louis, Mo., USA). COL4 was adsorbed onto the PDMS by placing the coverslips PDMS side down on a 200 μL drop of 50 μg/mL COL4 for 1 hour at room temperature and then rinsed twice and stored in phosphate buffered saline (PBS) until use. Advancing contact angle analysis was performed on a Rame-Hart Contact Angle Goniometer (Rame-Hart Instrument CO, Succasunna, N.J., USA). Briefly, a 1 μL drop of ddH$_2$O was placed on the surface and the average of the left and right angles was measured using DROPImage software (Rame-Hart Instrument CO, Succasunna, N.J., USA). Additional 1 μL drops were added until the contact angle no longer increased. The highest contact angle value was then determined to be the advancing contact angle for the surface.

Three spots on each of the coverslips were analyzed. The six values were then averaged and a two-way ANOVA with Holm-Sidak comparison (SigmaPlot) was used to determine any statistical differences between the wettability of the different PDMS formulations with and without the COL4 coating.

Cell Culture and Immnunofluorescent Staining

PC12 Cell Culture

PC12 cells (rat adrenal pheochromocytoma cell line, ATCC, Rockville, Md., USA) received from the supplier were designate as passage 1 and used between passage 5-10 for all subsequent experiments. The cells were maintained in RPMI-1640 Medium (ATCC) containing 10% horse serum (Sigma-Aldrich), 5% fetal bovine serum (FBS, Life Technologies, Grand Island, N.Y., USA), and 1% Penicillin-Streptomycin (Life Technologies). Cells were seeded at a density of 5,000 cells/cm$^2$ onto either Sylgard 527 or Sylgard184 substrates micropatterned with 20 μm wide, 20 μm spaced LAM lines. The seeding media consisted of RPMI-1640 medium supplemented with 50 ng/mL nerve growth factor (Life Technologies) and 1% horse serum to induce differentiation into a neuronal phenotype. The cells were imaged on days 3, 5, 7 and 14 after seeding to determine neurite length using a Nikon TS100 phase contrast microscope equipped with a Nikon D7000 camera (Nikon Instruments Inc., Melville, N.Y., USA).

C2C12 Cell Culture

Murine skeletal muscle C2C12 cells (ATCC) were cultured in growth medium consisting of Dulbecco's modified Eagle Medium with 4500 mg/ml glucose (DMEM-high glucose) supplemented with 10% FBS, 1% Penicillin-Streptomycin and 2 mM L-Glutamine (Sigma-Aldrich Co.). PDMS substrates were coated with FN by incubation with 25 ng/mL FN solution for 15 min and then washed three times with PBS. For myotube differentiation experiments, C2C12 myoblasts were seeded on the substrates at a density of 2-3×10$^4$ cells/cm$^2$ and grown to confluence for 24 hours. Myotube differentiation was induced by changing to differentiation medium consisting of DMEM-high glucose supplemented with 2% horse serum 1% Penicillin-Streptomycin and 2 mM L-Glutamine. After 5 days in differentiation media, cells were washed with PBS and then fixed and permeabilized in PBS containing 4% paraformaldehyde and 0.5% of Triton X-100 (Sigma-Aldrich Co.) for 15 min. After fixation, samples were incubated with in 1:100 dilutions of monoclonal anti-myosin heavy chain (MHC) antibody (Life Technologies part number 180105) and DAPI (Life Technologies) in PBS for one hour at room temperature. Samples were then washed 3 times in PBS and incubated in a 1:100 dilution of Alexa Fluor 488 goat anti-mouse antibody (Life Technologies part number A11001) for one hour at room temperature. Samples were then washed 3 times with PBS and mounted on glass slides using Prolong Gold antifade (Life Technologies). Myotubes were imaged using a Nikon AZ100 C2 laser scanning confocal microscope (Nikon Instruments, Inc.).

Quantitative Image Analysis

The PC12 and C2C12 cells were imaged and then analyzed to quantitatively assess cell response to the different PDMS formulations. For the PC12 cells, the neurite length as a function of time was used to understand relative growth rates on Sylgard 527 versus Sylgard 184. Phase contrast images of isolated neurites from PC12 cells were collected on days 3, 5, 7, and 14 after seeding. The neurite lengths were calculated using the NeuronJ plugin for ImageJ (U.S. National Institutes of Health, Bethesda, Md., USA) (Meijering E, et al. (2004) Design and validation of a tool for neurite tracing and analysis in fluorescence microscopy images. Cytometry A 58: 167-176), which facilitated the accurate tracing of the neurites. The average neurite length on Sylgard 527 and Sylgard 184 at each time point was compared using a Maim-Whitney Rank Sum Test (SigmaPlot). For the C2C12 cells, confocal images were analyzed to quantify the average length of MHC-positive myotubes as a function of the PDMS formulation (substrate elastic modulus). In addition, images were analyzed for the number of myotube clusters per unit area as a metric of differential cell response to the softer PDMS formulations. The myotube lengths were quantified using the segmented line tool in ImageJ. The cell density was calculated by counting the number of nuclei in each image using the particle counter tool in ImageJ and dividing by the area of the image. The myotube clusters were defined as groups of overlapping myotubes that and were quantified using the multi-point selection tool in ImageJ. The average myotube length and number of myotube clusters per unit area on the different PDMS formulations were compared using a one-way ANOVA on ranks with Dunn's pairwise comparison (SigmaPlot).

Results

Mechanical Properties of PDMS Formulations

Figure 2A:
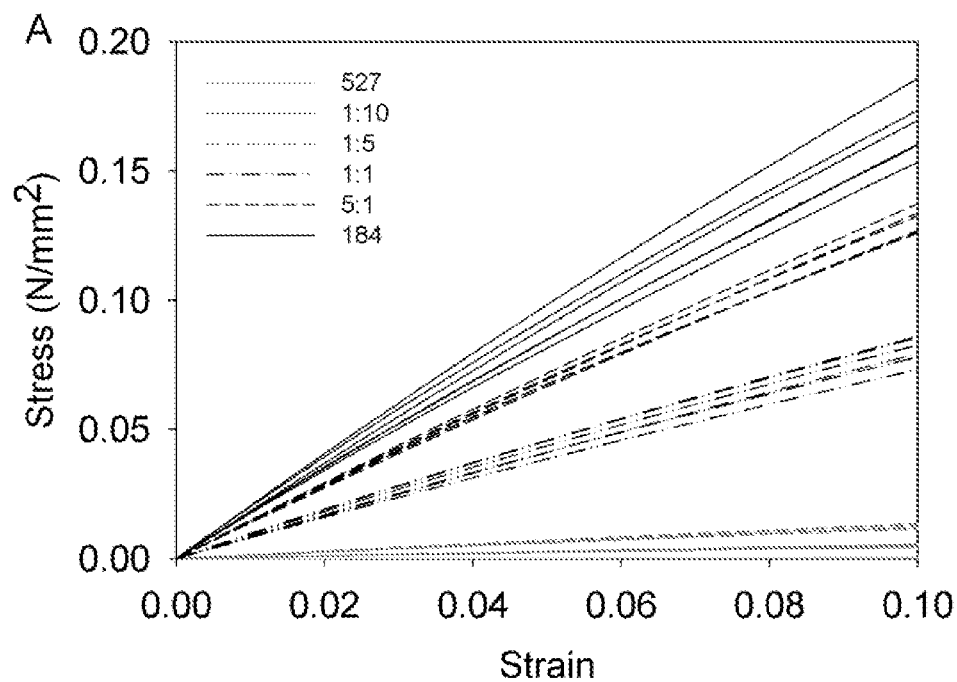
FIG. 2. PDMS formulations span a wide range of mechanical properties from soft gels to stiff elastomers. (A) Stress strain curves for the six different PDMS formulations show that the curves for each type (n=6) are clustered and separated from the curves of the other formulations. Over a 10% strain all formulations are linearly elastic. (B) Elastic modulus of the six different PDMS formulations as a function of weight percent Sylgard 184. The elastic modulus of each formulation is significantly different from the other PDMS formulations (One-way ANOVA, p<0.05). The curves predict that PDMS formulations can be fabricated with elastic moduli anywhere in the range from 5 kPa to 1.72 MPa by fine tuning the percentage of Sylgard 184 mixed in with the Sylgard 527. We have separated the data into two regimes, a non-linear regime for low percentages of Sylgard 184 (gray curve) and a linear regime for larger percentages of Sylgard 184 (black curve). The equation for the red curve is $y=0.3236x2+2.0606x+5$ ($R^2=1$). The equation for the blue curve is $y=18.591x-156.87$ ($R^2=0.995$). Data represented as mean±standard deviation.
Figure 2B:
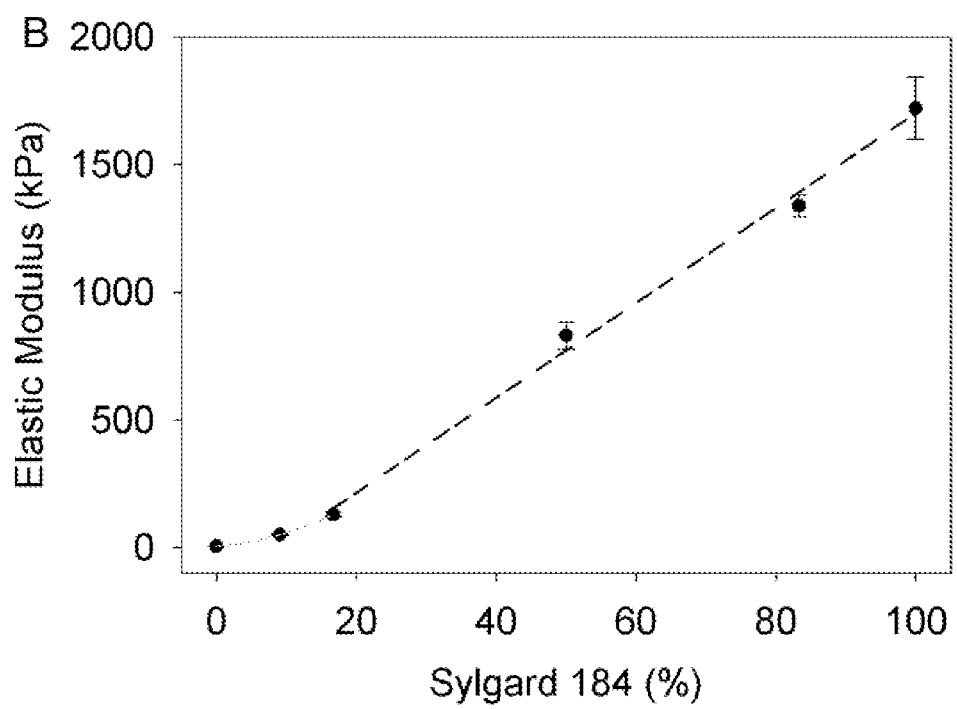

PDMS substrates were engineered by blending Sylgard 527 and Sylgard184 to tune the mechanical properties over a three order-of-magnitude range. Representative stress-strain curves (FIG. 2A) demonstrate the capability to engineer PDMS with consistent properties under uniaxial tensile loading. The curves for each formulation are linear under the range of strain investigated and are distinct, indicating that each PDMS has a different elastic modulus. The elastic modulus was determined by the slope of these curves throughout this linear regime from 0-10% strain. As expected, increasing the mass ratio of Sylgard 184 relative to Sylgard 527 increased the elastic modulus from 5.05÷0.37 kPa to 1.72±0.12 MPa (FIG. 2B). The six PDMS formulations could be adjusted from soft gels to stiffer elastomers or by simply mixing two commercially available PDMS types, covering the entire range of elastic moduli reported for soft tissues. The data for elastic modulus versus mass percent of Sylgard 184 (FIG. 2B) can be interpreted to fall into two regimes. From 0-20% Sylgard 184, the data is best fit by a 2nd order polynomial where the addition of small amounts of Sylgard 184 to the Sylgard 527 causes a nonlinear increase. From 20-100% Sylgard 184 the data is best fit by a linear regression where the addition of Sylgard 184 to the Sylgard 527 causes a linear increase. These two curves enable determination of the approximate mass ratio of Sylgard 184 and Sylgard 527 required to create substrates with any elastic modulus within the tunable range, e.g., greater than 5 kPa (kiloPascals) and less than 1.72 MPa (MegaPascals). To simplify our terminology, we will subsequently refer to the PDMS formulations by the mean elastic modulus measured for each mass ratio; specifically Sylgard 527=5 kPa, 10:1=50 kPa, 5:1=130 kPa, 1:1=830 kPa, 1:5=1.34 MPa and Sylgard 184=1.72 MPa.

The six different blends have 6 distinctly different elastic moduli. The curves for each blend are tightly clustered illustrating the high reproducibility of this method. The elastic modulus can be tuned over the entire range and predicted by the curves (the lower region dominated by the Sylgard 527 properties and the upper region dominated by the properties of the Sylgard 184.

Surface Roughness

Figure 3:
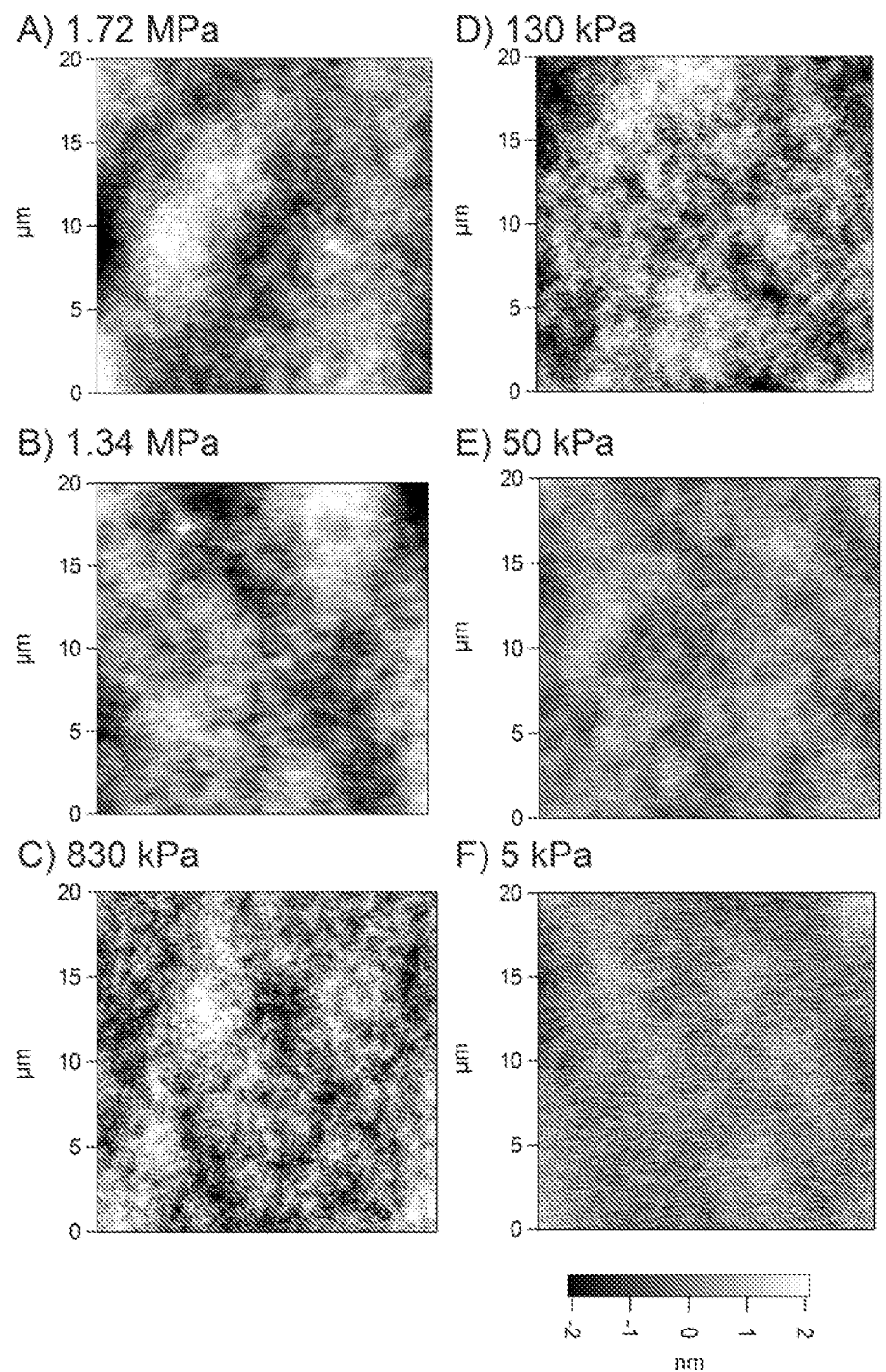
FIG. 3. Representative AFM scans of the surface topography for the different PDMS formulations. These images show that all PDMS formulations have similar morphological appearance and total variation in height of ~4 nm over a 20 µm scan area. The different scans are for (A) 1.72 MPa, (B) 1.34 MPa, (C) 830 kPa, (D) 130 kPa, (E) 50 kPa and (F) 5 kPa PDMS formulations.
Figure 4:
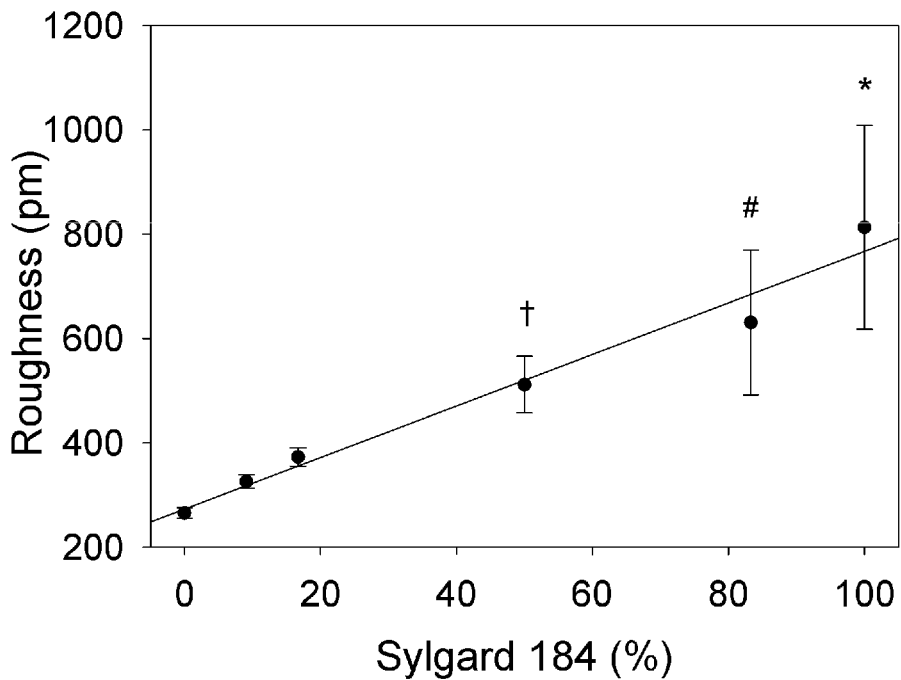
FIG. 4. RMS roughness of the six PDMS formulations as a function of weight percent Sylgard 184. As the percentage of Sylgard 184 increases, the RMS roughness also increases, ranging from approximately 200 to 800 µm. While there are significant difference in roughness between formulations, all have an RMS roughness of <1 nm, smaller than what cells can typically differentiate. Thus, we consider all the PDMS formulations to have equivalent surface roughness in terms of what a cell can sense and respond to. The relationship between RMS roughness and weight percent Sylgard 184 is fit by a linear regression (solid line, $y=273.25+4.94x$, $R2=0.9745$). Data represented as mean±standard deviation, statistical significance determined by one-way ANOVA on the ranks with Tukey post hoc test (n=9) where (*) was significantly different from 0, 9.09 and 16.67%, (#) was significantly different from 0 and 9.90% and (†) was significantly different from 0% Sylgard 184 formulations ($p<0.05$).

We evaluated the surface roughness to determine whether there was a difference between the PDMS formulations that might influence cell response. AFM was used to analyze the surface topography and generate height maps in order to calculate the RMS roughness. All the formulations had a similar appearance over a square 20 μm scan size (FIG. 3). It should be noted that for the four PDMS blends there were no indications of phase separation between the Sylgard 184 and Sylgard 527, appearing to be completely miscible in one another as expected. Further, the fumed silica nanoparticles in the Sylgard 184 did not alter the surface morphology, with all samples generally varying in height no more than 4 nm over the scan area. The RMS roughness of the PDMS increased linearly with elastic modulus (FIG. 3). Statistical analysis using one-way ANOVA on the ranks with Tukey post hoc test indicated that the PDMS with elastic modulus of 1.72 MPa had a higher RMS roughness compared to the 5, 50 and 130 kPa formulations, that 1.34 MPa PDMS had a higher RMS roughness compared to 5 and 50 kPa formulations; and that 830 kPa PDMS had a higher RMS roughness compared to 5 kPa PDMS (FIG. 4). However, the RMS roughness was <1 nm for all the PDMS formulations, which is generally considered below the detectable range of cells. Thus, these results suggest that the surface roughness is equivalent in terms of biological affect across the entire range of elastic moduli. As the percentage of Sylgard 184 is increased, there is some slight variation in the surface roughness, however all are below 1000 pm, which is widely considered below what cells can sense since it is a fraction of the size of a molecule such as a proteins. This indicates that we can effectively alter the elastic modulus independent of the surface roughness.

Surface Wettability

Figure 5:
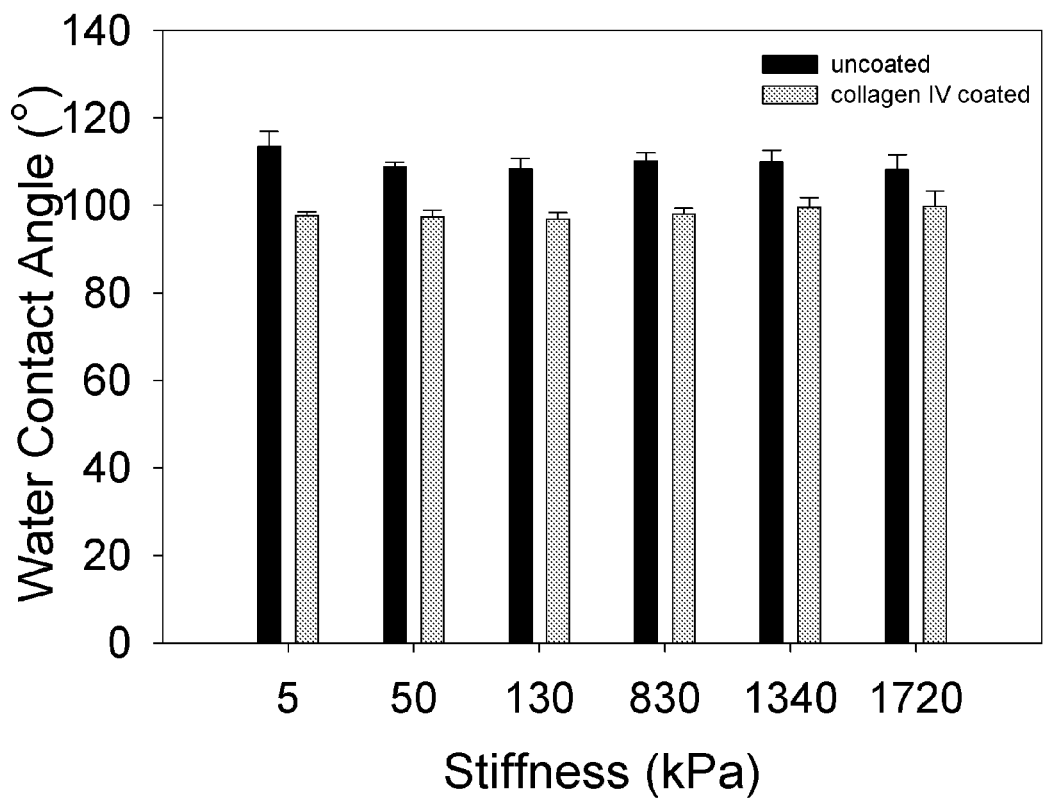
FIG. 5. Water contact angle of uncoated and collagen IV coated PDMS formulations. The water contact angles of all uncoated PDMS formulations (black) are approximately 110°, indicating a similar surface energy and hydrophobicity. The water contact angles of all PDMS formulations decreases to approximately 100° when coated with collagen type IV (gray), indicating similar protein adsorption behavior and surface energy. All uncoated PDMS formulations were quite hydrophobic presumed to be indistinguishable to cells despite the small, but statistically significant differences in water contact angle between the 5 kPa versus the 1.72 MPa, 130 kPa and 50 kPa substrates (# indicates p<0.05). All collagen type TV coated PDMS formulations were equivalent and had statistically significant decreases in water contact angle compared to the uncoated PDMS (* indicates p<0.05). Data represented as mean±standard deviation, statistical significance based on two-way ANOVA with Holm-Sidak pairwise comparison (n=6).

The surface energy of a substrate can affect the types and amounts of proteins that are able to adhere to the surface, affecting cell adhesion and behavior. We used water contact angle measurements to determine whether the surface energy was constant for the different PDMS formulations (FIG. 5). The water contact angle of the uncoated PDMS was ~110° for all formulations, indicating a hydrophobic surface and comparable to previously reported values for Sylgard 184 and other types of PDMS (Brown X Q, et al. (2005) Evaluation of polydimethylsiloxane scaffolds with physiologically-relevant elastic moduli: interplay of substrate mechanics and surface chemistry effects on vascular smooth muscle cell behavior. Biomaterials 26: 3123-3129 and Olah A, et al. (2005) Hydrophobic recovery of UV/ozone treated poly(dimethylsiloxane): adhesion studies by contact mechanics and mechanism of surface modification. Applied Surface Science 239: 410-423).

In sum, measurement of the water contact angle was used to compare the surface energy between the blends as prepared (no coating) and after coating with the ECM protein collagen type IV. The water contact angle within both uncoated and collagen IV coated blends remained effectively constant across the formulations. These results show that the substrate elastic modulus can be tuned without changing the surface energy and therefore the chemistry of the surface.

There were statistically significant differences in the water contact angle between some of the PDMS formulations, but these did not follow a distinct pattern and were always between 105° and 110°, a difference that is likely below what a cell can sense given that all samples are quite hydrophobic in nature. Coating the PDMS with COL4 increased the hydrophilicity and decreased the water contact angle to ~100° for all the formulations. Of note, is that after protein coating with COL4 there was no statistically significant difference in the water contact angle between any of the conditions. Thus, even though small differences in contact angle were present before protein coating, after protein coating all the surfaces were comparable. Similar to the surface roughness, these results suggest that the surface energy after ECM protein coating is constant across the entire range of elastic moduli.

Microcontact Printing of ECM Proteins onto the PDMS Formulations

Figure 6:
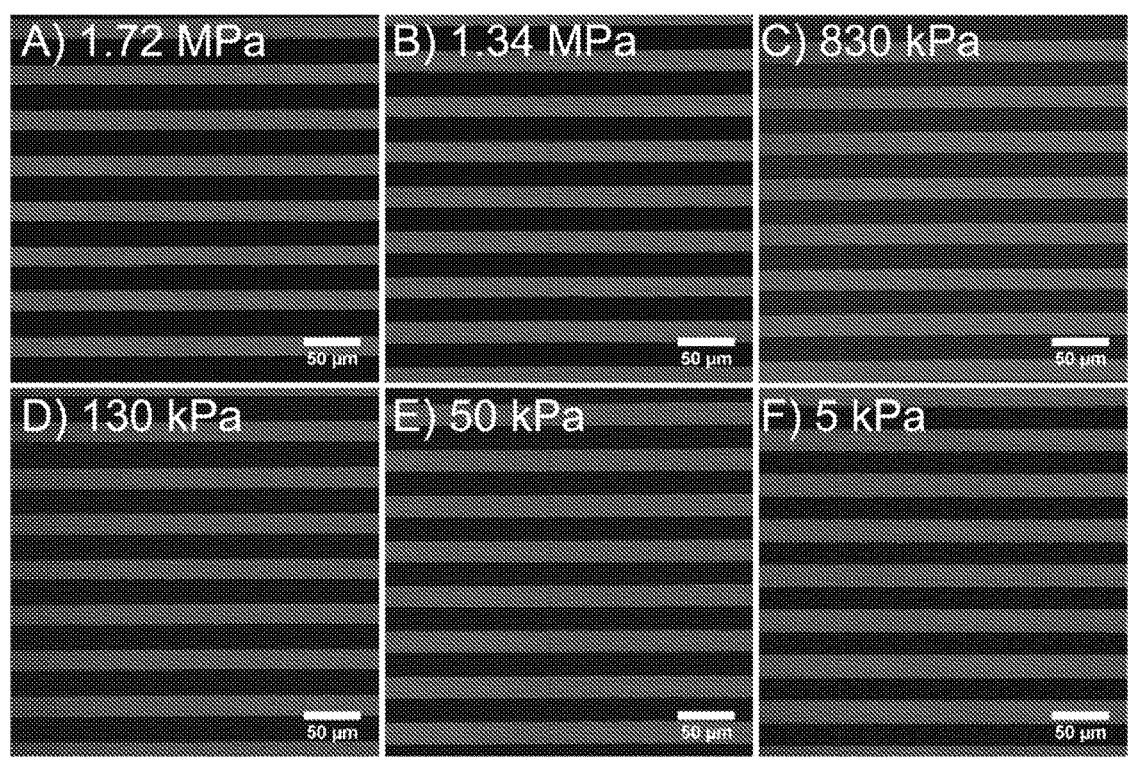
FIG. 6. Representative examples of fluorescently labeled fibronectin micropatterned on the different PDMS formulations. The protein pattern is transferred with high fidelity on all the PDMS formulations indicating the substrates exhibit similar protein adsorption from the PDMS stamps (Sylgard 184) used for microcontact printing. The different images are for (A) 1.72 MPa, (B) 1.34 MPa, (C) 830 kPa, (D) 130 kPa, (E) 50 kPa and (F) 5 kPa PDMS formulations. Scale bars are 50 µm.
Figure 7:
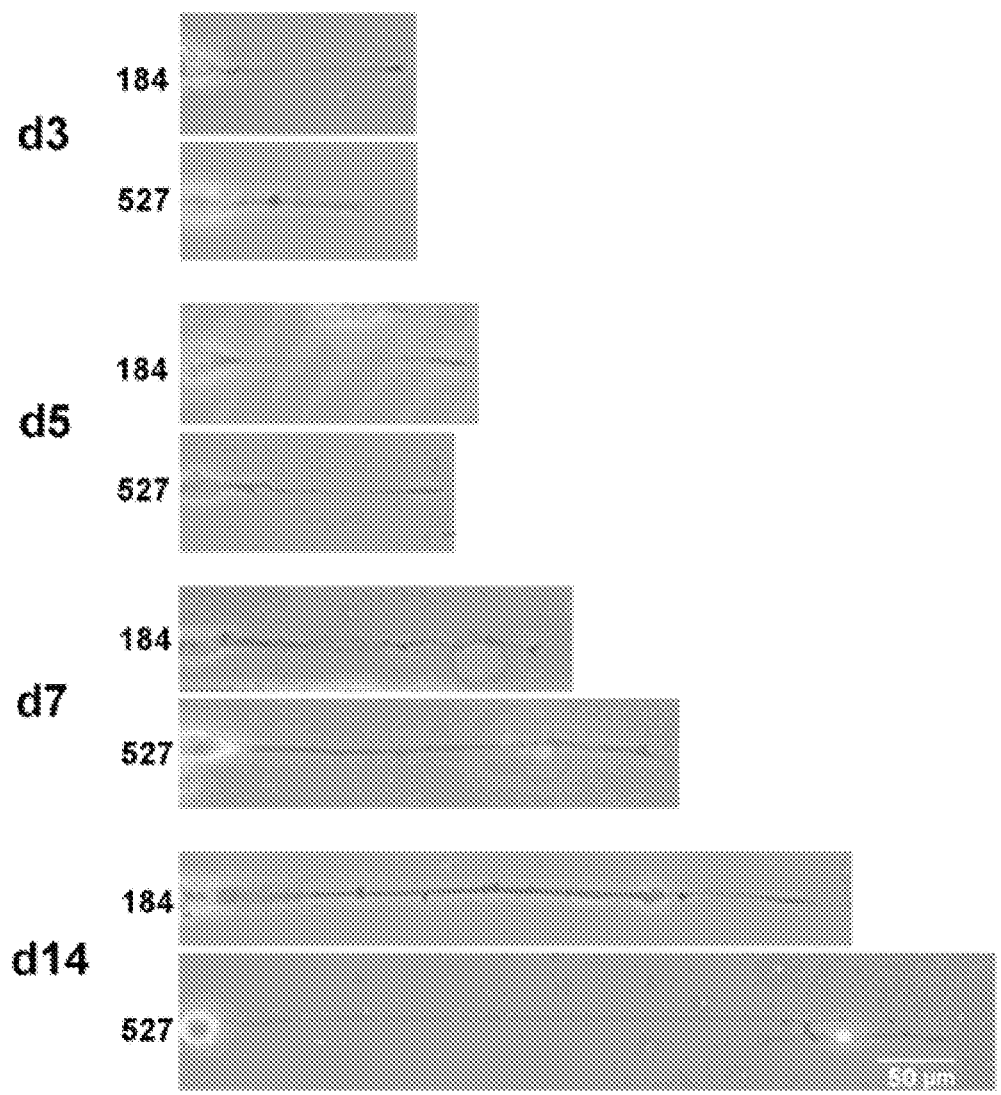
FIG. 7 Representative phase contrast images show single neurites extending from the cell body of PC12 cells. The PC12 cells were differentiated into neuron-like cells and cultured on 5 kPa and 1.72 MPa PDMS (Sylgard 527 and Sylgard 184, respectively). Laminin was micropatterned as 20 µm wide, 20 µm spaced lines to direct the linear extension of neurites, which were imaged at 3, 5 7 and 14 days. The neuron length increased with culture time and was qualitatively similar between the two PDMS types. Scale bar is 50 µm.

PDMS substrates are often micropatterned with ECM proteins in order to control the way cells adhere and interact. Soft substrates such as gels with an elastic modulus of <100 kPa have been difficult to pattern with techniques such as microcontact printing, instead requiring additional fabrication steps (Yu H Y et al. (2012) A novel and simple microcontact printing technique for tacky, soft substrates and/or complex surfaces in soft tissue engineering. Acta Biomaterialia 8: 1267-1272 and Perl A, et al. (2009) Microcontact Printing: Limitations and Achievements. Advanced Materials 21: 2257-2268). Here we show that microcontact printing was able to transfer FN onto each of the PDMS formulations with high fidelity (FIG. 6). The 20 μm wide, 20 μm spaced FN lines were well transferred with no apparent difference in the uniformity of protein coating. Additionally, we created the same line micropattern using LAM instead of FN on Sylgard 184 and Sylgard 527 (FIG. 7). Here we did not stain for the ECM protein, but rather evaluated bioactivity of the LAM via directed neurite extension of PC12 cells. The LAM patterns maintained anisotropic neurite extension for 14 days in culture demonstrating that the PDMS surfaces are able to maintain attachment of the LAM over this time and in the presence of FBS. It should be noted that the PDMS surfaces maintained the patterned ECM proteins over prolonged culture periods even though the ECM proteins were not covalently linked to the PDMS. Thus, all blends can be micropatterned with ECM proteins (fibronectin in this case) using the same basic microcontact printing method used in many labs. Typically, soft substrates (E<100 kPa) such as polyacrylamide gels need special procedures or additional chemical functionalization steps, but with our system, the same simple process is applicable across all elastic moduli.

Cell Behavior Response to Substrates with Variable Elastic Modulus

Rate of Neurite Extension on Hard and Soft PDMS

The PC12 cell line is widely used as model system because these cells are able to differentiate into neuronal-like cells that extend neurites. Previous reports have indicated that brain tissue has an elastic modulus of 0.1-1 kPa (Engler A J, et al. (2006) Matrix elasticity directs stem cell lineage specification. Cell 126: 677-689 and Perl A, et al. (2009) Microcontact Printing: Limitations and Achievements. Advanced Materials 21: 2257-2268). Thus, we used PC12 cells differentiated into neurons to determine if the rate of neurite extension was sensitive to the underlying substrate mechanics. Sylgard 527 (E=5 kPa) served as our brain-like stiffness and Sylgard 184 (E=1.72 MPa) served as our much stiffer material for comparison. We did not investigate intermediate elastic moduli because preliminary studies (data not shown) indicated minimal differences between many of the formulations. Because neurons will extend neurites in complex, isotropic orientations, we chose to micropattern the PDMS surfaces with 20 μm wide lines of LAM in order to direct uniaxial neurite extension and facilitate measurement of neurite length.

Figure 8:
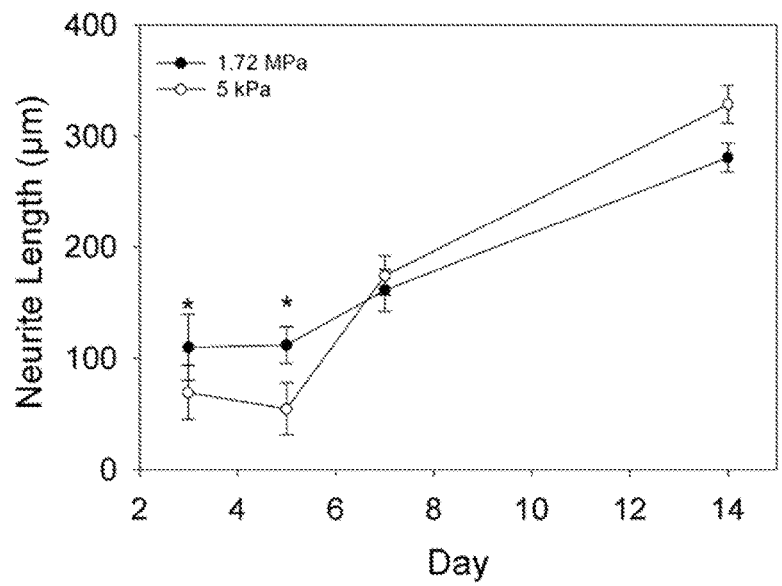
FIG. 8. Quantification of neurite length for PC12 cells cultured on two different PDMS formulations. PC12 cells were cultured on 1.72 MPa (●, black circles) and 5 kPa (○, white circles) PDMS and evaluated at days 3, 5, 7 and 14. At days 3 and 5, neurite length on 1.72 MPa PDMS was significantly greater compared to neurite length on 5 kPa PDMS. On days 7 and 14 the neurite length was equivalent on both PDMS types. This suggests that PC12 neurites initially grow faster on stiffer PDMS substrates (up to 5 days), but by 7 days the growth rate has slowed on the stiffer PDMS and accelerated on the softer PDMS such that neurite lengths are equivalent. Data represented as mean±standard error of the mean. Statistical significance at each time point determined by a Mann-Whitney Rank Sum Test, * indicates $p \leq 0.001$.

Success of the LAM patterning was demonstrated by the linear neurite growth (FIG. 7). The PC12 cells were differentiated into neurons and phase-contrast images were recorded on days 3, 5, 7 and 14 (FIG. 7). Quantification using ImageJ revealed a statistically significant increase in neurite length on Sylgard 527 versus Sylgard 184 at days 3 and 5, but by days 7 and 14 neurite length was statistically equivalent on both substrates (FIG. 8). This suggests that at early time points up to 5 days, neurites extend more rapidly on softer substrates with an elastic modulus more similar to brain tissue, however at longer time points the neurites on the stiffer PDMS appear to catch up such that neurite lengths are comparable by 7 and 14 days. The implication is that cells may have a transient response to substrate mechanics that affects growth kinetics, but that this difference may disappear over time as neurites reach a maximal length in culture.

In sum, to demonstrate that neural cells are sensitive to difference in substrate elastic modulus, we used the softest and stiffest PDMS to show that neurites extended from PC12 cells were longer on the stiffer substrate at days 3 and 5, but there was no different at days 7 or 14 (FIGS. 7 and 8). This demonstrates that cellular response to different elastic modulus substrates can be time dependent.

Myogenesis on Variable Stiffness Substrates

Figure 9:
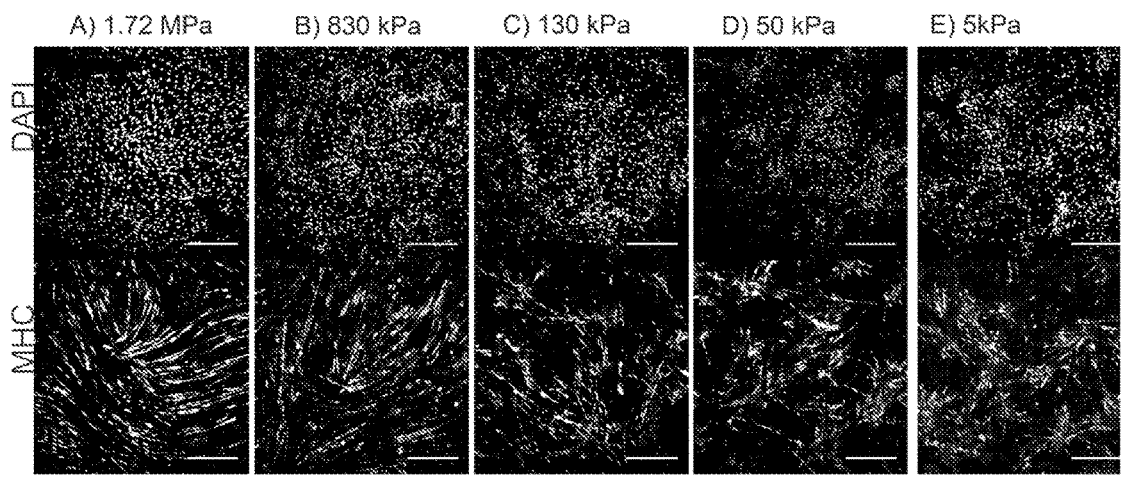
FIG. 9. Representative fluorescent images of C2C12 cells differentiated into myotubes on different PDMS formulations. C2C12 cells cultured and differentiated on PDMS (A) 1.72 MPa, (B) 830 kPa, (C) 130 kPa, (D) 50 kPa and (E) 5 kPa formulations. All cells were stained for the nucleus with DAPI (blue) and differentiated myotubes were stained for myosin heavy chain (Life Technologies Inc, part number 180105) (green). Cells cultured on the stiffer PDMS substrates (A-C) formed longer myotubes, whereas cells cultured on the softer substrates (D and E) formed shorter myotubes and tended to organize into cell clusters. Scale bars are 200 µm.
Figure 10A:
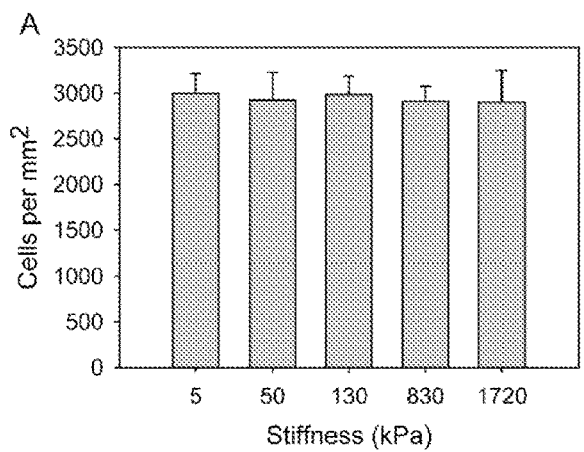
FIG. 10. Quantification of cell density, myotube length and myotube clustering performed as a function of the PDMS elastic modulus. (A) Average cell density of the different PDMS formulations shows no difference as a function of substrate elastic modulus. (B) Average number of myotube clusters per mm$^2$ on the different PDMS formulations (n=9). The cells cultured on the 5 and 50 kPa substrates formed significantly more myotube clusters compared to the other substrates (* indicates p<0.001). (C) Average length of myosin heavy chain positive myotubes on the different PDMS formulations (5 kPa, n=706; 50 kPa, n=739; 130 kPa, n=662; 830 kPa, n=769; 1.72 MPa, n=760). Cells cultured on the stiffer 1.72 MPa and 830 kPa substrates formed significantly longer myotubes compared to those formed on the softer 130, 50 and 5 kPa substrates (* indicates p<0.001). Cells cultured on the 130 kPa substrate also formed longer myotubes compared to those formed on the 5 kPa substrate (# indicates p<0.001). Data represented as mean±standard error of the mean, statistical analysis by Kruskal Wallis ANOVA on the ranks with p<0.05 Dunn's method for pairwise comparison.
Figure 10B:
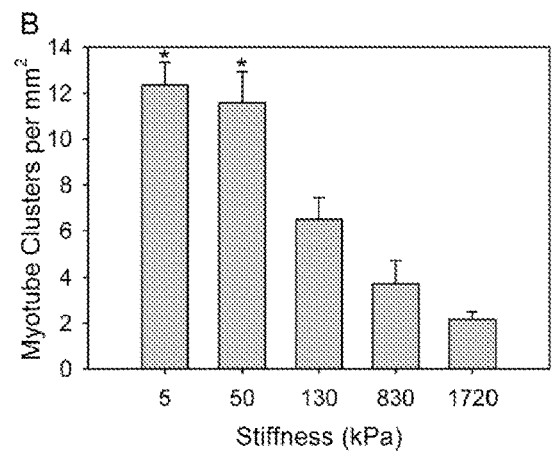
Figure 10C:
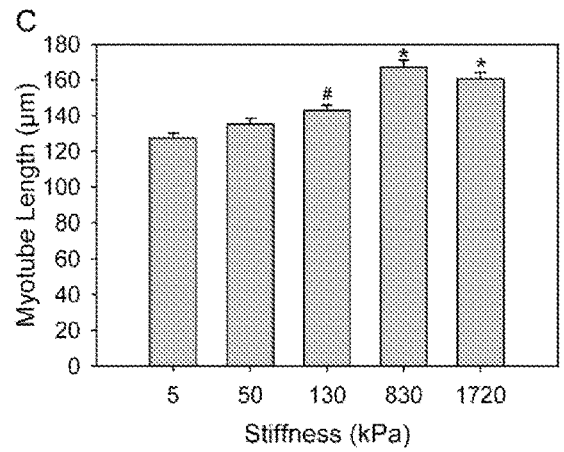

The C2C12 cell line is widely used to study myotube formation and has also been shown to differentiate into other cell types such as osteoblasts and adipocytes based on soluble cues and substrate mechanics Based on this, we studied the differentiation of the C2C12 myoblasts into myotubes on five of the PDMS formulations with elastic moduli of 1.72 MPa, 830, 130, 50 and 5 kPa. The surfaces were coated with FN to increase cell adhesion. Cells were cultured to confluence in growth media, differentiated for 5 days and then fixed and stained with MHC to visualize the myotubes and DAPI to identify cell nuclei. Results show that all PDMS formulations supported C2C12 adhesion, proliferation and differentiation into multinucleated myotubes (FIG. 9). While myotubes formed on all the surfaces, there were differences in myotube length and multicellular organization as a function of substrate elastic modulus. Myotubes on the stiffer PDMS (FIGS. 9A and 9B) were locally organized in parallel with each other, similar to that observed for these cell cultured on tissue culture polystyrene [49]. However, myotubes on the softer PDMS (FIG. 9C to 9E) formed myotube clusters where parts of many myotubes overlapped with each other and local alignment between myotubes was not apparent. Sylgard 527 has been used infrequently in the literature for cell culture [50], thus we wanted to verify that Sylgard 527 and the blends did not have increased cytotoxicity relative to the standard Sylgard 184. We quantified the number of C2C12 cell nuclei per unit area (cell density) on the different PDMS surfaces and demonstrated that there is no significant difference between formulations (FIG. 10A). The ability of Sylgard 527 to support equivalent cell density to Sylgard 184 after 6 days in culture strongly suggests equivalent biocompatibility between these two types of PDMS. Quantifying the number of myotube clusters that formed as a function of elastic modulus (FIG. 10B) revealed that this behavior increased for the softer materials, and appeared to reach a maximum for elastic moduli in the range of 5 to 50 kPa. This type of clustering behavior generally occurs when cells prefer adhesion to each other rather than to the substrate. In the case of these cells it suggests that substrate elastic modulus can regulate the preference between cell-cell adhesion and cell-substrate adhesion. The substrate stiffness also impacted the average myotube length, with myotubes on stiffer PDMS ~20% greater in length relative to softer PDMS (FIG. 10C). It is probable that the decreased myotube length and clustering behavior on the soft PDMS are coupled responses to substrate mechanics that have their basis in altered cytoskeletal structure, as previous studies have shown this type of mechanosensitivity in the cytoskeleton of C2C12 myotubes (Engler A J, et al. (2004) Myotubes differentiate optimally on substrates with tissue-like stiffness: pathological implications for soft or stiff microenvironments. Journal Of Cell Biology 166: 877-887).

In sum, C2C12 myoblasts were differentiated on 5 of the PDMS formulations. The cells formed longer myotubes, as indicated by myosin heavy chain (MHC) staining, on the stiffer substrates and formed more clumps on the softer substrates. With respect to quantification of C2C12 cell differentiation into myotubes on the PDMS formulations, cell density was equivalent across the formulations, so biocompatability was equivalent. There were longer more myotubes on the two stiffer substrates and more cell clumps on the 3 softer substrates.

Discussion

PDMS formulations formed by blending together Sylgard 527 and Sylgard 184 are able to cover this entire range and that the elastic modulus can be tuned independently of other material properties such as surface chemistry, energy and roughness. While Sylgard 184 has been used in a large number of cell culture studies, Sylgard 527 has been used infrequently (Hemphill M A, et al. (2011) A Possible Role for Integrin Signaling in Diffuse Axonal Injury. PLoS ONE 6: e22899) and there is a potential concern that it may not be biocompatible. To address this, we used C2C12 cells and demonstrated that after 6 days in differentiation media the cell density on Sylgard 527, Sylgard 184 and blends of the two were all statistically equivalent (FIG. 10A). This strongly suggests that there is no increased cytotoxicity associated with Sylgard 527. This makes sense based on the polymer chemistry, because Sylgard 527 and Sylgard 184 are primarily the same material consisting of dimethylvinyl-terminated dimethyl siloxane and dimethyl, methylhydrogen siloxane, with the main difference being that Sylgard 184 has a silica nanoparticle filler. While the exact composition of Sylgard 527 and Sylgard 184 are proprietary, the materials safety data sheets (MSDS) for each PDMS provides detail on the chemical components and those that are potentially cytotoxic (Corporation DC (Mar. 29, 2011) SYLGARD® 527 A&B SILICONE DIELECTRIC GEL. MSDS No: 01512269; Corporation DC (Mar. 15, 2011) SYLGARD® 184 SILICONE ELASTOMER CURING AGENT. MSDS No: 01015331; and Corporation DC (May 3, 2010) SYLGARD® 184 SILICONE ELASTOMER KIT (BASE). MSDS No: 01064291). For Sylgard 527 parts A and B, the MSDS states that they contain 85 to 100 wt % dimethylvinyl-terminated dimethyl siloxane and 1 to 5 wt % dimethyl, methylhydrogen siloxane. In contrast, the widely used Sylgard 184 contains more potentially cytotoxic chemicals. For Sylgard 184 Base resin, the MSDS states that it contains 0.5 wt % xylene, 0.2 wt % ethylbenzene, >60 wt % dimethylvinyl-terminated dimethyl siloxane, 30 to 60 wt % dimethylvinylated and trimethylated silica and 1 to 5 wt % tetra (trimethylsiloxy) silane. For Sylgard 184 Curing Agent, the MSDS states that it contains 0.19 wt % xylene, <0.1 wt % ethylbenzene, 55 to 75 wt % dimethyl, methylhydrogen siloxane, 15 to 35 wt % dimethylvinyl-terminated dimethyl siloxane, 10 to 30 wt % dimethylvinylated and trimethylated silica and 1 to 5 wt % tetramethyl tetravinyl cyclotetrasiloxane. These chemical compositions demonstrate that Sylgard 184 contains the two main siloxanes in Sylgard 527 plus additional chemicals and fillers including the solvent xylene, the carcinogen ethylbenzene and silica nanoparticles. While the MSDS does not provide complete information on chemical composition, it is clear that Sylgard 527 and the blends with Sylgard 184 all have the same basic siloxane chemistry and that there are no chemicals in Sylgard 527 that would increase its cytotoxicity relative to the widely used Sylgard 184.

The blends we have developed offer distinct advantages over previously reported methods to tune the elastic modulus of PDMS. In contrast to Sylgard 184, Sylgard 527 does not contain any fumed silica filler or other reinforcements. Mixing the A and B components in the recommended 1:1 ratio produces a PDMS with polymer chains that are crosssslinked into the network, yet have a very low elastic modulus (~5 kPa). Mixing increasing amounts of Sylgard 184 into Sylgard 527 achieves stiffer formulations that maintain the stoichiometry of the individual PDMS types while providing good control over the mechanical properties.

The C2C12 and PC12 cell lines both demonstrated mechanosensitive cellular responses to variation of the substrate elastic modulus, verifying the effectiveness of our tunable PDMS system. The C2C12 cells differentiated into myotubes on all of the PDMS surfaces, with a maximum myotube length on the 830 kPa substrate and a minimum on the 5 kPa substrate (FIG. 10C), While a number of studies have looked at various C2C12 differentiation metrics as a function of substrate mechanics, none have examined an elastic modulus range as large as we have. For example, Engler et al micropatterned lines of myotubes on PA gels and showed enhanced sarcomere formation on an elastic modulus of 11 kPa compared to gels only ~7 kPa softer or stiffer (Engler A J, et al. (2004) Journal Of Cell Biology 166: 877-887). What complicates comparison of our results to these micropatterned myotubes is that C2C12 cells cultured as 2-D sheets form myotubes on top of a layer of non-differentiated cells, which are the ones that are actually adhered to the substrate, which Engler et al has shown may be obscure the effect from the underlying substrate stiffness (Engler A J, et al. (2004) Journal Of Cell Biology 166: 877-887). However, it is evident from our studies that myotube length (FIG. 10B) and myotube clustering (FIG. 10C) were sensitive to order-of-magnitude changes in substrate elastic modulus. This is in general agreement with Xu et al, who used variable stiffness silk-based materials to show enhanced C2C12 proliferation and Myold expression on substrates with an elastic modulus of 20 MPa compared to 25 MPa and 5 MPa substrates (Hu X, et al. (2011) The influence of elasticity and surface roughness on myogenic and osteogenic-differentiation of cells on silk-elastin biomaterials. Biomaterials 32: 8979-8989). Using muscle progenitor cells rather than C2C12 cells, Boonen et al compared 3 kPa and 21 kPa PA gels and glass coverslips with various ECM coatings and generally found that myotube differentiation was best on the glass coverslip (elastic modulus >10 GPa) (Boonen K J M, et al. (2011) Interaction between electrical stimulation, protein coating and matrix elasticity: a complex effect on muscle fibre maturation. Journal of Tissue Engineering and Regenerative Medicine 5: 60-68 and Boonen K J M, et al. (2009) Essential environmental cues from the satellite cell niche: optimizing proliferation and differentiation. American Journal of Physiology—Cell Physiology 296: C1338-C1345). Considering all these results, what is clear is that differentiation of myoblasts into myotubes is sensitive to substrate mechanics, but it is not a simple relationship and that cell type, micropatterning, materials type and ECM coating all play a role. For comparison, the PC12 cells grew longer neurites on the 5 kPa substrate at 3 and 5 day time points, but by 7 days neurites on the 1.72 MPa substrate had reached the same length and continued to increase in length further out to 14 days. What this shows is that PC12 cells initially extend neurites farther on the softer substrate, but that this response to substrate mechanics is time dependent. Cheng et al showed similar results where PC12 cells differentiated for 6 days extended longer neurites on soft gelatin and gelatinchitosan composite substrates than on stiffer chitosan substrates (Cheng M, et al. (2003) Study on physical properties and nerve cell affinity of composite films from chitosan and gelatin solutions. Biomaterials 24: 2871-2880). Using very soft PA gels ranging from 7 Pa to 19 kPa, Leach et al showed an increase in neurite length for the stiffer substrates (Jennie B L, et al. (2007) Neurite outgrowth and branching of PC12 cells on very soft substrates sharply decreases below a threshold of substrate rigidity. Journal of Neural Engineering 4: 26), but even the stiffest PA gels was similar to the 5 kPa PDMS we used in our studies. In total, what our results show is that PC12 and C2C12 cells are responsive to the tunable PDMS over the three order-of magnitude range we have to work with.

We have demonstrated that PDMS formulations based on the blending of commercially available Sylgard 527 and Sylgard 184 are able to create biomaterials with tunable elastic modulus over three orders-of magnitude. This enables independent control of mechanics without any measurable effect on surface roughness, surface energy, the ability to absorb ECM proteins from solution or the ability to be micropatterned with ECM proteins. This is an improvement over what have been previously reported using PA gels and PDMS elastomers. Our cell studies demonstrate that all formulations support adhesion, growth and differentiation and that cell behaviors such as neurite extension and length of differentiated myotubes are sensitive to the differences in substrate elastic modulus. Our PDMS formulation are widely applicable to the study of cell response to variable substrate mechanics and have the advantage of being reproducible and simple to fabricate from commercially available, low cost PDMS while covering the largest range of physiologically-relevant elastic modulus reported in the literature.

Example 2—Growth of Corneal Endothelial Cells

The corneal endothelium is a monolayer of non-regenerative cells on the Descemet's membrane on the posterior surface of the cornea. The main function of these cells is nutrient transport and to pump fluid out of the stroma to maintain corneal clarity. Disease or injury to the CE causes corneal morbidity and is one of the most common causes for a full cornea transplant. There is a limited amount of available corneas for transplant and many of these corneas are unsuitable due to low CE cell counts. The Descemet's Membrane is reported to have an elasticity in the range of 20-80 kPa, and is much softer than tissue culture polystyrene (3-3.5 GPa). The whole cornea has been reported to have an elasticity of 0.15 to 57 MPa. ECM proteins found in the Descemet's membrane include: Collagen IV, Laminin and Collagen VIII Materials and Methods:

High Content Screen of Substrate Stiffness and Protein Coating:

Substrate Preparation:

Six different PDMS formulations were prepared as described above. Briefly, Sylgard 184 PDMS elastomer and Sylgard 527 PDMS gel (Dow Corning) were prepared separately according to the manufacturer's specifications.

Figures 11, 12:
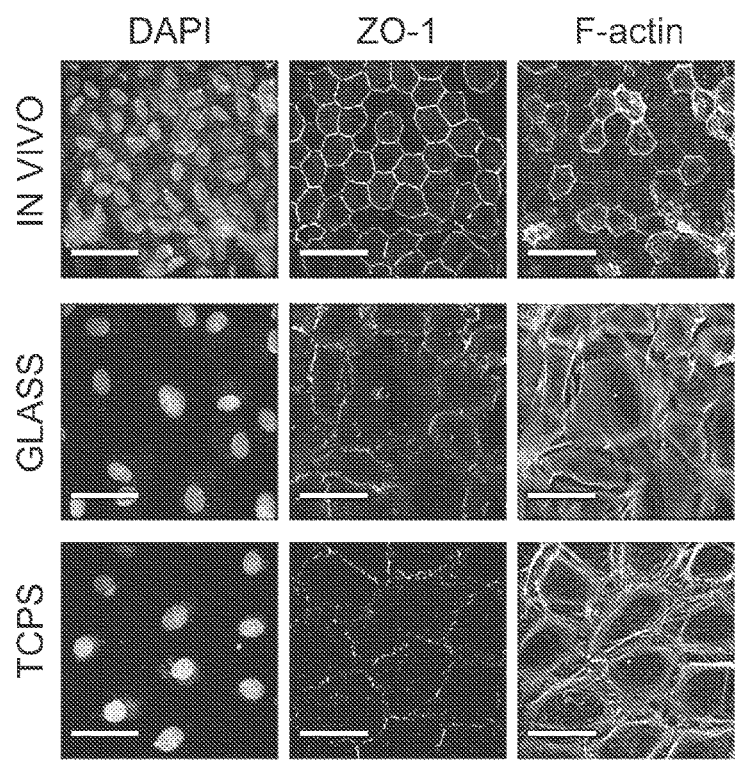
FIG. 11: Diagram showing the 36 different substrate conditions. Each column represents a different PDMS formulation and each row represents a different protein coating. The combination of the 6 formulations and 6 coatings resulted in a high content screen of 36 systematically varied substrate conditions.
FIG. 12. CECs lose differentiated morphology when cultured on glass or tissue culture polystyrene. CECs in vivo exhibit a polygonal shape and small size compared CECs cultured on glass at P3 and TCPS at P1. In vivo, the tight junction protein ZO-1 (Life Technologies Inc, part number 33-9100) (red) is present at cell borders and the F-actin (Life Technologies Inc, part number A34054) (green) is located cortically, whereas, cells cultured on rigid substrates have a reduced junctional ZO-1 localization and F-actin fibers present in the center of the cell. Scale bars, 50 µm.

Sylgard 184 (E=1.72 MPa, PDMS 1720) was prepared by mixing 10 parts base with 1 part curing agent for 2 minutes at 2000 RPM in a Thinky Cup Conditioning mixer (Phoenix Equipment Inc, Rochester, N.Y., USA) followed by a defoaming cycle of 2 minutes at 2000 RPM. Sylgard 527 (E=5 kPa, $PDMS_{5kPa}$) was prepared by mixing equal weights of part A and part B for 2 minutes at 2000 RPM followed by defoaming at 2000 RPM for two minutes. Four additional PDMS formulations were prepared by using the following mass ratios of the pure Sylgard 184: Sylgard 527: 5:1 (E=1.34 MPa, PDMS1340). 1:1 (E=830 kPa, PDMS830), 1:5 (E=130 kPa, PDMS130), and 1:10 (E=50 kPa, PDMS50). The two starting PDMS blends were weighed and mixed together using an additional mixing and defoaming cycle. All 6 PDMS formulations were spin coated onto 25 mm diameter glass coverslips at 4,000 RPM to create ~15 μm thick films followed by curing at 60° C. for 8 hours. Coverslips were treated in a UV-Ozone cleaner (Novascan Technologies, Ames, Iowa, USA) for 15 and coated with either, 50 μg/mL fibronectin (BD Biosciences, San Jose, Calif., USA), 100 μg/mL collagen I (Sigma-Aldrich CO, St. Louis, Mo., USA), 50 μg/mL laminin (BD Biosciences), 50μ/mL collagen W (Sigma-Aldrich), a mixture of 50 μg/mL laminin and 50 μg/mL collagen IV (in deionized water ($ddH_2O$)) by placing the PDMS side down on a 200 μL drop of the protein solution for one hour at room temperature. Uncoated controls and coated samples were rinsed three times in phosphate buffered saline (PBS) before cell culture experiments. FIG. 11 shows the resulting 36 substrate conditions.

Bovine Corneal Endothelial Cell Isolation and Culture:

Bovine CECs were isolated from fresh whole bovine eyes (Pel-Freez Biologicals, Rogers A R, USA). The corneas were excised from whole globes and soaked for 20 minutes in PBS containing 1% penicillin/streptomycin/amphotericin B (Life Technologies, Grand Island, N.Y., USA) and 0.5% gentamicin (Life Technologies). Corneas were incubated endothelial side up in a 12-well spot plate with approximately 300 μL of Tryple Express (Life Technologies) at 37° C. for 20 minutes. CECs were released into the Tryple Express by gently scraping with a rubber scalpel, combined and centrifuged for 5 minutes at 1500 rpm. The cells were designated as passage 0 (P0), resuspended in low glucose DMEM with 10% FBS, 1% penicillin/streptomycin/amphotericin B and 0.5% gentamicin (Life Technologies) and cultured in TCPS flasks.

High-Content Substrate Screening:

Coverslips were seeded with 300,000 bovine CECs (P3) and monitored for cell growth and morphology over a 7 day period using phase contrast microscopy. On day 7, all samples were fixed and permeabilized in PBS containing 4% paraformaldehyde and 0.5% of Triton X-100 for 10 minutes (Sigma-Aldrich Co.). After fixation, samples were incubated with 1:200 dilution of DAPI (Life Technologies) and 1:100 dilutions of monoclonal mouse anti-ZO-1 (Life Technologies part number 33-9100) and phalloidin (Life Technologies part number AA21422)) in PBS for 2 hours at 37° C. Samples were rinsed 3 times in PBS and incubated with 1:100 dilution of Alexa Fluor 555 goat anti-mouse secondary antibody (Life Technologies) for two hours at 37° C. Samples were rinsed 3 times in PBS and mounted using Pro-Long gold antifade reagent (Life Technologies). Confocal microscopy was performed on a Zeiss LSM 700 confocal microscope (Carl Zeiss, Inc., Thornwood, N.Y., USA). Four separate trials were completed with four different cell isolations.

Expansion of Cells using Biomimetic Substrate:

Three different substrates were utilized in the expansion experiments: 1) TCPS; 2) $TCPS_{COL4}$; and 3) $PDSM_{50+COL4}$; . . . . To prepare $TCPS_{COL4}$, a T-25 flask was coated with 5 mL of 50 μg/mL collagen IV (human placenta, Sigma-Aldrich CO) for one hour at room temperature, rinsed once and stored with 5 mL of $ddH_2O$ inside until use. $PDSM_{50+COL4}$ was prepared by coating T-25 flasks with a ~0.5 mm thick layer of the 50 kPa PDMS cured at 60° C. for 24 hours followed by UV-ozone treatment and coated with collagen IV as described above. All flasks were used within 3 days of protein coating. Bovine CECs from 10 corneas were isolated as described above and directly seeded onto one of the four substrates. Cells were cultured until confluent and serial passaged 1:3 until passage 10 (⅓ was maintained in culture, the other ⅔ were used for additional experiments or frozen for future experiments). Four separate trials were done with four separate cell isolations (TCPS n=4 flasks, $TCPS_{COL4}$ n=5 and $PDSM_{50+COL4}$ n=5 flasks). Cells were seeded onto $PDSM_{50}$ as an additional control, but failed to reach confluence on P0 after 30 days. Therefore $PDSM_{50}$ was not used is any further experiments. Cell morphology and confluence were monitored daily using a Nikon TS100 phase contrast microscope equipped with a Nikon D7000 camera (Nikon Instruments Inc., Melville, N.Y., USA). Cell density was calculated at confluence using the phase contrast images and the multi-point selection tool in ImageJ. To enable direction comparison of the different trials, cell density was normalized to the TCPS cell density at passage 0. Statistical analysis was done using a one-way ANOVA with Bonferroni post-hoc test (SigmaPlot Systat Software Inc., San Jose, Calif., USA). The total number of cells at each passage was calculated by the formula=cell density (e.g., $mm^2$) X area of substrate (e.g., $mm^2$)×3^(passage #) (or the total number of flasks). The native bovine cornea, and P1, 5 and 8 cells on the three substrates were fixed, permeabilized and stained as described above for the nucleus, ZO-1 and fibronectin (1:100 dilution of polyclonal rabbit anti-fibronectin (Sigma-Aldrich Co. part number F3648) with goat anti-rabbit Alexa fluor 488 secondary antibody (Life Technologies)) to determine protein localization. Samples were mounted using Pro-Long gold antifade reagent and visualized on a Zeiss LSM 700 confocal microscope.

Morphology Analysis:

The ZO-1 labeled samples above were used for quantitative morphology analysis because ZO-1 follows the border of the cell and the DAPI fluorescence was used to verify the presence of the cells in each location. Ten different images were obtained for each sample type on a Nikon TE2000-E equipped with a Photometrics CoolSnap HQ camera (Nikon Instruments Inc., Melville, N.Y., USA). Metamorph (Molecular Devices LLC. Sunnyvale, Calif., USA) was used to detect the ZO-1 fluorescence and create a rendering of the outline of each cell in an image. If any mistakes were made by the program in tracing the border of the cells, it was corrected manually before continuing on with the analysis. Metamorph was programmed to calculate the cell area (A) and perimeter (P). The hexagon shape factor for each cell was calculated by the equation $HSF=(P^2/A)-13.856$ (37, 38). The average cell area and hexagon shape factor at each passage was compared using a one-way ANOVA on the ranks with Dunn's pairwise comparison (SigmaPlot). Cells at the edges of the image were excluded from calculations.

PCR:

Total RNA was isolated from CECs cultured on the three different substrates at passages 1, 5, 8 and 10 as well as from uncultured bovine CECs and uncultured bovine stromal keratocytes for use as controls. The RNA was isolated and purified using the RNAeasy Mini kit (Qiagen), quantified, and the concentration adjusted with RNase-free water to 10 ng/μL. cDNA was prepared from 500 ng RNA by reverse transcription using SuperScript First-Strand Synthesis System (Life Technologies Inc.) in a TC-3000× thermocycler, (Techne, Inc). Quantitative real time PCR (qRT-PCR) assays were done using the SYBER Green system as per manufacturer's instructions (Applied Biosystems) in a (ABI 7700 Detection System; Applied Biosystems)) for 45 cycles of 15 seconds each at 95° C. and 60 seconds each at 60° C. after initial incubation for 10 minutes at 95° C. Initially 19 different genes were screened for using the uncultured CECs and keratocytes to determine which were more specific to endothelial cell or non-endothelial cell phenotype. After analyzing the initial results (data not shown), the following genes were chosen for the full experiment: COL3A1, COL4A2, COL8A1, and SLC4A4. 18S rRNA was used as an endogenous control for each sample type and triplicates of each sample were assayed. The mRNA expression was analyzed using the ABI EDS software and all data was compared to the expression of the uncultured keratocytes.

Results

Loss of CEC Polygonal Morphology During Standard In Vitro Culture

The native corneal endothelium has a distinctive cell morphology consisting of regular, hexagonally-shaped cells densely packed together into a continuous monolayer. This morpohology is common across species, and we confirmed that this was also the case for the 1 to 2 year-old bovine corneas used in this study. Staining intact corneal endothelium showed high cell density, a regular hexagonal morphology, near continuous staining of the tight junction protein zona occludens 1 (ZO-1) at the cell-cell borders and F-actin organized into a thin cortical layer (FIG. 12). In distinct contrast, CECs grown on standard cell culture surfaces such as glass coverslips or TCPS are characterized by lower cell density, an irregular morphology, punctate and discontinuous ZO-1 at the cell-cell borders and F-actin organized into a thick cortical cytoskeleton with formation of stress fibers that cross through the cell body. This change in CEC structure and morphology occurs even on the first passage of these cells on these surfaces, and becomes more pronounced through successive passages. Additionally, many CECs with a polygonal shape become senescent within 3 to 4 passages. Those CECs that do proliferate appear to undergo EMT and adopt a fibroblast-like morphology and loss of endothelial markers such as ZO-1. By passage 5 these de-differentiated, fibroblast-like cells dominate the culture. With this a baseline control for in vitro culture, our next step was to determine whether altering the substrate's surface properties could influence CEC growth characteristics.

High-Content Screen of Substrate Elastic Modulus and ECM Protein Coating

We hypothesized that culturing CECs on a surface that had mechanical and biochemical properties similar to their native environment, Descemet's membrane, would inhibit the loss of phenotype during in vitro culture. To test this, we implemented a screen that systematically varied substrate elastic modulus and ECM protein coating. We fabricated polydimethylsiloxane (PDMS) substrates with six different elastic moduli from 5 kPa to 1720 kPa; a range that fully encompasses the elastic modulus of both Descemet's membrane and the full cornea. The PDMS was either used as is or coated with one of five different ECM proteins; either fibronectin (FN), laminin (LAM), collagen type I (COL1), collagen type IV (COL4), or LAM and COL4, for a total of 36 different cell culture substrate conditions in our screen (Figure S1). Each substrate screened was seeded with $3.0 \times 10^5$ bovine corneal endothelial cells, on passage three with DMEM low glucose media with 10% FBS, 1% penicillin/streptomycin/amphothericin B and 0.5% gentamicin. The cells were cukltured for seven days in the same media, at 37° C., 5% $CO_2$. At seven days, cells were compared to native corneal endothelium to determine which substrate maintains morphology and phenotype.

We investigated LAM, COL4 and combination of the two because these are major constituents of Descemet's membrane. FN and COLI serve as controls where COLI is a major consituent of the stroma and FN is a major constituent of the provisional ECM laid down by fibroblasts. Bovine CECs were isolated from fresh whole bovine eyes (Pel-Freez Biologicals, Rogers A R, USA). The corneas were excised from whole globes and soaked for 20 minutes in PBS containing 1% penicillin/streptomycin/amphotericin B (Life Technologies, Grand Island, N.Y., USA) and 0.5% gentamicin (Life Technologies). Corneas were incubated endothelial side up in a 12-well spot plate with approximately 300 μL of Tryple Express (Life Technologies) at 37° C. for 20 minutes. CECs were released into the Tryple Express by gently scraping with a rubber scalpel, combined and centrifuged for 5 minutes at 1500 rpm. The cells were designated as passage 0 (P0), resuspended in low glucose DMEM with 10% FBS, 1% penicillin/streptomycin/amphotericin B and 0.5% gentamicin (Life Technologies) and cultured in TCPS flasks.

BCECs were expanded on TCPS by serially passaging the cells 1:3 until passage 2. The cells were then removed from the flasks using Tryple Express (Life Technologies Inc, counted and coverslips were seeded with 300,000 bovine CECs (P3) and monitored for cell growth and morphology over a 7 day period using phase contrast microscopy. On day 7, all samples were fixed and permeabilized in PBS containing 4% paraformaldehyde and 0.5% of Triton X-100 for 10 minutes (Sigma-Aldrich Co.). After fixation, samples were incubated with 1:200 dilution of DAPI (Life Technologies) and 1:100 dilutions of monoclonal mouse anti-ZO-1 (Life Technologies) and phalloidin (Life Technologies) in PBS for 2 hours at 37° C. Samples were rinsed 3 times in PBS and incubated with 1:100 dilution of Alexa Fluor 555 goat anti-mouse secondary antibody (Life Technologies) for two hours at 37° C. Samples were rinsed 3 times in PBS and mounted using Pro-Long gold antifade reagent (Life Technologies). Confocal microscopy was performed on a Zeiss LSM 700 confocal microscope (Carl Zeiss, Inc., Thornwood, N.Y., USA). Four separate trials were completed with four different cell isolations.

Figures 1, 13:
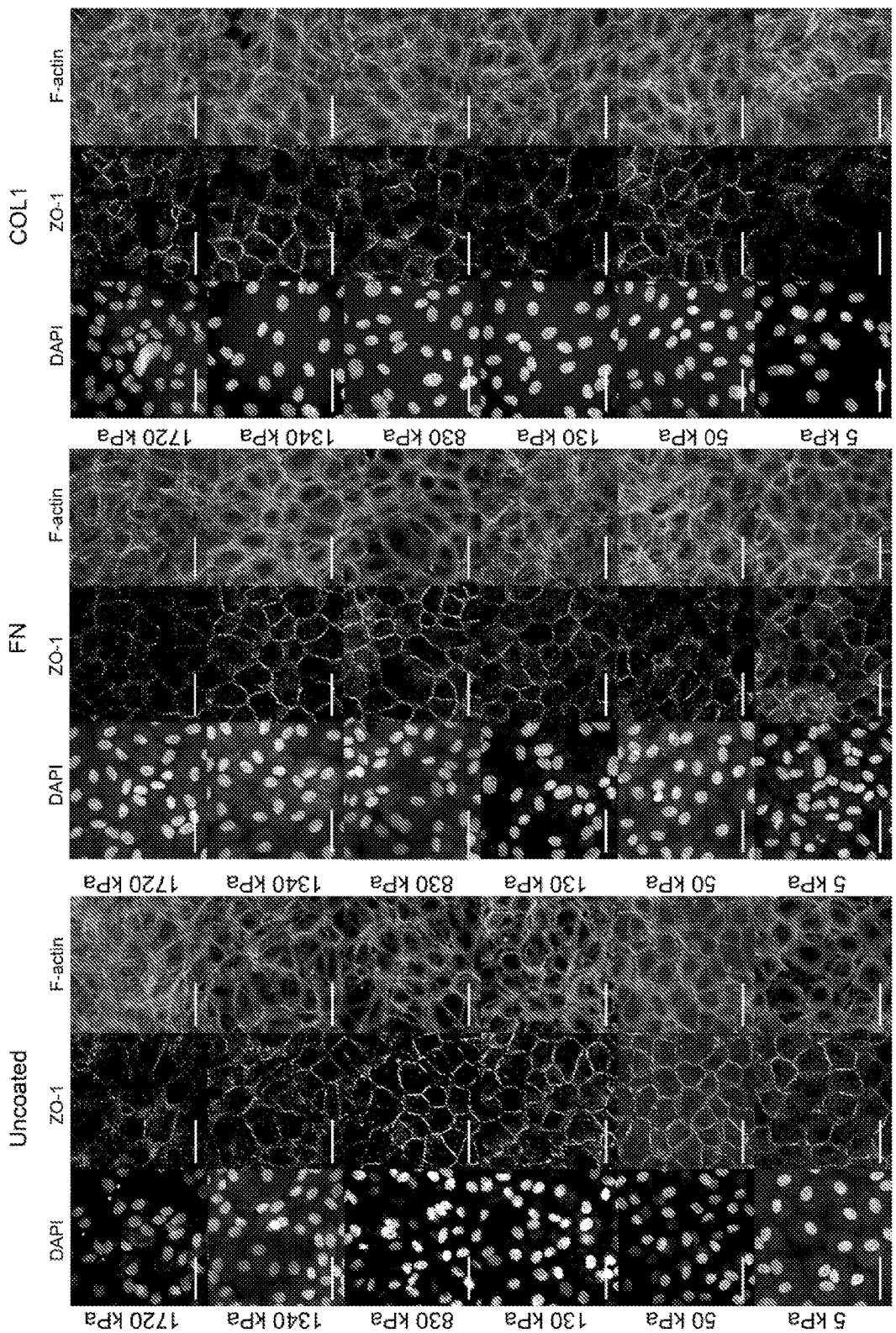
FIG. 13: A high content screen tested response of CEC morphology to substrate stiffness and extracellular matrix coating. Representative fluorescent images show CEC morphology, ZO-1, and F-actin localization in response to culture on 36 different substrates. Elastic modulus of the underlying PDMS is shown in rows and protein coating in columns. CECs were labeled for the nucleus (DAPI, blue, Life Technologies, Inc.), ZO-1 (anti-ZO-1, red, Life Technologies, Inc) and F-actin (phalloidin, green, Life Technologies, Inc). Cells on substrates with a stiffness of 50 kPa had a more polygonal cell morphology and ZO-1 and F-actin localization compared to cells cultured on all other substrates. CEC on collagen IV had a more polygonal morphology, ZO-1, and F-actin localization compared other substrates. The surface with an elastic modulus of 50 kPa and collagen IV coating was chosen for further studies. Scale bars are 50 µm.
Figures 2, 13:
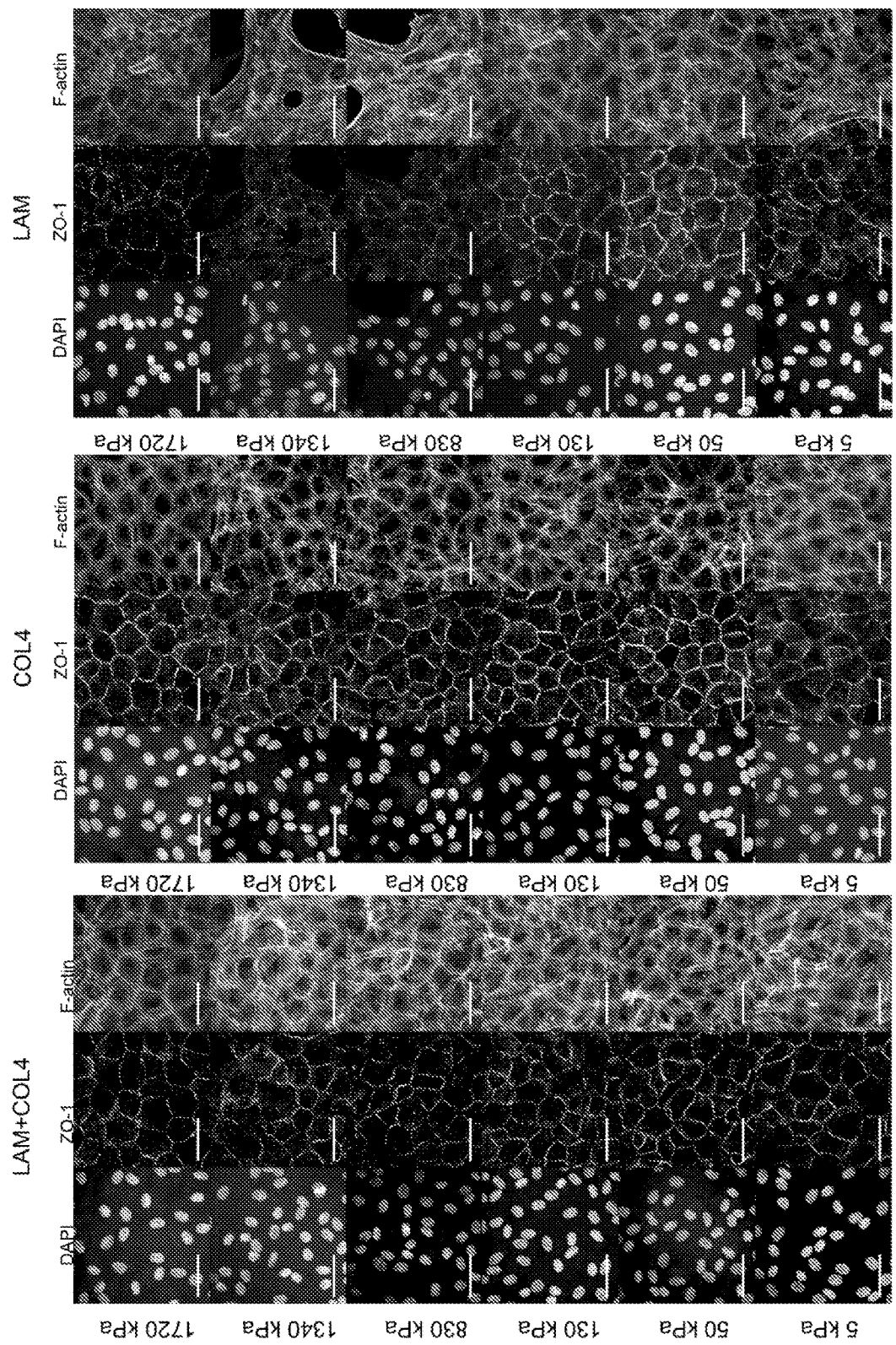

Representative results show that CEC response to the substrates was dependent on both the substrate elastic modulus and ECM protein coating (FIG. 13). Overall CEC density was similar across surfaces, but there were significant differences in ZO-1 and F-actin staining, indicating morphological changes. In general, on the stiffer PDMS formulations CECs had F-actin stained as a thick cortical cytoskeleton with internal stress fibers and minimal ZO-1 at the cell-cell border, similar to that observed on glass coverslips and TCPS. However, the ECM coating had a clear effect, as the CECs on COL4 exhibited a phenotype that most closely resembled that of the native endothelium displaying ZO-1 at all cell borders, F-actin located cortically, and a consistent polygonal morphology (FIG. 13). Decreasing the stiffness had variable response depending on the ECM coating. The FN and COLI surfaces showed no apparent difference with substrate stiffness while the LAM and COL4 surfaces showed subtle decrease in F-actin stress fibers and increase in ZO-1 at the cell borders down to E=50 kPa. Interestingly, CECs on the softest substrate, E=5 kPa, appeared similar to stiffer substrates, suggesting that a substrate with too low an elastic modulus may be detrimental. Note that the PDMS that was not pre-coated with an ECM protein, termed "uncoated" in FIG. 13, is actually coated by serum proteins from the media, primarily FN and vitronectin. While CECs on the uncoated surface had in vivo like morphology, it should be noted that cells grew on the surface much more slowly, suggesting that the CECs might be synthesizing and assembling an ECM as they grow rather than growing out on a pre-asorbed ECM. These results suggest that a substrate with an elastic modulus of 50 kPa, which is consistent with literature reports of Descemet's membrane elasticity, is the best mechanical condition for CEC culture. Based on mophology, F-actin cortical cytoskeletal structure and ZO-1 cell-cell border staining, we determined that COL4 gave the best results in terms of ECM coating and that a substrate elastic modulus of 50 kPa gave the best results in terms of mechanical properties. This combination is similar to the native Descemet's membrane, and thus this surface was considered to be biomimetic. Having identified this surface, we asked whether plating CECs on the biomimetic substrate from the time of initial isolation would enhanced expansion and phenotypic maintenance.

CEC Expansion is Enhanced by In Vitro Culture on Biomimetic PDMS Substrates

Figure 14:
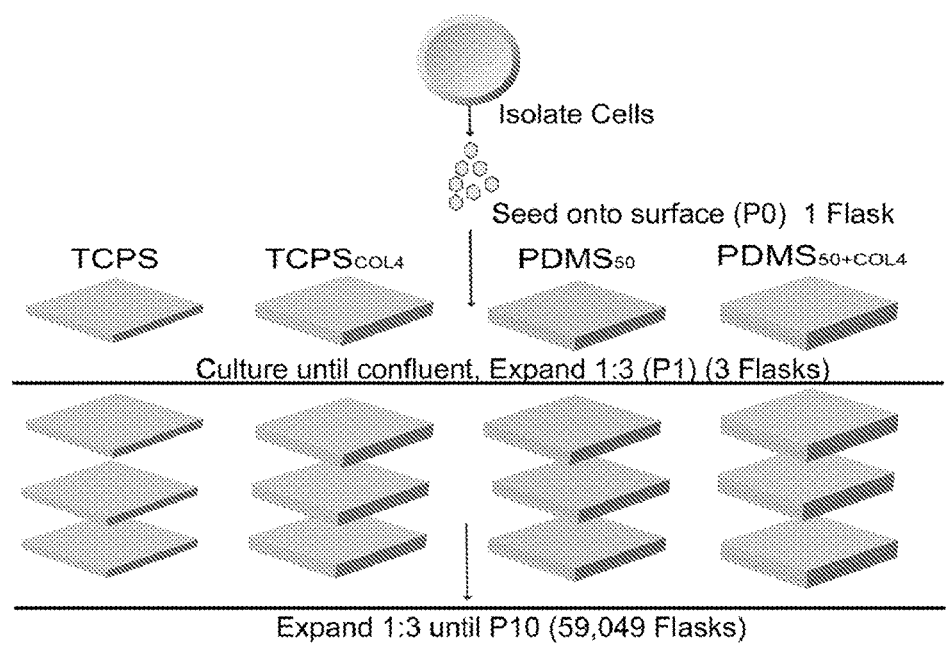
FIG. 14: Schematic diagram of the layout of the expansion experiment. This schematic shows the serial expansion process followed from isolation of the cells from the cornea, through passage 10.

Based on the results from the high-content screen, we hypothesized that culturing CECs on the biomimetic PDMS substrate direct from isolation would maintain phenotype while potentially enhancing proliferation by inducing cell division when seeded at sub-confluence. To test this, CECs were expanded by 1:3 serial passaging on the biomimetic substrate of 50 kPa PDMS coated with COL4 ($PDMS_{50\_COL4}$) and compared to TCPS as a standard control, TCPS coated with COL4 ($TCPS_{COL4}$), and 50 kPa PDMS ($PDMS_{50}$) without COL4. The CECs were isolated from the eyes of 1-2 year old cows and cultured on these substrates from initial seeding (P0) to passage 10 (P10) (FIG. 14).

Figure 15:
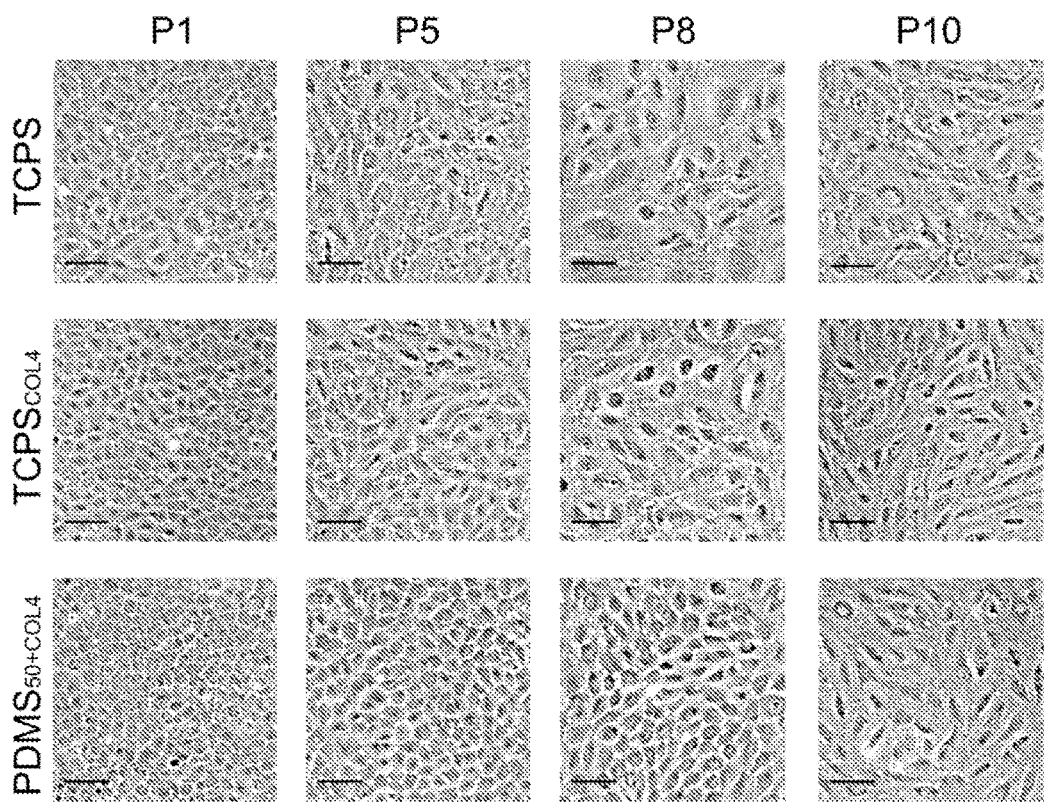
FIG. 15: Cell morphology is maintained at later passages in cells cultured on $PDMS_{50+COL4}$. Representative phase contrast images showing the morphology of cells cultured on the three different substrates at four different time points. As early as P5 cells cultured on $TCPS_{COL4}$ and TCPS begin to exhibit elongated, irregular cell morphology. By P8 the cells are very large and have no resemblance to a hexagonal morphology. In contrast, cells cultured on $PDMS_{50+COL4}$ maintain their hexagonal like morphology up to P8. Only at P10 do they become enlarged and elongated resembling the cells cultured on TCPS and $TCPS_{COL4}$. Scale bars are 100 µm.

The CECs cultured on $PDMS_{50}$ grew very slowly and failed to become confluent by day 30 at P0. When passaged to P1 CECs growth was equally slow, significantly lagging behind the other substrates. As a result, $PDMS_{50}$ was excluded from further analysis because proliferation rates were too low and it would take ~1 year for these cells to reach P10. Proceeding with CECs on TCPS, $TCPS_{COL4}$, and $PDMS_{50\_COL4}$, phase contrast imaging was used to track CEC morphology and proliferation over time (FIG. 15). At P1, CECs cultured on all three substrates exhibited a normal polygonal morphology; however, cells on TCPS were larger than those on $TCPS_{COL4}$ and $PDMS_{50\_COL4}$. At P5, CECs on TCPS and $TCPS_{COL4}$ had adopted an elongated morphology and at P8 were large and irregular in shape with enlarged nuclei and a fibroblast-like morphology. In contrast, CECs on $PDMS_{50\_COL4}$ at P5 and P8 maintained a higher density and a polyogonal morphology characteristic of CECs. At P10, CECs on all the substrates had adopted a fibroblast-like in morphology, suggesting a limit to how long CEC phenotype can be maintained even on the biomimetic PDMS substrate.

Figure 16:
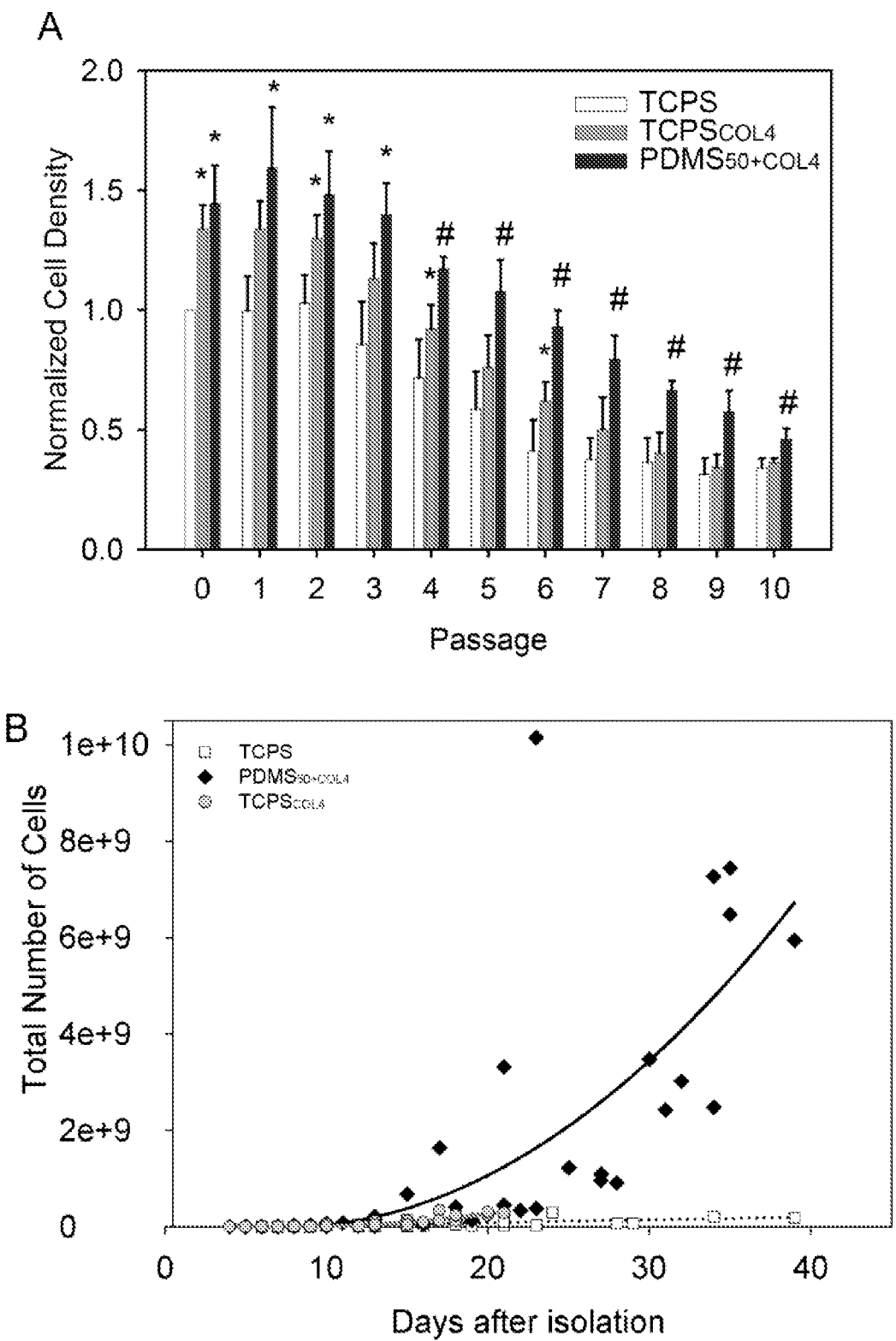
FIG. 16. Culturing cells on $PDMS_{50+COL4}$ results in a higher cell density and total number of cells at each passage. (A) Cell density was normalized to the TCPS flask at passage 0 for each trial to allow for direct comparison of the four different trials. Statistical significance was determined via a one-way ANOVA (p<0.001) with Bonferroni post-hoc test (p<0.05). At all passages the density of cells present on the $PDMS_{50+COL4}$ is significantly higher than the density of cells on the TCPS. From passage 4 to passage 10 the density of cells present on the $PDMS_{50+COL4}$ is significantly higher than the density of cells on the $TCPS_{COL4}$.* indicates statistical difference from TCPS and # indicates statistical difference from TCPS and $TCPS_{COL4}$. (B) Graph showing the total number of cells that could be obtained from a single isolation up to the passage in which the cells became irregular (P5 for TCPS and $TCPS_{COL4}$ and P8 for $PDMS_{50+COL4}$). There is a greater than 3000 fold increase in the total cell number on $PDMS_{50+COL4}$ and only a 139 and 138 fold increase on TCPS and $TCPS_{COL4}$ respectively.

CECs on the biomimetic $PDMS_{50\_COL4}$ substrate grew to a higher cell density than on TCPS and $TCPS_{COL4}$ at all passages. This behavior was consistently demonstrated across 4 separate isolations, where each isolation consisted of cells pooled from ten bovine corneas into each flask. To control for variability across isolations, we normalized cell density to CECs on TCPS at P0 and then graphed average normalized cell density at confluence for each substrate from P0 to P10 (FIG. 16A). Results show that the normalized cell density for CECs on $PDMS_{50\_COL4}$ at confluence was significantly higher than on TCPS at all passages and $TCPS_{COL4}$ from P4 to P10. Compared to TCPS, CECs on $PDMS_{50\_COL4}$ were ~50% higher density from P0 to P4 and ~100% higher density from P0 to P8. At each of these time points, CECs on the $PDMS_{50\_COL4}$ also maintained normal CECs morphology with a polygonal shape and a clear monolayer structure in contrast to CECs on TCPS and $TCPS_{COL4}$ (FIG. 15).

CECs on the biomimetic $PDMS_{50\_COL4}$ substrate also supported significantly enhanced proliferation compared to TCPS and $TCPS_{COL4}$ (FIG. 16B). We calculated the total number of CECs expanded as a function of time by multiplying the surface area of the culture flask by the cell density at confluence for each passage. The large difference in proliferation rate and total number of expanded CECs on $PDMS_{50\_COL4}$ was clearly evident from the data. CECs on $PDMS_{50\_COL4}$ maintained a polygonal morphology through P8 resulting in a >3000-fold expansion in the number of cells from the initial isolation. In contrast, CEC on TCPS and $TCPS_{COL4}$ maintained a polygonal morphology only through P5 resulting in a 139- and 138-fold expansion, respectively. Thus, these results demonstrate that the biomimetic $PDMS_{50\_COL4}$ substrate is able to both significantly enhance proliferation rate and total number of expanded cells while maintain the polygonal CEC morphology.

The Biomimetic PDMS Substrate Maintains CEC Gene Expression Patterns

Figures 1, 17:
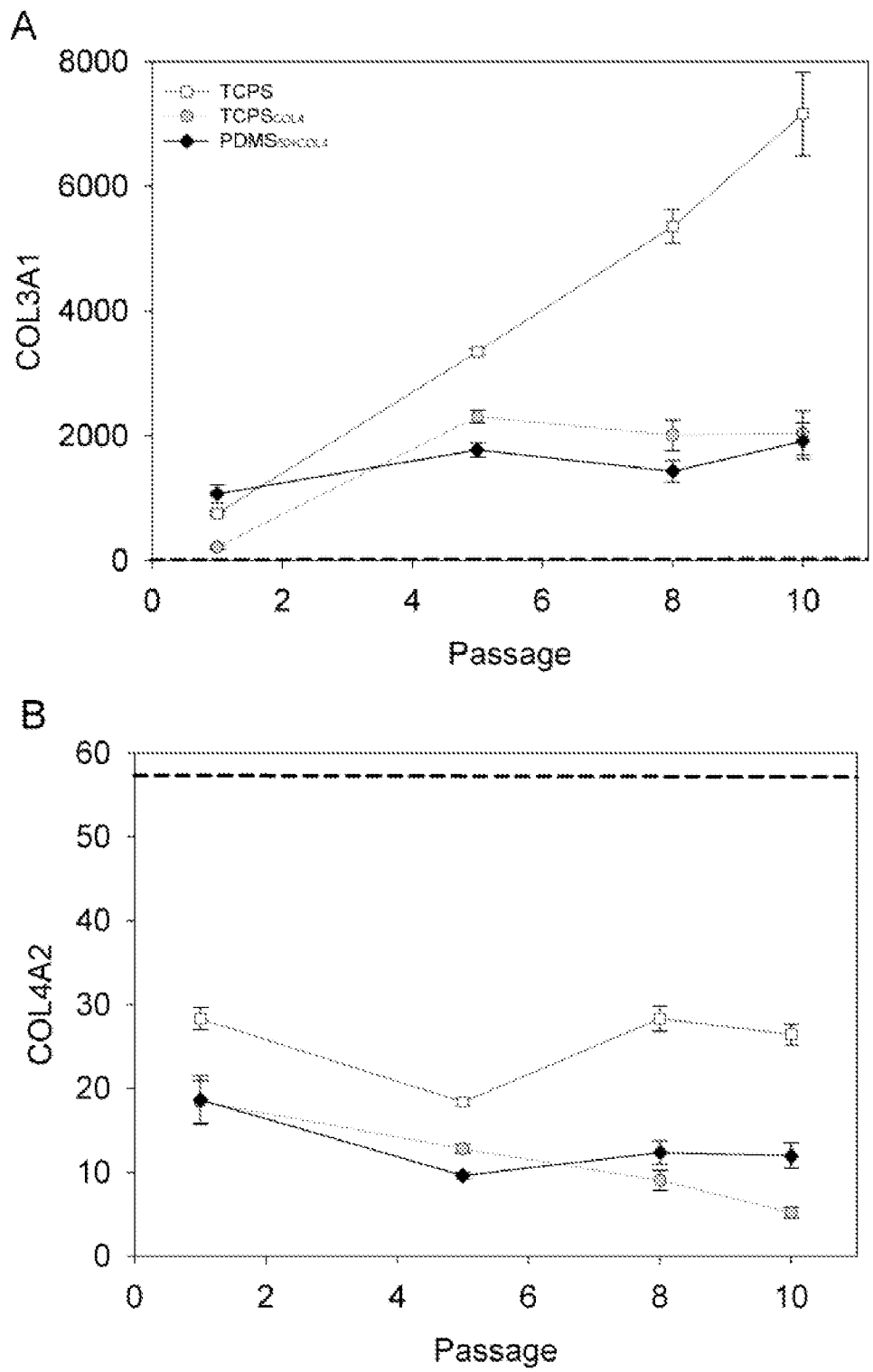
FIG. 17. mRNA expression of uncultured bovine CECs and CECs cultured on the three different substrates at passages 1, 5, 8 and 10 relative to mRNA expression in uncultured keratocytes. (A) COL3A1 (B) COL4A2 (C)COL8A1 and (D)SLC4A4. In each panel the back dashed line line across the graph represents the uncultured in vivo bovine CE mRNA expression level. Error bars are standard deviation of the three triplicates.
Figures 2, 17:
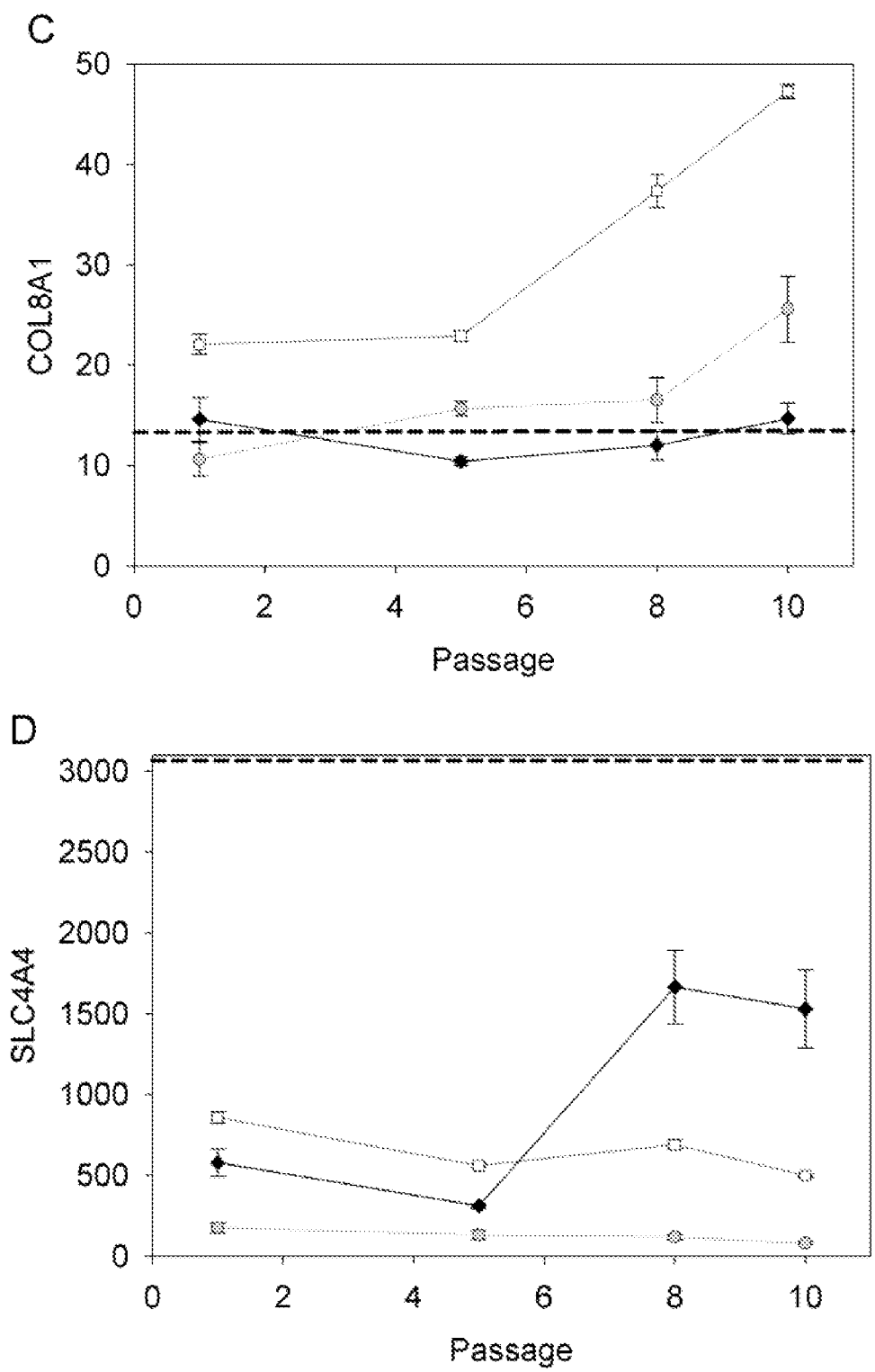

The CECs cultured on the biomimetic $PDMS_{50\_COL4}$ substrate maintained an in vivo like polygonal morphology relative to the other substrates (FIG. 15). But to quantitatively determine if CEC phenotype was maintained we analyzed gene expression patterns using qRT-PCR. Expression levels for CECs as isolated (in vivo state) and after 1, 5, 8 and 10 passages on the three substrates were calculated relative to expression levels for primary stromal keratocytes (a fibroblast-like cell found in the adjacent stroma in vivo) (West-Mays and Dwivedi (2006) The keratocyte: Corneal stromal cells with variable repair phenotypes. *Int J Biochem Cell Biol* PMID: PMC2505273 and DOI: 10.1016/j.biocel.2006.03.010). At P1 CECs on the substrates in vitro had similar gene expression levels to each other, but typically deviated thereafter. First we examined collagen type III (COL3), an ECM protein typically expressed by fibroblasts, especially during wound healing, and not expressed by CECs in vivo. Regardless of the substrate, CECs in vitro expressed increased amounts of COL3A1 mRNA compared to in vivo CECs (FIG. 17A). On $TCPS_{COL4}$ and $PDMS_{50\_COL4}$ the expression levels were relatively stable over time, but increased by ~8-fold on TCPS through P10. This suggests that coating the surface with COL4 decreases COL3 matrix synthesis, though we did not confirm that at the protein level. Next we examined the ECM proteins COL4 and collagen type VIII, which are major constituents of Descemet's membrane and not found in the adjacent stroma. The CECs in vitro expressed decreased amounts of COL4A2 mRNA levels were reduced in cultured CECs compared to in vivo and lowest in CECs cultured on the COL4-coated substrates (FIG. 17B). This suggests that CECs down regulate transcription of the COL4 gene when a stable COL4 ECM is present. The mRNA levels of COL8A1 was similar between CECs cultured on PDMS$_{50\_COL4}$ compared to in vivo, whereas cells expanded on the TCPS based substrates show increased expression levels at later passages (FIG. 17C). Finally, we examined the expression of mRNA for the sodium bicarbonate cotransporter-4 (SLC4A4), pump protein . . . . The level of SLC4A4 mRNA in cultured CECs was 10-20% compared to that in vivo at P1 and P5 (FIG. 17D), indicating that expression is tightly regulated. At later passages the levels of SCL4A4 mRNA remained low in CECs on TCPS and TCPS$_{COL4}$, but increased in CECs on PDMS$_{50\_COL4}$. In total, these results for gene expression suggest that the COL4 ECM coating and substrate stiffness act in concert to regulate phenotype maintenance. The decreased expression of COL3A1, COL4A2 and COL8A1 is similar for TCPS$_{COL4}$ and PDMS$_{50\_COL4}$, indicating that the COL4 coating may be the driving factor. In contrast, the increased expression of SLC4A4 for CECs on PDMS$_{50\_COL4}$ at later passages indicates substrate stiffness may be the The results indicate that the collagen IV coating and elasticity of the biomimetic substrate both contribute to the maintenance of CEC phenotype and increased expansion of cells.

ZO-1 and Fibronectin Localization Demonstrates a Fibroblastic Transformation on TCPS Substrates.

Figure 18:
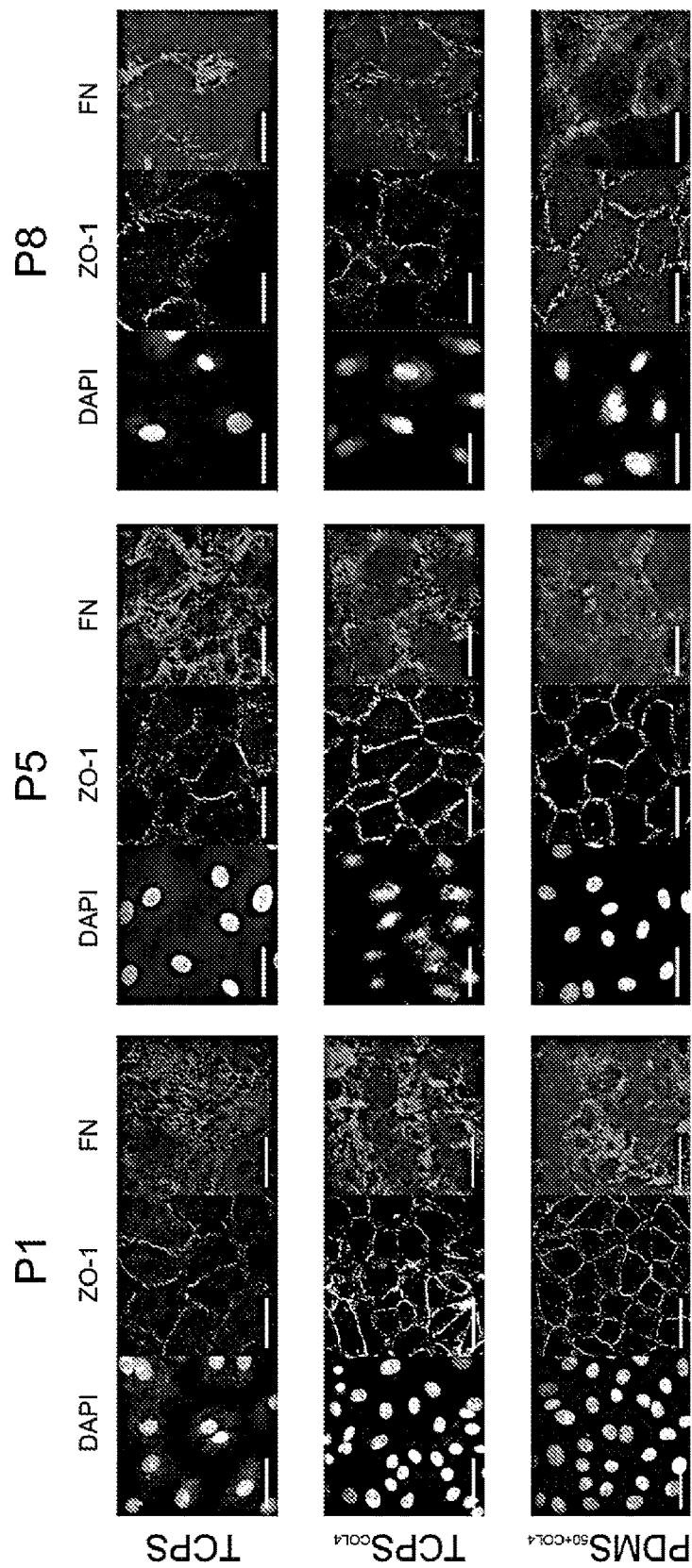
FIG. 18: Culturing cells on TCPS and TCPS$_{COL4}$ results in structural changes in the FN fibers produced by the cells and a loss of ZO-1 at the cell borders. Cells cultured on TCPS show very little ZO-1 expression at all passages with very little localized at the borders. The fibronectin expressed by the cells begins as short immature fibers at P1 but then at P5 begins to organize into long mature fibers indicative of a fibroblastic cell phenotype. Cells cultured on TCPS$_{COL4}$ show decreased expression and localization of ZO-1 at the borders of the cells as the passage increases from 1 to 8. The fibronectin produced by these cells shows a transformation similar to that seen on the TCPS from short immature to long mature fibers. Cells cultured on PDMS$_{50+COL4}$ show ZO-1 expressed and localized at the cells borders at all three passages. The fibronectin produced by the cells maintains the short immature fiber phenotype from P 1 to P8 and never organizes into longer mature fibers. Scale bars are 50 µm.

The presence and localization of ZO-1 is important in CEC cells as an indicator of properly formed tight junctions which are necessary for proper pump function. CECs cultured on TCPS showed very little of the tight junction protein ZO-1 at the cell borders at all passages, and cells cultured TCPS$_{COL4}$ began to show decreased regions of tight junctions at P5 (FIG. 18). Conversely, cells cultured on PDMS$_{50+COL4}$ maintained ZO-1 junctions to P8. Fibronectin is an ECM protein that is produced by all cell types in its immature punctate form. Fibroblastic or mesenchymal like cells bind, unfold and organize in to long fibers which are considered mature fibers and indicative of a fibroblastic cell phenotype. At P1 the structure of the fibronectin fibers produced by cells on all three substrates was similar. By P5, fibronectin fibers produced on TCPS and TCPS$_{COL4}$ become elongated and by P8 the fibronectin fibers on both substrates are not only elongated but are more organized indicating a more fibroblastic phenotype. In contrast, fibronectin fibers produced by the cells on PDMS$_{50+COL4}$ remained small and immature throughout 8 passages.

Cells on PDMS$_{50+COL4}$ Maintain Morphological Regularity and Smaller Cell Size.

Figure 19:
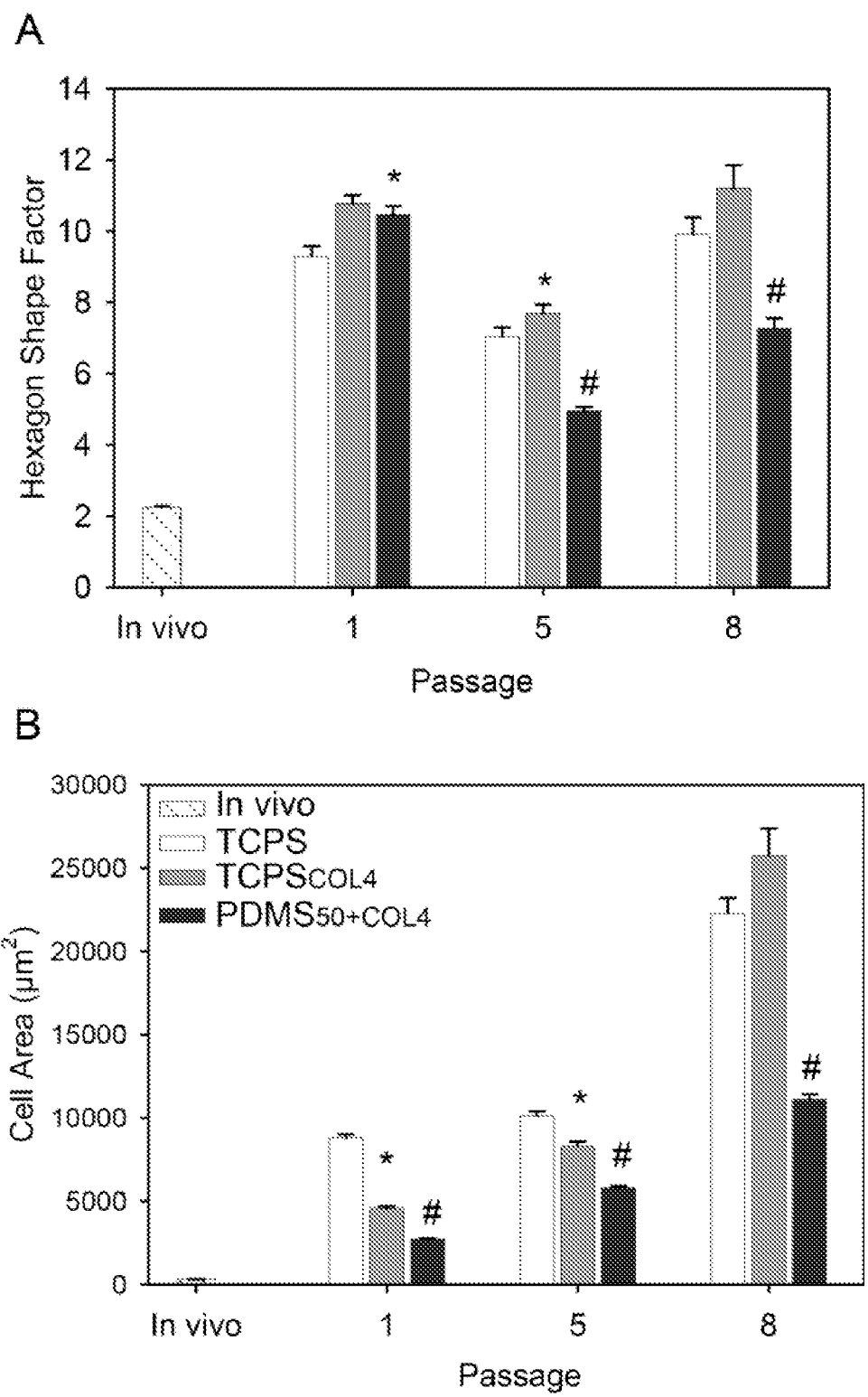
FIG. 19: Cells cultured on PDMS$_{50+COL4}$ have a more polygonal like morphology than cells cultured on TCPS and TCPS$_{COL4}$. (A) Average hexagon shape factor (mean±standard error of the mean). A one-way ANOVA on the ranks (p<0.001) with Dunn's pairwise comparison (p<0.05) was done at each passage to determine statistical significance. At P1 and P5, cells cultured on TCPS$_{COL4}$ had a significantly larger HSF than cells cultured on TCPS and PDMS$_{50+COL4}$ (indicated by the *). At P5 and P8 cells cultured on PDMS$_{50+COL4}$ had a significantly lower HSF than cells on the other two substrates indicating the cell morphology is more similar to the native bovine CECs (indicated by the #). (B) Average cell area (mean±standard error of the mean). A one-way ANOVA on the ranks (p<0.001 with Dunn's pairwise comparison (p<0.05) was done at each passage to determine statistical significance. At P1 and P5, cells cultured on TCPS$_{COL4}$ had a significantly smaller cell area than those cultured on TCPS (indicated by the *). However, at all passages, cells cultured on PDMS$_{50+COL4}$ had a significantly smaller cell area then cells cultured on the other substrates. This indicates the cells are more polygonal and smaller when expanded on the PDMS$_{50+COL4}$ substrate (indicated by the #). (In vivo cornea n=2674; TCPS P1 n=401, P5 n=353, and P8 n=135; TCPS$_{COL4}$ P1 n=846, P5 n=443, and P8 n=98; and PDMS$_{50+COL4}$ P1 n=1503, P5 n=673, and P8 n=318.)

CEC morphology is one of the most common metrics used to confirm CEC phenotype but is most often expressed qualitatively. To quantify the morphology of the cells, image analysis of ZO-1 labeled fluorescent micrographs of confluent monolayers was used to determine the hexagon shape factor (HSF) and the cell area. The HSF for each cell was calculated using an algorithm developed by Behndig HSF=$(P^2/A)-13.856$, where P is perimeter and A is the area of the cell (Behndig A (2008) Corneal endothelial integrity in aging mice lacking superoxide dismutase-1 and/or superoxide dismutase-3. Molecular Vision 14(238-39):2025-2030 and Behndig A, et al. (2001) Corneal endothelial integrity in mice lacking extracellular superoxide dismutase. Investigative ophthalmology & visual science 42(12):2784-2788). A perfect hexagon has an HSF of 0, but even the cells on the intact endothelium which appear to be perfect hexagons to the eye have an HSF that is above 0 meaning they are not perfect hexagons geometrically speaking (FIG. 19A). Cells cultured on TCPS$_{COL4}$ had a larger HSF at P1 and P5 compared to TCPS and PDMS$_{50+COL4}$ indicating a less hexagonal shape (FIG. 19A, *). At P5 and P8 cells cultured on PDMS$_{50+COL4}$ had a significantly smaller HSF than those cultured on TCPS and TCPS$_{COL4}$ thus having a more hexagonal character (FIG. 19A, #). Cells with a larger area are more spread which indicates a more fibroblastic phenotype. Comparisons of cell area showed CECs cultured on TCPS$_{COL4}$ had a significantly smaller cell area than those cultured on TCPS (FIG. 19B, *). At all passages, cells cultured on PDMS$_{50+COL4}$ had a significantly smaller cell area then cells cultured on both TCPS and TCPS$_{COL4}$ (FIG. 19B, #) correlating with the higher cell density observed at each passage.

Discussion:

This study demonstrates the use of a high content screen that spans a three order of magnitude range of stiffness and six different surface coatings to determine the most effective method for culture of cells that otherwise exhibit little ability to proliferative in vitro. In this case, the initial screening of 36 substrates evaluated for cell morphology and protein localization allowed for the selection of one biomimetic substrate, with a collagen IV coating and elasticity of 50 kPa, on which at passage 3 the bovine CECs maintained a more polygonal cellular morphology, ZO-1 present at all borders and F-actin located cortically. We hypothesized that we could use this biomimetic substrate to increase the proliferative capacity of the CECs by culturing the cells on the substrate immediately upon isolation. Culturing and serially passaging the cells on the biomimetic substrate resulted in increased cell density and total number of cells as well as maintenance of morphology, mRNA expression levels and FN, F-actin and ZO-1 localization when compared to TCPS based tissue culture substrates. This is the first report of increasing the expansion of CECs by mimicking the CECs native environment, Descemet's membrane through substrate biomechanics.

Cells cultured on the biomimetic substrate reached confluence more quickly and had an increased cell density at each passage compared to cells cultured on the TCPS based substrates despite being initially seeding the same number of cornea isolates. This increase in cell density suggests an increase in the proliferative capacity of the cells or a delaying of cell senescence. Increasing the expansion of the cells is necessary for therapeutic applications in which donor cells are the limiting factor. Maintaining the cellular phenotype is equally as important for therapeutic applications as increasing the number of cells. CECs cultured on PDMS$_{50+COL4}$ maintained their polygonal shape up to passage 8 which was quantified by the significantly smaller cell area and hexagon shape factor at passages 5 and 8. The smaller cell shape suggests a delay in cell spreading and loss of phenotype through EMT. Our qRT-PCR and protein localization data further indicates a delay of EMT in cells cultured on PDMS$_{50+COL4}$. The levels of COL3A1 and COL8A1 on both collagen IV coated substrates were similar to one another and to that of the uncultured bovine CECs. In contrast, the level of SLC4A4 mRNA expression on the biomimetic substrate was more similar to the uncultured CECs at later passages, whereas the level expressed by cells cultured on both TCPS based surfaces was much lower. The structure of the FN fibers produced by the cells was clearly different at passages 5 and 8. The FN fibers produced by the cells on the biomimetic substrate remained small and immature as opposed to becoming long mature fibers that are produced by cells with a more fibroblastic phenotype. These results show that it is the synergy between the surface mechanics and chemistry of the biomimetic substrate that helps the cells to maintain a cellular phenotype more similar to that of the uncultured CE compared to the cells cultured on the TCPS based substrates. After comparing all experimental results, it was determined that cells on TCPS and $TCPS_{COL4}$ no longer exhibit a CE phenotype after passage 5 while cells on $PDMS_{50+COL4}$ maintain CE phenotype until passage 8. From this information, it was calculated that using the biomimetic substrate for cell culture increased the expansion of bovine CE cells from ~139 fold on standard TCPS to over 3000 fold. Further expansion of the cells could be achieved if further optimization was performed on the substrate characteristics or passaging methods.

The biggest limitations in the field of corneal endothelium tissue engineering and therapies are the low number of available donor corneas with a suitable endothelium and inability of the CECs to proliferate in vitro. This creates a demand for new technologies to expand these cells in vitro. Different strategies have been applied to determine why the cells do not proliferate and many approaches with changes in culture media have been studied to try and induce the cells to proliferate. Some methods like the addition of the ROCK inhibitor Y27632 have shown promise, but the effect of these treatments on the cells once they are transplanted in vivo is still unknown (Okumura N, et al. (2011) Enhancement of corneal endothelium wound healing by Rho-associated kinase (ROCK) inhibitor eye drops. *British Journal of Ophthalmology* 95(7):1006-1009; Okumura N, et al. (2009) Enhancement on Primate Corneal Endothelial Cell Survival In Vitro by a ROCK Inhibitor. *Investigative ophthalmology & visual science* 50(8):3680-3687; and Yamamoto M, et al. (2011) The effect of ROCK inhibitor on corneal wound healing and the transformation of keratocytes. *International Journal of Experimental Pathology* 92(3):A15-A15). We are currently investigating PDMS50+COL4 to increase the expansion of human CECs for therapeutic applications. The ability to delay senescence and EMT of human CECs through control of substrate biomechanics would be beneficial for clinical applications. Genetic changes to cells and addition of small molecules to culture conditions during expansion are more likely to elicit caution in regulatory (e.g., FDA) approval processes, while a mere change to culture surfaces that does not genetically or chemically affect the cells is less likely to raise concerns during regulatory approval. Additionally, the high content screen method employed here to determine the a better cell culture substrate for the CECs could be applied to other cell types or be used as an investigative tool to observe the effect of surface mechanics and chemistry in a systematic approach. This strategy could lead to the expansion of other cell types with limited in vitro proliferation that are needed to further advance regenerative medicine therapies.

Example 3—Engineering CE Monolayers on Thin Films

Figure 20:
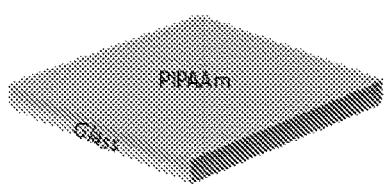
FIG. 20 depicts a method of preparing a corneal endothelial thin film on a PDMS substrate as described herein.
Figure 20:
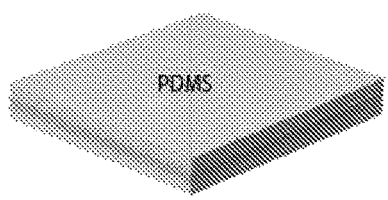
Figure 20:
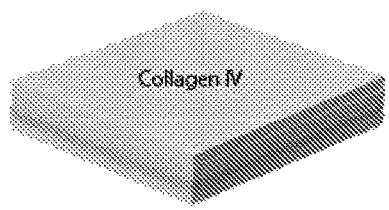
Figure 20:
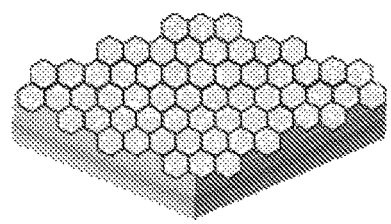
Figure 20:
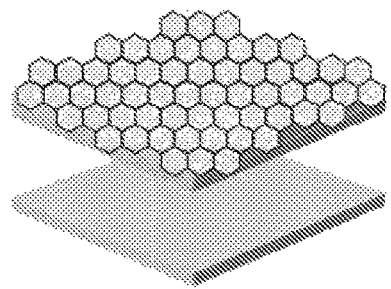
Figure 20:
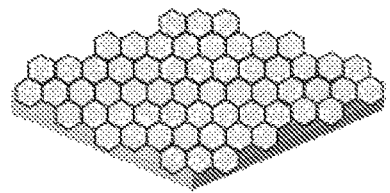
Figure 21:
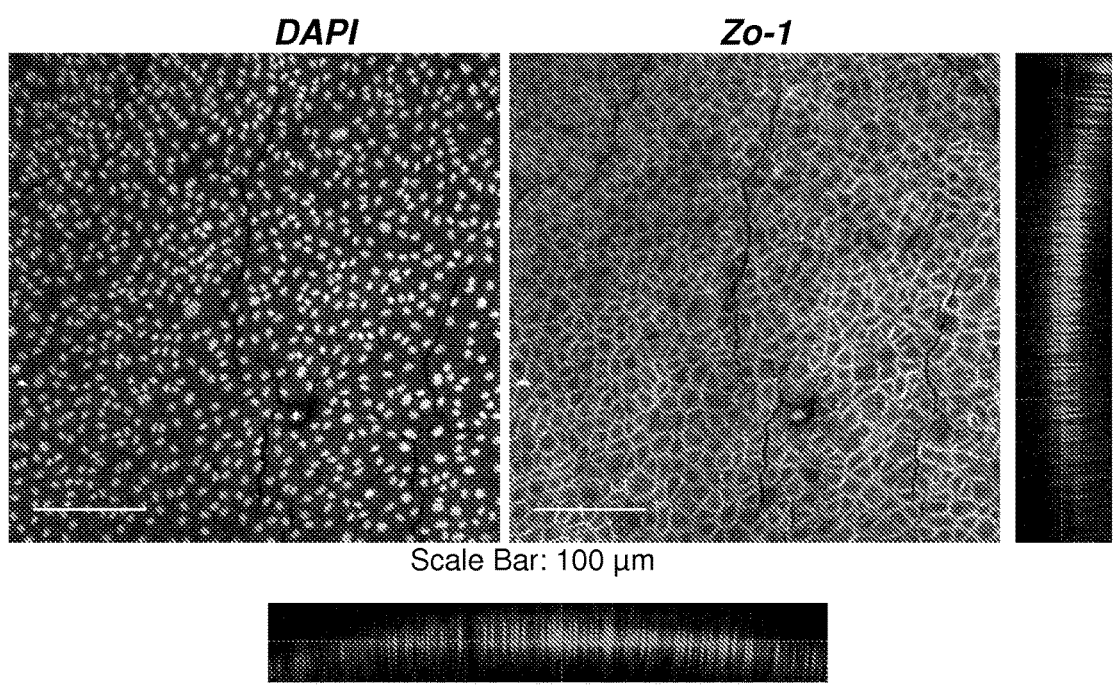
FIG. 21 exemplary monolayer of corneal endothelial cells was prepared on a Sylgard 184 substrate according to Example 3, and stained with DAPI (left) and anti-ZO-1 antibody (right) in the manner described herein.

A method is provided for producing a thin monolayer on the substrate described herein, essentially as shown in FIGS. 20 and 21. In this method, a glass slide is coated with the thermally-responsive (co)polymer poly(N-isopropylacrylamide) (PIPAAm). Next, the PIPAAm layer is coated with a layer of the Sylgard 184 and Sylgard 527 mixture in ratios described above and then is coated with collagen IV. The coated slide is placed in a tissue culture flask with the siloxane-containing layer exposed and submerged in tissue culture media. Cells are deposited onto the coated slide and the cells are cultured to confluence at 37° C. The siloxane-containing layer, including the confluent monolayer is then removed from the slide by lowering the temperature of the slide to a temperature where the PIPAAm is solubilized. An exemplary monolayer of corneal endothelial cells was prepared on a Sylgard 184 substrate according to these methods, as shown in FIG. 21.

Example 4—Manufacture of a Corneal Endothelium Layer for Implantation

A sterile glass disc is prepared that is approximately 15 mm in diameter. Using sterile technique, the disc is coated first with PIPAAm as described above, followed by a thin layer of a PDMS50+COL4 composition prepared essentially as described above but molded with pores. The disc is placed with the PDMS50+COL4 side facing up in a tissue culture flask containing serum-free tissue culture media. Healthy corneal endothelium cells are obtained from a patient and are cultured at 37° C. on the disc until a confluent monolayer is formed. The $PDMS50_+COL4$ and cell monolayer are released. The monolayer is washed and then is implanted.

Example 5—Manufacture of Expanding Corneal Endothelium Cells, e.g., for Use in Production of Tissue Constructs or for Drug Testing A tissue culture flask and a culture dish are prepared coated with a thin layer of a $PDMS_{50+COL4}$ composition prepared essentially as described above. Serum-free tissue culture media is added to the flask and the dish and corneal endothelium cells are obtained from a patient and are cultured at 37° C. in both the flask and the dish for from three to ten days. The cells are released from the PDMS substrate by trypsinization. Cells prepared in this manner may be used for production of a corneal endothelium layer, such as for seeding a biodegradable scaffold or for other purposes, such as for testing drug compounds.

Example 6—Growth of Retinal Pigment Epithelial Cells

It is expected that culture of adult, fetal and stem cell-derived human RPE cells would be enhanced on our bioscaffold by maintaining phenotype and reducing the EMT process.

Isolation of adult human RPE cells would be achieved by standard procedures, with the main difference that once cells are isolated from the eye, they will be cultured entirely on our bioscaffold rather than standard cell culture surfaces such as glass or tissue culture plastic. Briefly, to harvest adult of fetal RPE, starting with the intact globe, the anterior segment is first removed followed by removal of the vitreous body and separation of the neural retina from the RPE. Next, incubation with HBSS and EDTA for 15-30 min is used to to remove the RPE cells from Bruch's membrane. After incubation, the RPE that was separated from the rest of the eye is gently removed with pipette, and placed into sterile media (DMEM/F12 10% FBS, 1% antibiotics) and centrifuged 100 rpm 5 min. The cells are then resuspended in sterile media with 2 mM glutamine, 1% nonessential amino acids, 20 ng/mL bFGF, 1% N2 supplement an antibiotics. Confluent cultures cells are passaged 1:3 or 1:4 to $1-2\times10^4$ cells/$cm^2$ in media with 5% serum using trypsin/EDTA. On standard tissue culture plastic the RPE cells take at least 21-28 days to reach confluence in primary cultured, and passaged cells take 7-17 days, it is expected that the growth rat will be faster on the bioscaffold. Methods for primary harvest/culture from Kuznetsova et al (2011) (Cell and Tissue Biology 5(5):495-502).

Having described this invention above, it will be understood to those of ordinary skill in the art that the same can be performed within a wide and equivalent range of conditions, formulations and other parameters without affecting the scope of the invention or any embodiment thereof.

This application claims the benefit of U.S. Provisional Patent Application No. 61/632,787, filed Jan. 31, 2012 and U.S. Provisional Patent Application No. 61/735,249, filed Dec. 10, 2012, each of which is incorporated herein by reference in its entirety.

We claim:

1. A bioscaffold comprising:
a sterile substrate comprising a crosslinked mixture of a first composition comprising a polysiloxane and nanoparticles and a second composition comprising independently a polysiloxane and which does not comprise nanoparticles, and an extracellular matrix (ECM) component deposited on a surface of the crosslinked mixture; and
cells grown or cultured on the sterile substrate.

2. The bioscaffold of claim 1 in which the first composition further comprises polydimethyl siloxane, one or more siloxanes other than polydimethyl siloxane, and silica nanoparticles; and the second composition comprises one or both of a polydimethylsiloxane and a dimethyl, methylhydrogen siloxane.

3. The bioscaffold of claim 1, in which the polysiloxane of the first and second compositions independently comprise one or more of a dimethyl siloxane; a diphenylsiloxane; a diethylsiloxane; a trifluoropropyl methyl siloxane; a phenylmethylsiloxane; a copolymer of dimethylsiloxane with one or more of a diphenylsiloxane, a diethylsiloxane, a trifluoropropyl methyl siloxane, and/or a phenylmethylsiloxane; and a aminopropylmethylsiloxane-(dimethylsiloxane).

4. The bioscaffold of claim 1, in which the nanoparticles are silica nanoparticles.

5. The bioscaffold of claim 1, in which the nanoparticles comprise organically-modified silica.

6. The bioscaffold of claim 5, in which the organically-modified silica comprises one or more vinyl and/or alkyl groups.

7. The bioscaffold of claim 5, in which the organically-modified silica comprises one or both of dimethylvinylated silica and trimethylated silica.

8. The bioscaffold of claim 1, in which the polysiloxane of one or both of the first composition and the second composition is dimethylvinyl-terminated.

9. The bioscaffold of claim 1 in which the first composition comprises dimethylvinyl-terminated dimethyl siloxane, dimethylvinylated and trimethylated silica, and tetra(trimethylsiloxy) silane, and the second composition comprises a polydimethylsiloxane and a dimethyl, methylhydrogen siloxane.

10. The bioscaffold of claim 1, having an elastic modulus ranging from greater than 5 kPa to less than 1.72 MPa.

11. The bioscaffold of claim 1, having a mass ratio of the first composition to the second composition of from 50:1 to 1:50.

12. The bioscaffold of claim 1, in which a weight ratio of polysiloxane to nanoparticles is at least 2.5:1.

13. The bioscaffold of claim 1, in which the ECM component is patterned on a surface of the bioscaffold.

14. The bioscaffold of claim 1, in which the ECM component comprises one or more of a glycosaminoglycan; a proteoglycan; a protein; and a glycoprotein.

15. The bioscaffold of claim 1, formed into a three-dimensional structure.

16. The bioscaffold of claim 1, formed as a porous mass, a woven mass of fibers or a non-woven mass of fibers.

17. The bioscaffold of claim 1, in which the cells are selected from the group consisting of a stem cell, a corneal endothelial cell or a progenitor thereof; a muscle cell or a progenitor thereof; a neuronal cell or a progenitor thereof, and a retinal pigment epithelial cell or a progenitor thereof.

18. The bioscaffold of claim 10, having an elastic modulus of between 5 kPa and 50 kPa.

19. The bioscaffold of claim 1, wherein the ECM component comprises one or more of a heparan sulfate, a dermatan sulfate, a chondroitin sulfate, a keratin sulfate, a hyaluronic acid, an aggrecan, a versican, a neurocan, a brevican, a decorin, a perlecan, a collagen, an elastin; a laminin, a fibronectin, a vitronectin, an osteopontin and a fibrinogen.

20. The bioscaffold of claim 1, further comprising a rigid or semi-rigid substrate onto which the sterile substrate is deposited.

* * * * *

UNITED STATES PATENT AND TRADEMARK OFFICE
CERTIFICATE OF CORRECTION

PATENT NO. : 10,119,119 B2
APPLICATION NO. : 14/375705
DATED : November 6, 2018
INVENTOR(S) : Adam Walter Feinberg et al.

It is certified that error appears in the above-identified patent and that said Letters Patent is hereby corrected as shown below:

Column 46, Line 39, Claim 19, delete "osteopontin" and insert -- osteopontin, --

Signed and Sealed this
Twelfth Day of February, 2019

Andrei Iancu
*Director of the United States Patent and Trademark Office*